US012765161B2

(12) United States Patent
Cho et al.

(10) Patent No.: US 12,765,161 B2
(45) Date of Patent: Oct. 13, 2026

(54) COMPOUND, LIGHT-EMITTING MATERIAL, AND LIGHT-EMITTING ELEMENT

(71) Applicant: KYULUX, INC., Fukuoka (JP)

(72) Inventors: Yong Joo Cho, Fukuoka (JP); Yoshitake Suzuki, Fukuoka (JP); Masataka Yamashita, Fukuoka (JP); Naomi Shimamura, Fukuoka (JP); Yu Yamane, Fukuoka (JP); Satoshi Ohno, Fukuoka (JP); Shinhyung Choi, Fukuoka (JP); Noboru Sanada, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 18/564,003

(22) PCT Filed: Sep. 24, 2021

(86) PCT No.: PCT/JP2021/034975
§ 371 (c)(1),
(2) Date: Nov. 24, 2023

(87) PCT Pub. No.: WO2022/249506
PCT Pub. Date: Dec. 1, 2022

(65) Prior Publication Data

US 2024/0298538 A1 Sep. 5, 2024

(30) Foreign Application Priority Data

May 27, 2021 (WO) .................. PCT/JP2021/020163

(51) Int. Cl.
*H10K 50/12* (2023.01)
*C07D 491/048* (2006.01)
(Continued)

(52) U.S. Cl.
CPC ....... *H10K 50/121* (2023.02); *C07D 491/048* (2013.01); *C07D 495/04* (2013.01);
(Continued)

(58) Field of Classification Search
CPC .............. C09D 491/048; C07D 495/04; H10K 85/657; H10K 85/3572; H10K 85/354; H10K 50/401; H10K 2101/20
(Continued)

(56) References Cited

U.S. PATENT DOCUMENTS

| | | | |
|---|---|---|---|
| 2018/0062085 | A1 | 3/2018 | Bergmann et al. |
| 2018/0062086 | A1 | 3/2018 | Fabio et al. |

(Continued)

FOREIGN PATENT DOCUMENTS

| | | | |
|---|---|---|---|
| CN | 107778214 | A | 3/2018 |
| CN | 107778294 | A | 3/2018 |

(Continued)

OTHER PUBLICATIONS

Japanese and English version of International Preliminary Report on Patentability of Chapter I, i.e., International Search Opinion issued on Nov. 21, 2023.

(Continued)

*Primary Examiner* — Tri V Nguyen
(74) *Attorney, Agent, or Firm* — Troutman Pepper Locke LLP; James E. Armstrong, IV

(57) ABSTRACT

A compound represented by the following general formula is an excellent light emitting material. $R^1$ to $R^5$ each represent a hydrogen atom, a deuterium atom, or a substituent other than a cyano group, but one or more of $R^1$ to $R^5$ is an aryl group or a pyridyl group, two or more of $R^1$ to $R^5$ are donor groups, and one or more of them are a substituted ring-fused indol-1-yl group (the number of rings constituting the fused ring is 4 or more).

12 Claims, 1 Drawing Sheet

(51) Int. Cl.

| | |
|---|---|
| ***C07D 495/04*** | (2006.01) |
| ***C09K 11/02*** | (2006.01) |
| ***C09K 11/06*** | (2006.01) |
| ***H10K 50/00*** | (2023.01) |
| ***H10K 50/11*** | (2023.01) |
| ***H10K 85/60*** | (2023.01) |
| ***H10K 101/10*** | (2023.01) |
| ***H10K 101/20*** | (2023.01) |

(52) U.S. Cl.
CPC .............. *C09K 11/02* (2013.01); *C09K 11/06* (2013.01); *H10K 50/11* (2023.02); *H10K 50/401* (2023.02); *H10K 85/657* (2023.02); *H10K 85/6572* (2023.02); *C09K 2211/1007* (2013.01); *C09K 2211/1018* (2013.01); *H10K 50/12* (2023.02); *H10K 85/658* (2023.02); *H10K 2101/10* (2023.02); *H10K 2101/20* (2023.02)

(58) Field of Classification Search
USPC .......................................... 252/500, 510, 511
See application file for complete search history.

(56) References Cited

U.S. PATENT DOCUMENTS

2019/0058130 A1 2/2019 Aguilera-Iparraguirre et al.
2020/0115364 A1* 4/2020 Aguilera-Iparraguirre .................. C07D 403/14

FOREIGN PATENT DOCUMENTS

| | | | | |
|---|---|---|---|---|
| EP | 3670508 | A1 * | 6/2020 | ......... H10K 85/6572 |
| KR | 10-2021-0050829 | A | 5/2021 | |
| WO | 2018/155642 | A1 | 8/2018 | |
| WO | 2018/237389 | A1 | 12/2018 | |
| WO | 2019002175 | A1 | 1/2019 | |
| WO | 2019238471 | A1 | 12/2019 | |
| WO | 2021046523 | A1 | 3/2021 | |

OTHER PUBLICATIONS

International Search Report and Search Opinion with English translation mailed on Nov. 2, 2021.
Office Action dated Mar. 5, 2025 issued in the corresponding Japanese patent application No. 2023-523948 with its English Machine Translation.
Office Action issued in Chinese Patent Application No. CN 202180098537.4, mailed Sep. 6, 2025, with English translation.
Office Action issued in corresponding Chinese Patent Application No. CN 202180098537.4, mailed Feb. 12, 2026, with English translation.
Rejection Decision dated May 29, 2026, issued in the corresponding Chinese patent application No. 202180098537.4 with its English machine translation.

* cited by examiner

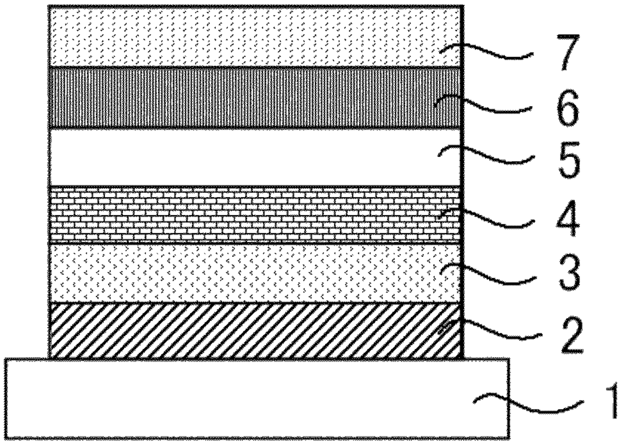
7
6
5
4
3
2
1

COMPOUND, LIGHT-EMITTING MATERIAL, AND LIGHT-EMITTING ELEMENT

TECHNICAL FIELD

The present invention relates to a compound useful as a light emitting material, and a light emitting device using the compound.

BACKGROUND ART

Studies for enhancing the light emission efficiency of light emitting devices such as organic electroluminescent devices (organic EL devices) are being made actively. In particular, various kinds of efforts have been made for increasing light emission efficiency by newly developing and combining an electron transporting material and a hole transporting material to constitute an organic electroluminescent device. Among them, there are seen some reports relating to an organic electroluminescent device that utilizes a delayed fluorescent material.

A delayed fluorescent material is a material which, in an excited state, after having undergone reverse intersystem crossing from an excited triplet state to an excited singlet state, emits fluorescence when returning back from the excited singlet state to a ground state thereof. Fluorescence through the route is observed later than fluorescence from the excited singlet state directly occurring from the ground state (ordinary fluorescence), and is therefore referred to as delayed fluorescence. Here, for example, in the case where a light emitting compound is excited through carrier injection thereinto, the occurring probability of the excited singlet state to the excited triplet state is statistically 25%/75%, and therefore improvement of light emission efficiency by the fluorescence alone from the directly occurring excited singlet state is limited. On the other hand, in a delayed fluorescent material, not only the excited singlet state thereof but also the excited triplet state can be utilized for fluorescent emission through the route via the above-mentioned reverse intersystem crossing, and therefore as compared with an ordinary fluorescent material, a delayed fluorescent material can realize a higher emission efficiency.

Since such a principle has been clarified, various studies have led to the discovery of various delayed fluorescent materials. Among these, many compounds in which cyanobenzene is substituted with a donor group are included. As a typical compound, cyanobenzene in which a carbazol-9-yl group is substituted as described below has been proposed (see PTL 1).

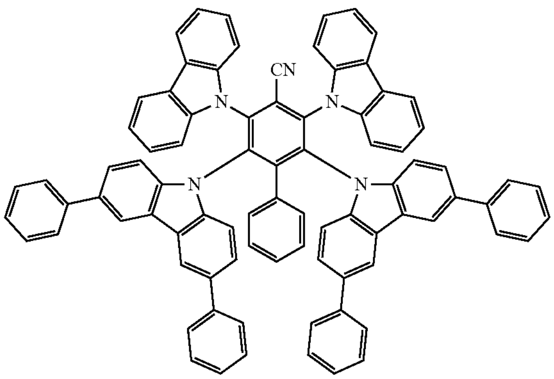 [SMILES: N#Cc1c(-n2c3ccccc3c3ccccc32)c(-n2c3ccc(-c4ccccc4)cc3c3cc(-c4ccccc4)ccc32)c(-c2ccccc2)c(-n2c3ccc(-c4ccccc4)cc3c3cc(-c4ccccc4)ccc32)c1-n1c2ccccc2c2ccccc21]

CITATION LIST

Patent Literature

PTL 1: WO2018/155642A.1

SUMMARY OF INVENTION

Technical Problem

Even if a material emits delayed fluorescence, a material having extremely good characteristics and having no problem in practical use has not been provided. Therefore, for example, it is more useful if it is possible to provide a compound having a higher light emission efficiency and a shorter delayed fluorescence lifetime than the compound described in PTL 1. However, it is generally extremely difficult to improve the delayed fluorescence lifetime and durability while improving the light emission efficiency. In addition, the improvement of delayed fluorescent materials is in the stage of trial and error, and it is not easy to generalize the chemical structure of useful light emitting materials.

Under such circumstances, the present inventors have conducted research for the purpose of providing a compound more useful as a light emitting material for a light emitting device. Then, the present inventors have conducted intensive studies for the purpose of deriving and generalizing a general formula of a compound more useful as a light emitting material.

Solution to Problem

As a result of intensive studies for achieving the above object, the present inventors have found that a cyanobenzene compound having a structure satisfying a specific condition is useful as a light emitting material. The present invention has been proposed based on these findings, and specifically has the following configuration.

[1] A compound represented by the following general formula (1):

General formula (1)

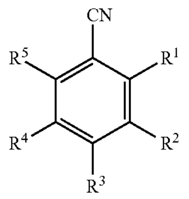

in which $R^1$ to $R^5$ each independently represent a hydrogen atom, a deuterium atom, or a substituent other than a cyano group, provided that at least one of $R^1$ to $R^5$ is a substituted or unsubstituted aryl group or a substituted or unsubstituted pyridyl group, at least two of $R^1$ to $R^5$ are donor groups, and at least one of the two or more donor groups is a substituted ring-fused indol-1-yl group (the number of rings constituting the fused ring is 4 or more), and $R^1$ and $R^2$, $R^2$ and $R^3$, $R^3$ and $R^4$, or $R^4$ and $R^5$ may be bonded to each other to form a cyclic structure.

[2] The compound according to [1], in which the substituted ring-fused indol-1-yl group is a substituted ring-fused carbazol-9-yl group.

[3] The compound according to [1], in which the substituted ring-fused indol-1-yl group is a ring-fused carbazol-9-yl group substituted with an aryl group or a heteroaroyl group.

[4] The compound according to [1], in which the substituted ring-fused indol-1-yl group is a ring-fused carbazol-9-yl group substituted with an aryl group.

[5] The compound according to any one of [1] to [4], in which the substituted ring-fused indol-1-yl group is a carbazol-9-yl group in which a ring having one or more atoms selected from the group consisting of an oxygen atom, a sulfur atom, and a nitrogen atom as a ring skeleton-constituting atom is fused.

[6] The compound according to any one of [1] to [4], in which the substituted ring-fused indol-1-yl group is a carbazol-9-yl group in which a ring having one or more atoms selected from the group consisting of an oxygen atom and a sulfur atom as a ring skeleton-constituting atom is fused.

[7] The compound according to any one of [1] to [6], in which two to four of $R^1$ to $R^5$ are substituted or unsubstituted ring-fused indol-1-yl groups, and the two to four substituted or unsubstituted ring-fused indol-1-yl groups are two or more kinds.

[8] The compound according to [7], in which one of the two or more kinds is a substituted ring-fused indol-1-yl group, and the other one is an unsubstituted ring-fused indol-1-yl group.

[9] The compound according to [7] or [8], in which one of the two or more kinds is a carbazol-9-yl group in which a ring having one or more atoms selected from the group consisting of an oxygen atom, a sulfur atom, and a nitrogen atom as a ring skeleton-constituting atom is fused, and the other one is a carbazol-9-yl group in which a ring is not fused.

[10] The compound according to [7] or [8], in which one of the two or more kinds is a substituted or unsubstituted carbazol-9-yl group, and the other one is a carbazol-9-yl group substituted with a substituent different from the substituted or unsubstituted carbazol-9-yl group.

[11] The compound according to any one of [1] to [10], in which $R^1$ to $R^5$ are each independently a substituted or unsubstituted aryl group, or a substituted or unsubstituted ring-fused indol-1-yl group.

[12] The compound according to any one of [1] to [11], in which $R^1$ and $R^5$ are an unsubstituted ring-fused indol-1-yl group, $R^2$ is a substituted ring-fused indol-1-yl group, $R^4$ is a substituted or unsubstituted ring-fused indol-1-yl group, and $R^3$ is a substituted or unsubstituted aryl group.

[13] The compound according to any one of [1] to [12], in which the compound has a line-symmetric structure.

[14] The compound according to any one of [1] to [13], in which only $R^3$ is a substituted or unsubstituted aryl group.

[15] A light emitting material including the compound according to any one of [1] to [14].

[16] A delayed fluorescent material including the compound according to any one of [1] to [14].

[17] A film including the compound according to any one of [1] to [14].

[18] An organic semiconductor device including the compound according to any one of [1] to [14].

[19] An organic light emitting device including the compound according to any one of [1] to [14].

[20] The organic light emitting device according to [19], in which the device has a layer containing the compound, and the layer also contains a host material.

[21] The organic light emitting device according to [20], in which the layer containing the compound further contains a delayed fluorescent material in addition to the compound and the host material, and the delayed fluorescent material has a lowest excited singlet energy lower than that of the host material and higher than that of the compound.

[22] The organic light emitting device according to [20], in which the device has a layer containing the compound, and the layer also contains a light emitting material having a structure different from that of the compound.

[23] The organic light emitting device according to any one of [20] to [22], in which an amount of light emitted from the compound is the largest among materials contained in the device.

[24] The organic light emitting device according to [22], in which an amount of light emitted from the light emitting material is larger than an amount of light emitted from the compound.

[25] The organic light emitting device according to any one of [19] to [24], which is an organic electroluminescent device.

[26] The organic light emitting device according to any one of [19] to [24], which emits delayed fluorescence.

Advantageous Effects of Invention

The compound of the present invention is useful as a light emitting material. In addition, the compound of the present invention includes a compound having high light emission efficiency, a short delayed fluorescence lifetime, and excellent alignment property. Further, the organic light emitting device using the compound of the present invention also includes a device having high light emission efficiency, a long device lifetime, and excellent durability.

BRIEF DESCRIPTION OF DRAWING

FIG. 1 This is a schematic cross-sectional view showing an example of a layer configuration of an organic electroluminescent device.

DESCRIPTION OF EMBODIMENTS

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the numerical values described before and after "to" as the upper limit and the lower limit. Apart or all of hydrogen atoms existing in the molecule of the compound for use in the present invention can be substituted with deuterium atoms ($^2$H, deuterium D). In the chemical structural formulae in the description herein, the hydrogen atom is expressed as H, or the expression thereof is omitted. For example, when expression of the atoms bonding to the ring skeleton-constituting carbon atoms of a benzene ring is omitted, H is considered to bond to the ring skeleton-constituting carbon atom at the site having the omitted expression. In the chemical structural formulae in the present description, a deuterium atom is expressed as D.

[Compound Represented by General Formula (1)]

General formula (1)

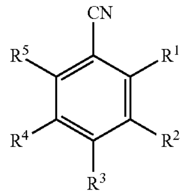

In the general formula (1), $R^1$ to $R^5$ each independently represent a hydrogen atom, a deuterium atom, or a substituent other than a cyano group.

At least one of $R^1$ to $R^5$ is a substituted or unsubstituted aryl group or a substituted or unsubstituted pyridyl group. Hereinafter, "a substituted or unsubstituted aryl group or a substituted or unsubstituted pyridyl group" is referred to as an Ar group. In one aspect of the present invention, at least $R^1$ is an Ar group. In one aspect of the present invention, at least $R^2$ is an Ar group. In one aspect of the present invention, at least $R^3$ is an Ar group. Among $R^1$ to $R^5$, the number of Ar groups is 1 to 4. In one aspect of the present invention, four of $R^1$ to $R^5$ are each an Ar group. In one aspect of the present invention, three of $R^1$ to $R^5$ are each an Ar group. For example, $R^1$, $R^3$, and $R^5$ are each an Ar group. For example, $R^2$, $R^3$, and $R^4$ are each an Ar group. For example, $R^1$, $R^2$, and $R^3$ are each an Ar group. For example, $R^1$, $R^2$, and $R^4$ are each an Ar group. For example, $R^1$, $R^3$, and $R^4$ are each an Ar group. In one aspect of the present invention, two of $R^1$ to $R^5$ are each an Ar group. For example, $R^1$ and $R^2$ are each an Ar group. For example, $R^1$ and $R^3$ are each an Ar group. For example, $R^1$ and $R^4$ are each an Ar group. For example, $R^1$ and $R^5$ are each an Ar group. For example, $R^2$ and $R^3$ are each an Ar group. For example, $R^2$ and $R^4$ are each an Ar group. In one aspect of the present invention, only one of $R^1$ to $R^5$ is an Ar group. In a preferred aspect of the present invention, only $R^3$ is an Ar group. In one aspect of the present invention, only $R^2$ is an Ar group. In one aspect of the present invention, only $R^1$ is an Ar group.

The aryl group which is employable by $R^1$ to $R^5$ may be a monocyclic ring or a fused ring in which two or more rings are fused. In the case of a fused ring, the number of fused rings is preferably 2 to 6, and can be selected from, for example, 2 to 4. Specific examples of the ring include a benzene ring, a naphthalene ring, an anthracene ring, a phenanthrene ring, and a triphenylene ring. In one aspect of the present invention, the aryl group is a substituted or unsubstituted phenyl group, a substituted or unsubstituted naphthalen-1-yl group, or a substituted or unsubstituted naphthalen-2-yl group, and is preferably a substituted or unsubstituted phenyl group. The substituent of the aryl group may be selected from Substituent Group A which will be described later, may be selected from Substituent Group B which will be described later, may be selected from Substituent Group C which will be described later, may be selected from Substituent Group D which will be described later, or may be selected from Substituent Group E which will be described later. In addition, the substituent of the aryl group may be one group selected from the group consisting of a cyano group, an alkyl group (for example, having 1 to 20 carbon atoms), and an aryl group (for example, having 6 to 22 carbon atoms), or a group obtained by combining two or more groups.

The pyridyl group which is employable by $R^1$ to $R^5$ may be any of a 2-pyridyl group, a 3-pyridyl group, and a 4-pyridyl group, and may be a group in which a ring is fused to these groups or a group in which these hydrogen atoms are substituted. With regard to the substituent, the description of the substituent of the aryl group can be referred to. When a ring is further fused to the pyridyl group, the ring may be any of an aromatic hydrocarbon ring, an aromatic heterocyclic ring, an aliphatic hydrocarbon ring, and an aliphatic heterocyclic ring, and may be a ring obtained by further fusing these rings. An aromatic hydrocarbon ring and an aromatic heterocyclic ring are preferable. Examples of the aromatic hydrocarbon ring include a substituted or unsubstituted benzene ring. Another benzene ring may be further fused to the benzene ring, and a heterocyclic ring such as a pyridine ring may be fused to the benzene ring. The aromatic heterocyclic ring means a ring exhibiting aromaticity including a hetero atom as a ring skeleton-constituting atom, and is preferably a 5- to 7-membered ring. For example, a 5-membered ring or a 6-membered ring can be employed.

Specific examples of the Ar group which can be employed in the general formula (1) are shown below. However, the Ar group which can be employed in the present invention shall not be construed as being limited by the following specific examples. In the following specific examples, D represents a deuterium atom, t-Bu represents a tert-butyl group, and * represents a bonding site.

Ar1

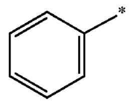

Ar2

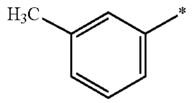

Ar3

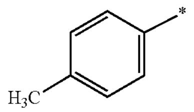

Ar4

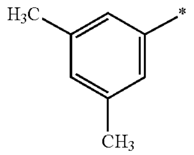

Ar5

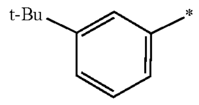

Ar6

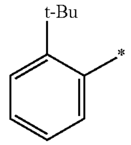

Ar7

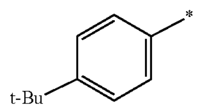

-continued
Ar8
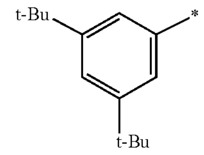
Ar9
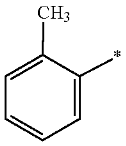
Ar10
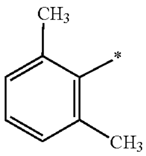
Ar11
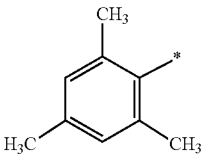
Ar12
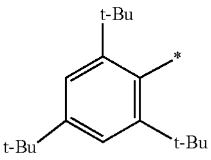
Ar13
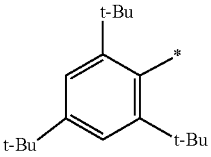
Ar14
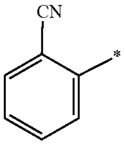
Ar15
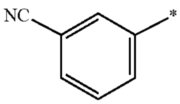
Ar16
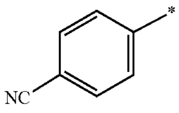
Ar17
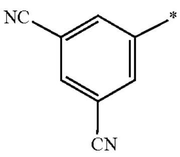
-continued
Ar18
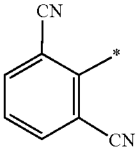
Ar19
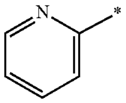
Ar20
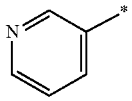
Ar21
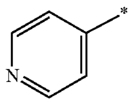
Ar22
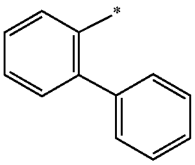
Ar23
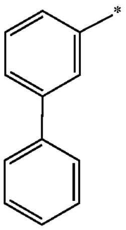
Ar24
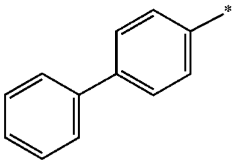
Ar25
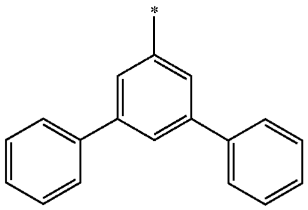
Ar26
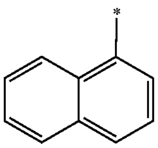

-continued

Ar27

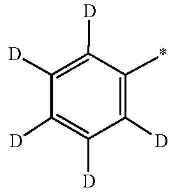

Those obtained by substituting all hydrogen atoms bonded to an alkyl group or a phenyl group as a substituent in Ar2 to Ar14 and Ar22 to Ar25 described above with deuterium atoms are exemplified herein as Ar2(d) to Ar14(d) and Ar22(d) to Ar25(d). In addition, those obtained by substituting all hydrogen atoms bonded to Ar2 to Ar26 with deuterium atoms are exemplified herein as Ar2(D) to Ar26 (D).

In the general formula (1), at least two of $R^1$ to $R^5$ are donor groups, and at least one of the two or more donor groups is a substituted ring-fused indol-1-yl group (the number of rings constituting the fused ring is 4 or more). That is, at least one of $R^1$ to $R^5$ is a substituted ring-fused indol-1-yl group (the number of rings constituting the fused ring is 4 or more). Hereinafter, the "substituted or unsubstituted ring-fused indol-1-yl group (the number of rings constituting the fused ring is 4 or more)" is referred to as an IDL group. The number of rings constituting the fused ring is 4 or more means that at least two rings are fused to the indol-1-yl group. More specifically, at least one fused ring is fused to the indol-1-yl group, or at least two monocyclic rings are fused to the indol-1-yl group. Since the carbazol-9-yl group has a structure in which three rings are fused, it is necessary to obtain a carbazol-9-yl group in which at least one ring is fused in order to obtain an IDL group. The number of rings constituting the fused ring in the IDL group is preferably 4 to 9, and more preferably 4 to 7. In one aspect of the present invention, the number of rings constituting the fused ring is 4. In one aspect of the present invention, the number of rings constituting the fused ring is 5. In one aspect of the present invention, the number of rings constituting the fused ring is 7.

In one aspect of the present invention, at least $R^5$ is an IDL group. In one aspect of the present invention, at least $R^4$ is an IDL group. In one aspect of the present invention, at least $R^3$ is an IDL group. Among $R^1$ to $R^5$, the number of IDL groups is 1 to 4. In one aspect of the present invention, four of $R^1$ to $R^5$ are each an IDL group. In one aspect of the present invention, three of $R^1$ to $R^5$ are each an IDL group. For example, $R^1$, $R^3$, and $R^5$ are each an IDL group. For example, $R^2$, $R^3$, and $R^4$ are each an IDL group. For example, $R^3$, $R^4$, and $R^5$ are each an IDL group. For example, $R^2$, $R^4$, and $R^5$ are each an IDL group. For example, $R^2$, $R^3$, and $R^5$ are each an IDL group. In one aspect of the present invention, two of $R^1$ to $R^5$ are each an IDL group. For example, $R^4$ and $R^5$ are each an IDL group. For example, $R^3$ and $R^5$ are each an IDL group. For example, $R^2$ and $R^5$ are each an IDL group. For example, $R^1$ and $R^5$ are each an IDL group. For example, $R^3$ and $R^4$ are each an IDL group. For example, $R^2$ and $R^4$ are each an IDL group. In one aspect of the present invention, only one of $R^1$ to $R^5$ is an IDL group. In one aspect of the present invention, only $R^5$ is an IDL group. In one aspect of the present invention, only $R^4$ is an IDL group. In one aspect of the present invention, only $R^3$ is an IDL group.

In one aspect of the present invention, $R^3$ is an aryl group or a pyridyl group and at least $R^5$ is an IDL group. In one aspect of the present invention, $R^3$ is an aryl group or a pyridyl group and at least $R^4$ is an IDL group. In one aspect of the present invention, $R^3$ is an aryl group or a pyridyl group and at least $R^4$ and $R^5$ are each an IDL group. In one aspect of the present invention, $R^3$ is an aryl group or a pyridyl group and at least R and $R^5$ are each an IDL group. In one aspect of the present invention, $R^3$ is an aryl group or a pyridyl group and at least $R^1$ and $R^5$ are each an IDL group. In one aspect of the present invention, $R^3$ is an aryl group or a pyridyl group and at least $R^1$, $R^4$, and $R^5$ are each an IDL group. In one aspect of the present invention, $R^3$ is an aryl group or a pyridyl group and at least $R^2$, $R^4$, and $R^5$ are each an IDL group. In one aspect of the present invention, $R^3$ is an aryl group or a pyridyl group and $R^1$, $R^2$, $R^4$, and $R^5$ are each an IDL group.

In one aspect of the present invention, $R^2$ is an aryl group or a pyridyl group and at least $R^5$ is an IDL group. In one aspect of the present invention, $R^2$ is an aryl group or a pyridyl group and at least $R^4$ is an IDL group. In one aspect of the present invention, $R^2$ is an aryl group or a pyridyl group and at least $R^3$ is an IDL group. In one aspect of the present invention, $R^2$ is an aryl group or a pyridyl group and at least $R^1$ is an IDL group. In one aspect of the present invention, $R^2$ is an aryl group or a pyridyl group and at least $R^4$ and $R^5$ are each an IDL group. In one aspect of the present invention, $R^1$ is an aryl group or a pyridyl group and at least $R^3$ and $R^5$ are each an IDL group. In one aspect of the present invention, $R^2$ is an aryl group or a pyridyl group and at least $R^1$ and $R^5$ are each an IDL group. In one aspect of the present invention, $R^2$ is an aryl group or a pyridyl group and at least $R^3$ and $R^4$ are each an IDL group. In one aspect of the present invention, $R^2$ is an aryl group or a pyridyl group and at least $R^1$ and $R^4$ are each an IDL group. In one aspect of the present invention, $R^2$ is an aryl group or a pyridyl group and at least $R^1$ and $R^3$ are each an IDL group. In one aspect of the present invention, $R^2$ is an aryl group or a pyridyl group and at least $R^3$, $R^4$, and $R^5$ are each an IDL group. In one aspect of the present invention, $R^2$ is an aryl group or a pyridyl group and at least $R^1$, $R^4$, and $R^5$ are each an IDL group. In one aspect of the present invention, $R^2$ is an aryl group or a pyridyl group and at least $R^1$, $R^3$, and $R^4$ are each an IDL group. In one aspect of the present invention, $R^2$ is an aryl group or a pyridyl group and $R^1$, $R^3$, $R^4$, and $R^5$ are each an IDL group.

In one aspect of the present invention, $R^1$ is an aryl group or a pyridyl group and at least $R^5$ is an IDL group. In one aspect of the present invention, $R^1$ is an aryl group or a pyridyl group and at least $R^4$ is an IDL group. In one aspect of the present invention, $R^1$ is an aryl group or a pyridyl group and at least $R^3$ is an IDL group. In one aspect of the present invention, $R^1$ is an aryl group or a pyridyl group and at least $R^2$ is an IDL group. In one aspect of the present invention, $R^1$ is an aryl group or a pyridyl group and at least $R^4$ and $R^5$ are each an IDL group. In one aspect of the present invention, $R^1$ is an aryl group or a pyridyl group and at least $R^3$ and $R^5$ are each an IDL group. In one aspect of the present invention, $R^1$ is an aryl group or a pyridyl group and at least $R^2$ and $R^5$ are each an IDL group. In one aspect of the present invention, $R^1$ is an aryl group or a pyridyl group and at least $R^3$ and $R^4$ are each an IDL group. In one aspect of the present invention, $R^1$ is an aryl group or a pyridyl group and at least $R^2$ and $R^4$ are each an IDL group. In one aspect of the present invention, $R^1$ is an aryl group or a pyridyl group and at least $R^2$ and $R^3$ are each an IDL group. In one aspect of the present invention, $R^1$ is an aryl group or a pyridyl group and at least $R^3$, $R^4$, and $R^5$ are each an IDL group. In one aspect of the present invention, $R^1$ is an aryl group or a pyridyl group and at least $R^2$, $R^4$, and $R^5$ are each an IDL group. In one aspect of the present invention, $R^1$ is an aryl group or a pyridyl group and at least $R^2$, $R^3$, and $R^4$ are each an IDL group. In one aspect of the present invention, $R^1$ is an aryl group or a pyridyl group and $R^2$, $R^3$, $R^4$, and $R^5$ are each an IDL group.

The IDL group has a ring-fused indole structure in which a ring is fused to indole. Indole has a structure in which a benzene ring and a pyrrole ring are fused, but it is preferable that a ring is further fused to at least a pyrrole ring. In one aspect of the present invention, the ring is fused only to the pyrrole ring. In one aspect of the present invention, the ring is fused to the pyrrole ring and the benzene ring, respectively. The fused ring may be any of an aromatic hydrocarbon ring, an aromatic heterocyclic ring, an aliphatic hydrocarbon ring, and an aliphatic heterocyclic ring, and may be a ring obtained by further fusing these rings. An aromatic hydrocarbon ring and an aromatic heterocyclic ring are preferable. Examples of the aromatic hydrocarbon ring include a substituted or unsubstituted benzene ring. Another benzene ring may be further fused to the benzene ring, and a heterocyclic ring such as a pyridine ring may be fused to the benzene ring. The aromatic heterocyclic ring means a ring exhibiting aromaticity including a heteroatom as a ring skeleton-constituting atom, and is preferably a 5- to 7-membered ring. For example, a 5-membered ring or a 6-membered ring can be employed. In one aspect of the present invention, a furan ring, a thiophene ring, or a pyrrole ring can be employed as the aromatic heterocyclic ring. In one aspect of the present invention, the fused ring is a furan ring of substituted or unsubstituted benzofuran, a thiophene ring of substituted or unsubstituted benzothiophene, or a pyrrole ring of substituted or unsubstituted indole. It is preferable that a substituent selected from Substituent Group E is bonded to the nitrogen atom of the pyrrole ring, and it is more preferable that an aryl group which may be substituted with an alkyl group or an aryl group is substituted.

In one aspect of the present invention, the IDL group is a substituted ring-fused carbazol-9-yl group. In one aspect of the present invention, the IDL group is a ring-fused carbazol-9-yl group substituted with an aryl group. In one aspect of the present invention, the IDL group is a ring-fused carbazol-9-yl group substituted with a heteroaryl group. In one aspect of the present invention, the IDL group is a carbazol-9-yl group in which a ring having one or more atoms selected from the group consisting of an oxygen atom, a sulfur atom, and a nitrogen atom as a ring skeleton-constituting atom is fused. In one aspect of the present invention, the IDL group is a carbazol-9-yl group in which a ring having one or more atoms selected from the group consisting of an oxygen atom and a sulfur atom as a ring skeleton-constituting atom is fused.

When two to four of $R^1$ to $R^5$ are IDL groups, the two to four IDL groups may all be the same or different. In one aspect of the present invention, two to four of $R^1$ to $R^5$ are IDL groups, and these two to four IDL groups are composed of two or more kinds of IDL groups. For example, two kinds of IDL groups may be used. In one aspect of the present invention, when two or more kinds of IDL groups are present, one kind of the IDL groups is a carbazol-9-yl group in which a ring having one or more atoms selected from the group consisting of an oxygen atom, a sulfur atom, and a nitrogen atom as a ring skeleton-constituting atom is fused, and the other kind of the IDL groups is a carbazol-9-yl group in which a ring is not fused. In one aspect of the present invention, when two or more kinds of IDL groups are present, one kind of the IDL groups is a substituted or unsubstituted carbazol-9-yl group, and the other kind of the IDL groups is a different substituted or unsubstituted carbazol-9-yl group.

The IDL group is preferably a group represented by the following general formula (2).

General formula (2)

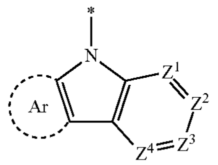

In the general formula (2), $Z^1$ represents C—$R^{11}$ or N, $Z^2$ represents C—$R^{12}$ or N, $Z^3$ represents C—$R^{13}$ or N, and $Z^4$ represents C—$R^{14}$ or N. Ar represents a substituted or unsubstituted aromatic hydrocarbon ring or a substituted or unsubstituted aromatic heterocyclic ring. $R^{11}$ and $R^{12}$, $R^{12}$ and $R^{13}$, or $R^{13}$ and $R^{14}$ may be bonded to each other to form a cyclic structure.

Among the groups represented by $Z^1$ to 4, the number of groups represented by N is preferably 0 to 3, and preferably 0 to 2. In one aspect of the present invention, among the groups represented by $Z^1$ to $Z^4$, the number of groups represented by N is 1. In one aspect of the present invention, among the groups represented by $Z^1$ to $Z^4$, the number of groups represented by N is 0.

$R^{11}$ to $R^{14}$ each independently represent a hydrogen atom, a deuterium atom, or a substituent.

For example, the substituent may be selected from Substituent Group A, may be selected from Substituent Group B, may be selected from Substituent Group C, may be selected from Substituent Group D, or may be selected from Substituent Group E. When two or more of $R^{11}$ to $R^{14}$ represent a substituent, the two or more substituents may be the same or different. Zero to two of $R^{11}$ to $R^{14}$ are preferably a substituent, and for example, one may be a substituent, or zero may be a substituent ($R^{11}$ to $R^{14}$ are a hydrogen atom or a deuterium atom). When $R^{11}$ to $R^{14}$ are a hydrogen atom or a deuterium atom, Ar represents a substituted aromatic hydrocarbon ring or a substituted aromatic heterocyclic ring.

$R^{11}$ and $R^{12}$, $R^{12}$ and $R^{13}$, or $R^{13}$ and $R^{14}$ may be bonded to each other to form a cyclic structure. The cyclic structure may be any of an aromatic hydrocarbon ring, an aromatic heterocyclic ring, an aliphatic hydrocarbon ring, and an aliphatic heterocyclic ring, and may be a ring obtained by fusing these rings. An aromatic hydrocarbon ring and an aromatic heterocyclic ring are preferable. Examples of the aromatic hydrocarbon ring include a substituted or unsubstituted benzene ring. Another benzene ring may be further fused to the benzene ring, and a heterocyclic ring such as a pyridine ring may be fused to the benzene ring. The aromatic heterocyclic ring means a ring exhibiting aromaticity including a heteroatom as a ring skeleton-constituting atom, and is preferably a 5- to 7-membered ring. For example, a 5-membered ring or a 6-membered ring can be employed. In one aspect of the present invention, a furan ring, a thiophene ring, or a pyrrole ring can be employed as the aromatic heterocyclic ring. In a preferred aspect of the present invention, the cyclic structure is a furan ring of substituted or unsubstituted benzofuran, a thiophene ring of substituted or unsubstituted benzothiophene, or a pyrrole ring of substituted or unsubstituted indole. The benzofuran, benzothiophene, and indole referred to herein may be unsubstituted, may be substituted with a substituent selected from Substituent Group A, may be substituted with a substituent selected from Substituent Group B, may be substituted with a substituent selected from Substituent Group C, may be substituted with a substituent selected from Substituent Group D, and may be substituted with a substituent selected from Substituent Group E. It is preferable that a substituted or unsubstituted aryl group is bonded to the nitrogen atom constituting the pyrrole ring of indole, and examples of the substituent include a substituent selected from any of Substituent Group A to Substituent Group E. The cyclic structure may be a substituted or unsubstituted cyclopentadiene ring. In one aspect of the present invention, a pair of $R^{11}$ and $R^{12}$, $R^{12}$ and $R^{13}$, or $R^{13}$ and $R^{14}$ is bonded to each other to form a cyclic structure. In one aspect of the present invention, none of $R^{11}$ and $R^{12}$, $R^{12}$ and $R^{13}$, or $R^{13}$ and $R^{14}$ is bonded to each other to form a cyclic structure.

In the general formula (2), Ar represents a substituted or unsubstituted aromatic hydrocarbon ring or a substituted or unsubstituted aromatic heterocyclic ring. In one aspect of the present invention, Ar is a substituted or unsubstituted aromatic hydrocarbon ring or a substituted or unsubstituted aromatic heterocyclic ring. In one aspect of the present invention, Ar is a substituted or unsubstituted aromatic heterocyclic ring.

Examples of the aromatic hydrocarbon ring which is employable by Ar include a benzene ring. Another benzene ring may be further fused to the benzene ring, and a heterocyclic ring such as a pyridine ring may be fused to the benzene ring. The aromatic heterocyclic ring which is employable by Ar is preferably a 5- to 7-membered ring. For example, a 5-membered ring or a 6-membered ring can be employed. In one aspect of the present invention, as the aromatic heterocyclic ring, a furan ring, a thiophene ring, a pyrrole ring, a pyridine ring, a pyridazine ring, a pyrimidine ring, or a pyrazine ring can be employed. In one aspect of the present invention, the aromatic heterocyclic ring is a furan ring of substituted or unsubstituted benzofuran, a thiophene ring of substituted or unsubstituted benzothiophene, a pyridine ring of substituted or unsubstituted quinoline, or a pyridine ring of substituted or unsubstituted isoquinoline. The benzofuran, benzothiophene, quinoline, and isoquinoline referred to herein may be unsubstituted, may be substituted with a substituent selected from Substituent Group A, may be substituted with a substituent selected from Substituent Group B, may be substituted with a substituent selected from Substituent Group C, may be substituted with a substituent selected from Substituent Group D, and may be substituted with a substituent selected from Substituent Group E. When Ar is an unsubstituted aromatic hydrocarbon ring or an unsubstituted aromatic heterocyclic ring, at least one of $R^{11}$ to $R^{14}$ is a substituent.

The IDL group is preferably a group represented by the following general formula (3).

General formula (3)

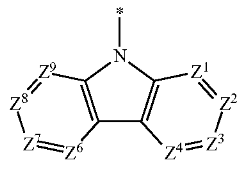

In the general formula (3), $Z^1$ represents C—$R^{11}$ or N, $Z^2$ represents C—$R^{12}$ or N, $Z^3$ represents C—$R^{13}$ or N, $Z^4$ represents C—$R^{14}$ or N, $Z^6$ represents C—$R^{16}$ or N, $Z^7$ represents C—$R^{17}$ or N, $Z^8$ represents C—$R^{18}$ or N, and $Z^9$ represents C—$R^{19}$ or N. $R^{11}$ and $R^{12}$, $R^1$ and $R^{13}$, $R^{13}$ and $R^{14}$, $R^{16}$ and $R^{17}$, $R^{17}$ and $R^{18}$, or $R^{18}$ and $R^{19}$ may be bonded to each other to form a cyclic structure.

For $Z^1$ to $Z^4$ and $R^{11}$ to $R^{14}$ in the general formula (3), the corresponding description of the general formula (2) can be referred to. $Z^6$ to $Z^9$ and $R^{16}$ to $R^{19}$ in the general formula (3) correspond to $Z^1$ to $Z^4$ and $R^{11}$ to $R^{14}$ in the general formula (2) in this order, and the contents thereof can be referred to the descriptions of $Z^1$ to $Z^4$ and $R^{11}$ to $R^{14}$ in the general formula (2). In the general formula (3), at least one of $R^{11}$ to $R^{14}$ and $R^{16}$ to $R^{19}$ is a substituent.

In one aspect of the present invention, among the groups represented by $Z^1$ to $Z^4$ and $Z^6$ to $Z^9$, the number of groups represented by N is preferably 0 to 2, and more preferably 0 or 1. In one aspect of the present invention, among the groups represented by $Z^1$ to $Z^4$ and $Z^6$ to $Z^9$, the number of groups represented by N is 1. In a preferred aspect of the present invention, among the groups represented by $Z^1$ to $Z^4$ and $Z^6$ to $Z^9$, the number of groups represented by N is 0. When the number is 0, the general formula (3) represents a substituted or unsubstituted carbazol-9-yl group. The carbazol-9-yl group may be unsubstituted, or may be substituted with a substituent selected from Substituent Group A, may be substituted with a substituent selected from Substituent Group B, may be substituted with a substituent selected from Substituent Group C, may be substituted with a substituent selected from Substituent Group D, and may be substituted with a substituent selected from Substituent Group E. The carbazol-9-yl group is preferably substituted with an aryl group, and is superior to the case of being substituted with a heteroaryl group in terms of light emission efficiency and device lifetime. In a preferred aspect of the present invention, the IDL group is a carbazol-9-yl group substituted with a group including at least one substituted or unsubstituted aryl group, for example, a carbazol-9-yl group substituted with at least one substituted or unsubstituted aryl group. In one aspect of the present invention, at least one of the 2- and 7-positions is a substituted or unsubstituted aryl group. In one aspect of the present invention, at least one of the 13- and 6-positions is a substituted or unsubstituted aryl group. The aryl group referred to herein may be unsubstituted, or may be substituted with a substituent selected from Substituent Group A, may be substituted with a substituent selected from Substituent Group B, may be substituted with a substituent selected from Substituent Group C, may be substituted with a substituent selected from Substituent Group D, and may be substituted with a substituent selected from Substituent Group E.

In the ring-fused indol-1-yl group, the ring fused to the benzene ring or pyrrole ring constituting the indol-1-yl group may be one monocyclic ring, may be one polycyclic ring, or may be two or more polycyclic or monocyclic rings. For example, when two groups are fused, it is preferable that one group is fused to a benzene ring and the other group is fused to a pyrrole ring. The two fused rings may be the same as or different from each other. The indole ring may be fused with a ring to form a fused ring having 4 or more, 5 or more, or 6 or more rings. For example, a compound forming a fused ring having 4 rings, a compound forming a fused ring having 5 rings, a compound forming a fused ring having 6 rings, a compound forming a fused ring having 7 rings, or a compound forming a fused ring having 8 rings may be employed.

The ring may be fused only to the 2- and 3-positions (b), may be fused only to the 4- and 5-positions (e), may be fused only to the 5- and 6-positions (f), may be fused only to the 6- and 7-positions (g), or may be fused to both the 4- and 5-positions (e) and the 6- and 7-positions (g) of the indole ring. Further, it may be fused to any one of the 4- and 5-positions (e), the 5- and 6-positions (t) and the 6- and 7-positions (g), and the 2- and 3-positions (b) (see the following formulae, * represents a bonding site).

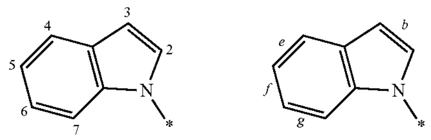

The ring directly fused to the benzene ring or pyrrole ring constituting the indol-1-yl group (in the case where the fused ring is a polycyclic ring, only the directly fused ring among the rings constituting the polycyclic ring is indicated) may be any of an aromatic hydrocarbon ring, an aromatic heterocyclic ring, an aliphatic hydrocarbon ring, and an aliphatic heterocyclic ring. Preferred is a case where one or more rings selected from the group consisting of a benzene ring and an aromatic heterocyclic ring are directly fused.

The heterocyclic ring referred to herein is a ring containing a hetero atom. The hetero atom is preferably selected from an oxygen atom, a sulfur atom, a nitrogen atom, and a silicon atom, and more preferably selected from an oxygen atom, a sulfur atom, and a nitrogen atom. In a preferred aspect, the hetero atom is an oxygen atom. In another preferred aspect, the hetero atom is a sulfur atom. In still another preferred aspect, the hetero atom is a nitrogen atom. The number of hetero atoms contained as the ring skeleton-constituting atoms of the heterocyclic ring is 1 or more, preferably 1 to 3, and more preferably 1 or 2. In a preferred aspect, the number of hetero atoms is 1. When the number of hetero atoms is two or more, they are preferably hetero atoms of the same kind, but may be constituted by hetero atoms of different kinds. For example, the two or more hetero atoms may be all nitrogen atoms. The ring skeleton-constituting atoms other than hetero atoms are carbon atoms. The number of ring skeleton-constituting atoms constituting the heterocyclic ring directly fused to the benzene ring constituting the indol-1-yl group is preferably 4 to 8, more preferably 5 to 7, and still more preferably 5 or 6. In a preferred aspect, the number of ring skeleton-constituting atoms constituting the heterocyclic ring is 5. It is preferable that two or more conjugated double bonds are present in the heterocyclic ring, and it is preferable that the conjugated system of the indole ring is expanded by the fusion of the heterocyclic ring (that is, it is preferable that the heterocyclic ring has aromaticity). Preferable examples of the heterocyclic ring include a furan ring, a thiophene ring, and a pyrrole ring.

The ring directly fused to the benzene ring or pyrrole ring constituting the indol-1-yl group may be further fused with another ring. The fused ring may be a monocyclic ring or a condensed ring. Examples of the fused ring include an aromatic hydrocarbon ring, an aromatic heterocyclic ring, an aliphatic hydrocarbon ring, and an aliphatic heterocyclic ring.

In a preferred aspect of the present invention, at least one heterocyclic ring is directly fused to the benzene ring or pyrrole ring constituting the indol-1-yl group. In a preferred aspect of the present invention, the fused ring constituting the ring-fused indol-1-yl group includes two or more heterocyclic rings. For example, a case where two heterocyclic rings are included or a case where three heterocyclic rings are included can be exemplified.

Examples of the aromatic hydrocarbon ring in the description herein include a benzene ring. Examples of the aromatic heterocyclic ring include a furan ring, a thiophene ring, a pyrrole ring, a pyridine ring, a pyridazine ring, a pyrimidine ring, a pyrazine ring, a triazine ring, a pyrrole ring, a pyrazole ring, and an imidazole ring. Examples of the aliphatic hydrocarbon ring include a cyclopentane ring, a cyclohexane ring, and a cycloheptane ring. Examples of the aliphatic heterocyclic ring include a piperidine ring, a pyrrolidine ring, and an imidazoline ring. Specific examples of the fused ring include a naphthalene ring, an anthracene ring, a phenanthrene ring, a pyran ring, a tetracene ring, an indole ring, an isoindole ring, a benzimidazole ring, a benzotriazole ring, a quinoline ring, an isoquinoline ring, a quinazoline ring, a quinoxaline ring, and a cinnoline ring.

In a preferred aspect of the present invention, the ring-fused indol-1-yl group is a benzofuran-fused indol-1-yl group, a benzothiophene-fused indol-1-yl group, an indole-fused indol-1-yl group, or a silaindene-fused indol-1-yl group. In a more preferred aspect of the present invention, the indol-1-yl group is a benzofuran-fused indol-1-yl group, a benzothiophene-fused indol-1-yl group, or an indole-fused indol-1-yl group.

In the present invention, a substituted or unsubstituted benzofuro[2,3-e]indol-1-yl group can be employed as the benzofuran-fused indol-1-yl group. Also a substituted or unsubstituted benzofuro[3,2-e]indol-1-yl group can be employed. Also a substituted or unsubstituted benzofuro[2,3-f]indol-1-yl group can be employed. Also a substituted or unsubstituted benzofuro[3,2-f]indol-1-yl group can be employed. Also a substituted or unsubstituted benzofuro[2,3-g]indol-1-yl group can be employed. Also a substituted or unsubstituted benzofuro[3,2-g]indol-1-yl group can be employed. The fused ring constituting these groups may or may not be further fused with another ring.

In the present invention, a substituted or unsubstituted benzofuro[2,3-a]carbazol-9-yl group can be employed as the benzofuran-fused indol-1-yl group. Also a substituted or unsubstituted benzofuro[3,2-a]carbazol-9-yl group can be employed. Also a substituted or unsubstituted benzofuro[2,3-b]carbazol-9-yl group can be employed. Also a substituted or unsubstituted benzofuro[3,2-b]carbazol-9-yl group can be employed. Also a substituted or unsubstituted benzofuro[2,3-c]carbazol-9-yl group can be employed. Also a substituted or unsubstituted benzofuro[3,2-c]carbazol-9-yl group can be employed. The fused ring constituting these groups may or may not be further fused with another ring.

Preferred examples of the benzofuran-fused indol-1-yl group include groups having any of the following structures, in which a hydrogen atom in the following structure may or may not be substituted, for example, those substituted with an aryl group such as a phenyl group or substituted at the 3-position of a carbazole ring can be preferably exemplified. Further, the benzene ring in the following structure may be further fused with a ring or may not be fused with a ring. A wavy line represents a bonding site.

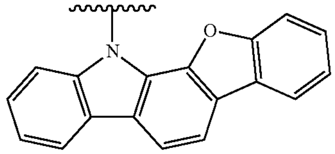

-continued

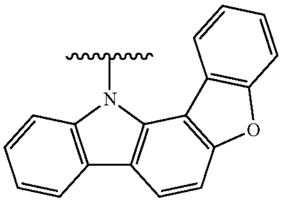

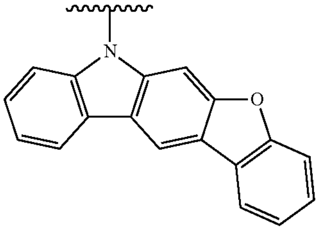

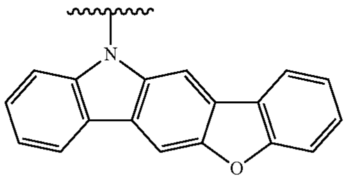

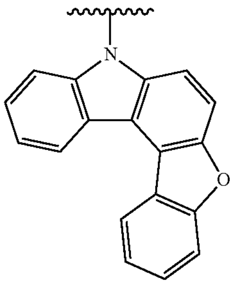

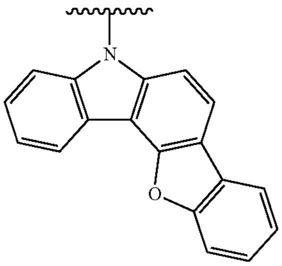

It is also possible to employ a carbazol-9-yl group in which two benzofuran rings are fused at its 2- and 3-positions. Specifically, it is a group having any one of the following structures, and a hydrogen atom in the following structure may or may not be substituted. Further, the benzene ring in the following structure may be further fused with a ring or may not be fused with a ring.

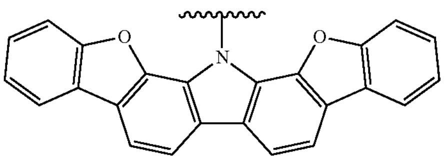

-continued

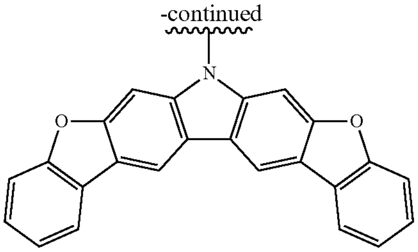

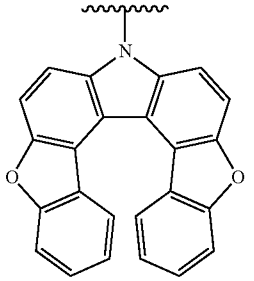

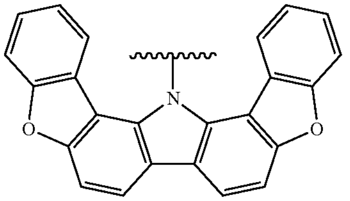

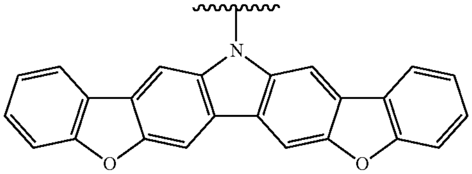

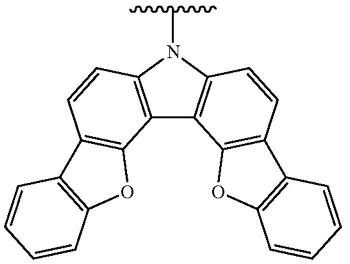

In the present invention, a substituted or unsubstituted benzothieno[2,3-e]indol-1-yl group can be employed as the benzothiophene-fused indol-1-yl group. Also a substituted or unsubstituted benzothieno[3,2-e]indol-1-yl group can be employed. Also a substituted or unsubstituted benzothieno[2,3-f]indol-1-yl group can be employed. Also a substituted or unsubstituted benzothieno[3,2-f]indol-1-yl group can be employed. Also a substituted or unsubstituted benzothieno[2,3-g]indol-1-yl group can be employed. Also a substituted or unsubstituted benzothieno[3,2-g]indol-1-yl group can be employed. The fused ring constituting these groups may or may not be further fused with another ring.

In the present invention, a substituted or unsubstituted benzothieno[2,3-a]carbazol-9-yl group can be employed as the benzothiophene-fused indol-1-yl group. Also a substituted or unsubstituted benzothieno[3,2-a]carbazol-9-yl group can be employed. Also a substituted or unsubstituted benzothieno[2,3-b]carbazol-9-yl group can be employed. Also a substituted or unsubstituted benzothieno[3,2-b]carbazol-9-yl group can be employed. Also a substituted or unsubstituted benzothieno[2,3-c]carbazol-9-yl group can be employed. Also a substituted or unsubstituted benzothieno[3,2-c]carbazol-9-yl group can be employed. The fused ring constituting these groups may or may not be further fused with another ring.

Preferred examples of the benzothiophene-fused indol-1-yl group include groups having any of the following structures, in which a hydrogen atom in the following structure may or may not be substituted, for example, those substituted with an aryl group such as a phenyl group or substituted at the 3-position of a carbazole ring can be preferably exemplified. Further, the benzene ring in the following structure may be further fused with a ring or may not be fused with a ring,

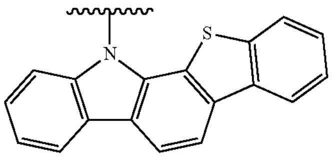

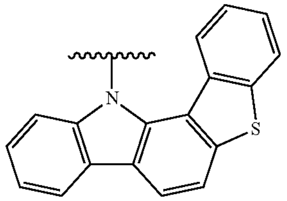

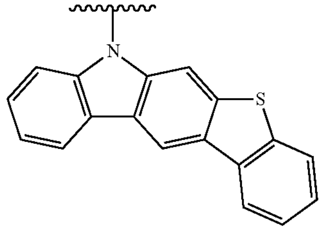

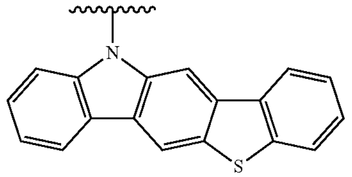

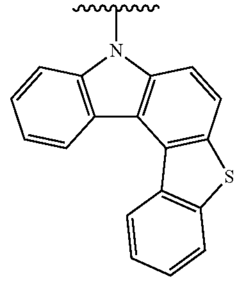

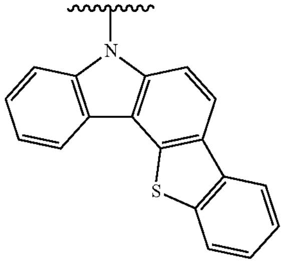

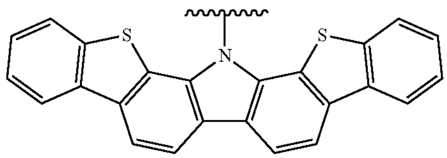

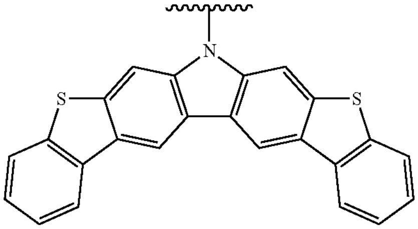

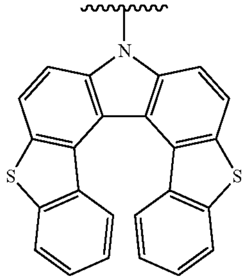

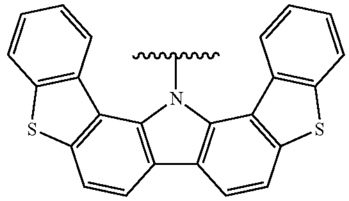

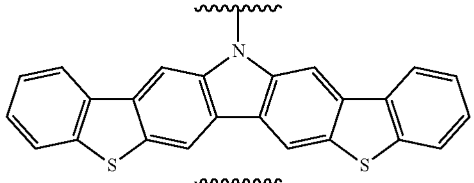

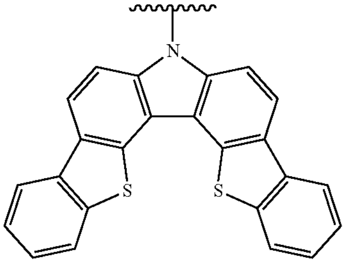

It is also possible to employ a carbazol-9-yl group in which two benzothiophene rings are fused at its 2- and 3-positions. Specifically, it is a group having any one of the following structures, and a hydrogen atom in the following structure may or may not be substituted. Further, the benzene ring in the following structure may be further fused with a ring or may not be fused with a ring.

In the present invention, a substituted or unsubstituted indolo[2,3-e]indol-1-yl group can be employed as the indole-fused indol-1-yl group. Also a substituted or unsubstituted indolo[3,2-e]indol-1-yl group can be employed. Also a substituted or unsubstituted indolo[2,3-f]indol-1-yl group can be employed. Also a substituted or unsubstituted indolo[3,2-f]indol-1-yl group can be employed. Also a substituted or unsubstituted indolo[2,3-g]indol-1-yl group can be employed. Also a substituted or unsubstituted indolo[3,2-g]indol-1-yl group can be employed. The fused ring constituting these groups may or may not be further fused with another ring.

In the present invention, a substituted or unsubstituted indolo[2,3-a]carbazol-9-yl group can be employed as the indole-fused indol-1-yl group. Also a substituted or unsubstituted indolo[3,2-a]carbazol-9-yl group can be employed.

Also a substituted or unsubstituted indolo[2,3-b]carbazol-9-yl group can be employed. Also a substituted or unsubstituted indolo[3,2-b]carbazol-9-yl group can be employed. Also a substituted or unsubstituted indolo[2,3-c]carbazol-9-yl group can be employed. Also a substituted or unsubstituted indolo[3,2-c]carbazol-9-yl group can be employed. The fused ring constituting these groups may or may not be further fused with another ring.

Preferred examples of the indole-fused indol-1-yl group include groups having any of the following structures, in which a hydrogen atom in the following structure may or may not be substituted, for example, those substituted with an aryl group such as a phenyl group or substituted at the 3-position of a carbazole ring can be preferably exemplified. Further, the benzene ring in the following structure may be further fused with a ring or may not be fused with a ring,

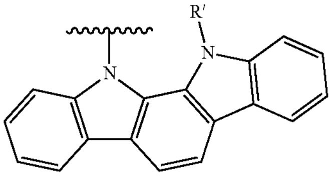

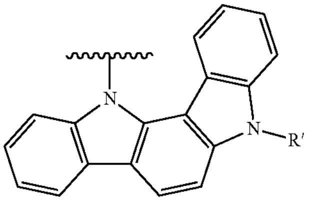

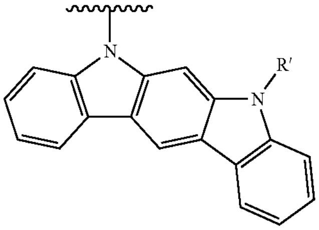

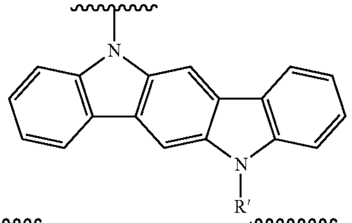

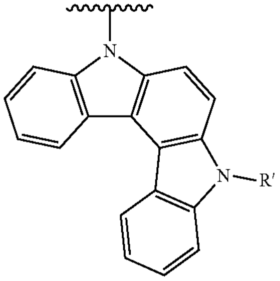

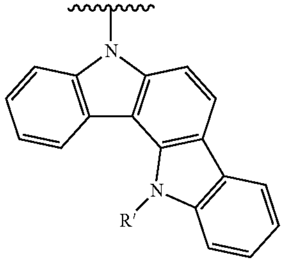

In a preferred aspect of the present invention, the benzofuran-fused indol-1-yl group, the benzothiophene-fused indol-1-yl group, the indole-fused indol-1-yl group and the silaindene-fused indol-1-yl group are substituted by a substituted or unsubstituted aryl group. Preferably, they are substituted by a substituted or unsubstituted phenyl group. As the substituent of the aryl group or the phenyl group, a group selected from any group of Substituent Group A to Substituent Group E can be selected, and the substituent can be preferably selected from Substituent Group E. In addition, it is also preferable that the aryl group or the phenyl group mentioned here is unsubstituted. In a preferred aspect of the present invention, the ring-fused indol-1-yl group is a benzofuran-fused indol-1-yl group substituted with a substituted or unsubstituted aryl group.

Specific examples of the IDL group which can be employed in the general formula (1) are shown below. However, the IDL group which can be employed in the present invention shall not be construed as being limited by the following specific examples. In the following specific examples, D represents a deuterium atom, and * represents a bonding site. In addition, the methyl group is not shown. Thus, for example, D199 represents a 3-methylcarbazol-9-yl group.

D1

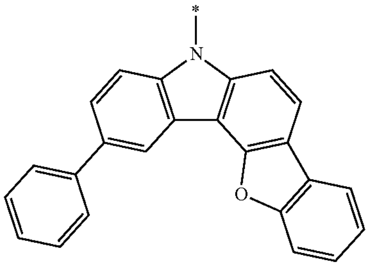

D2

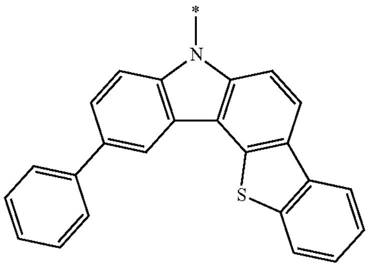

D3

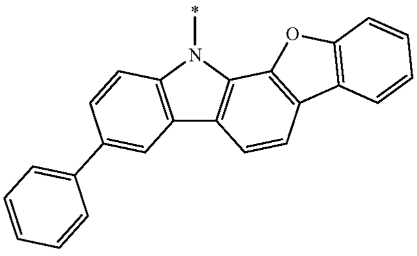

D4

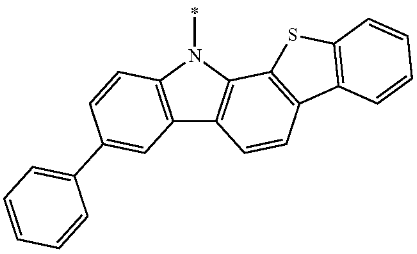

-continued
D5
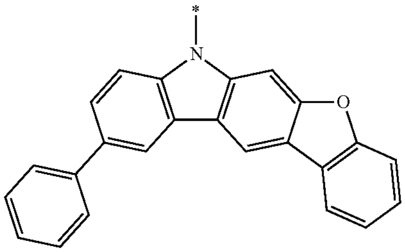
D6
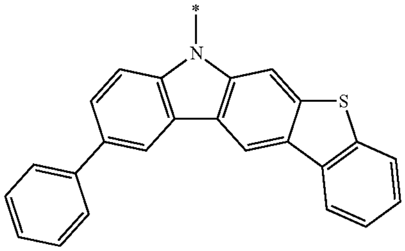
D7
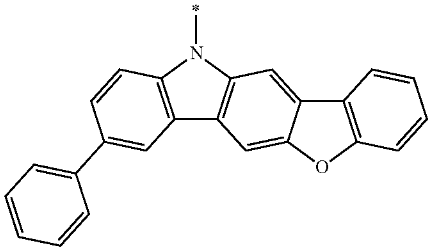
D8
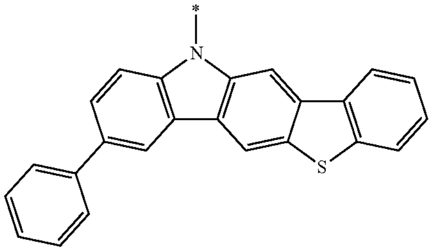
D9
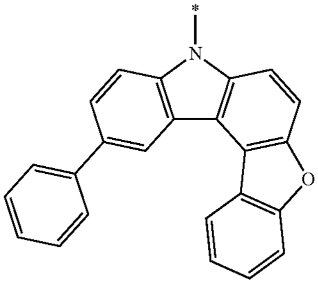
D10
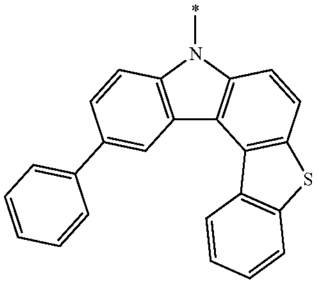
-continued
D11
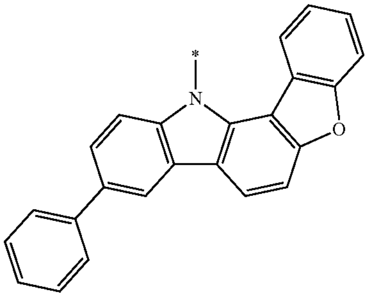
D12
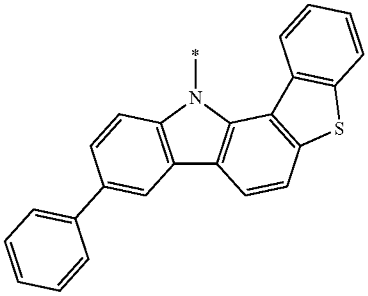
D13
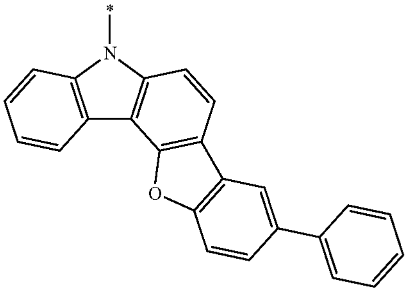
D14
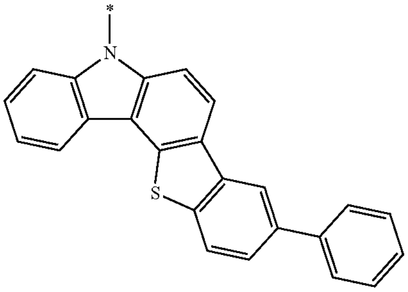
D15
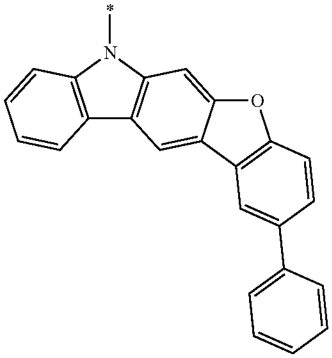

-continued
D16
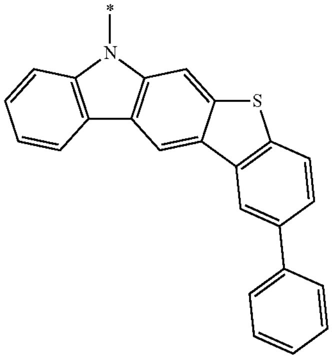
D17
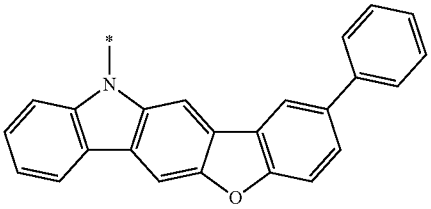
D18
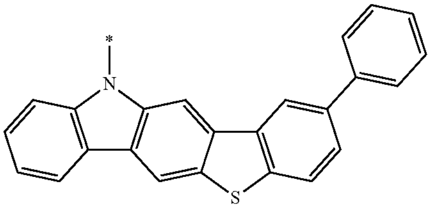
D19
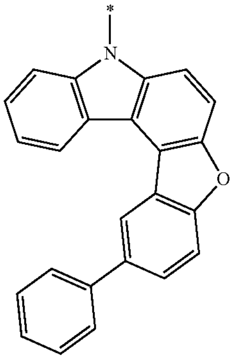
D20
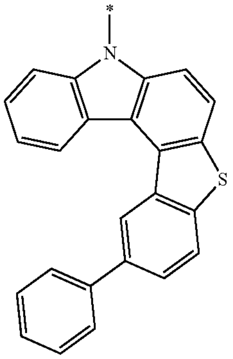
-continued
D21
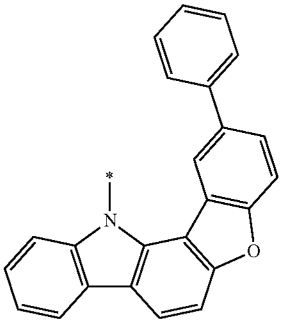
D22
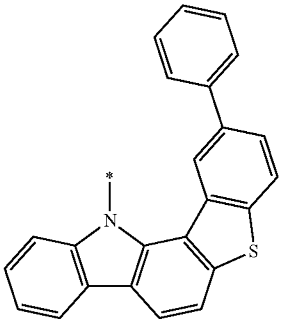
D23
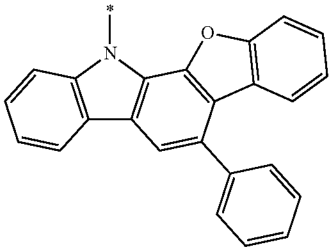
D24
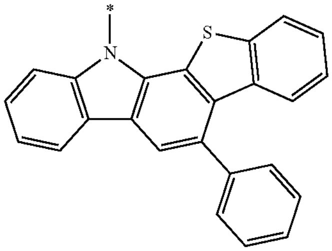
D25
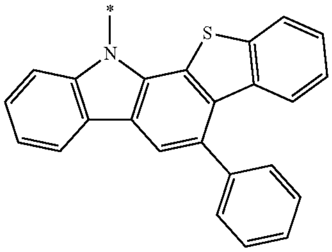

-continued
D26
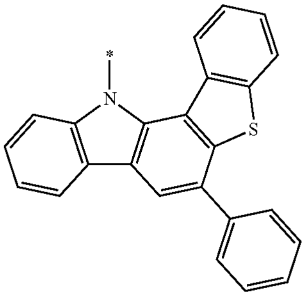
D27
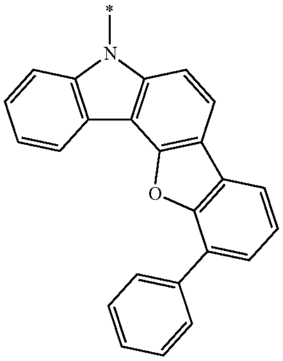
D28
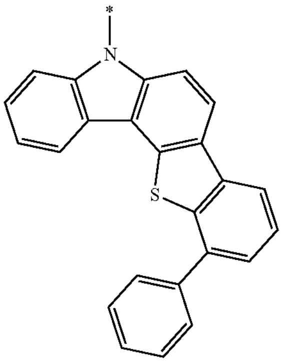
D29
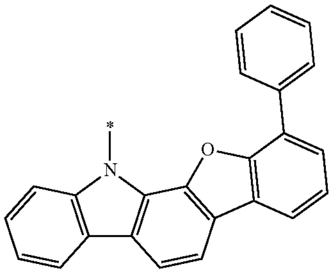
D30
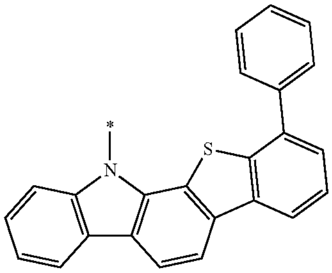
-continued
D31
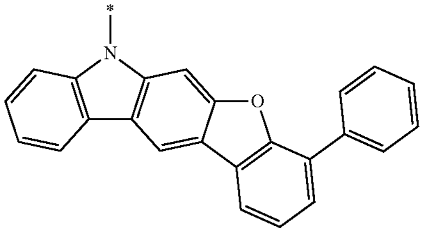
D32
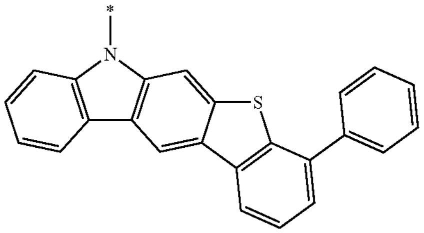
D33
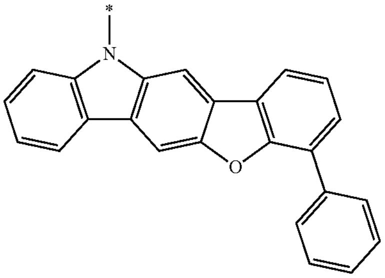
D34
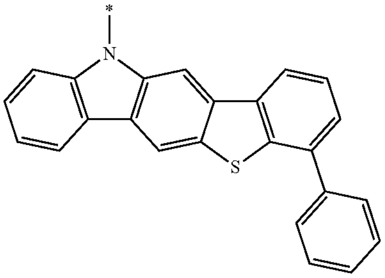
D35
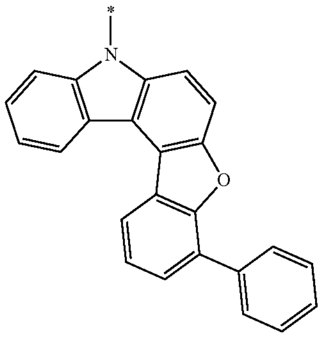

-continued
D36
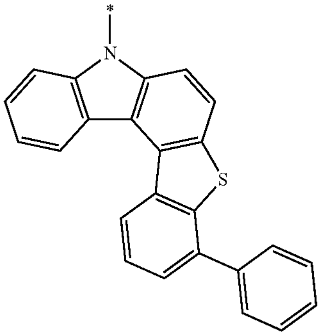
D37
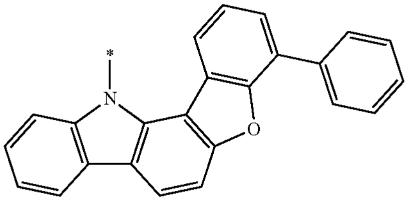
D38
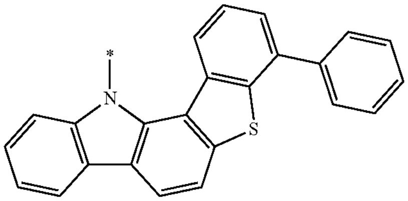
D39
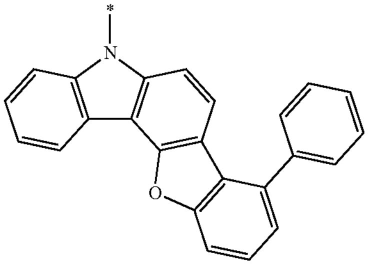
D40
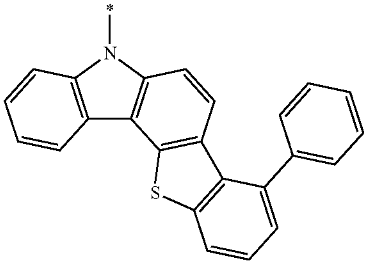
D41
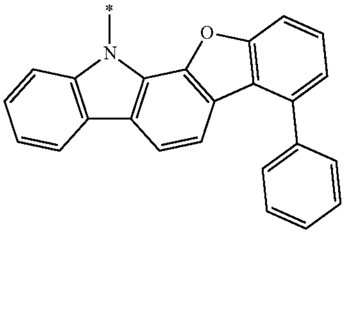
-continued
D42
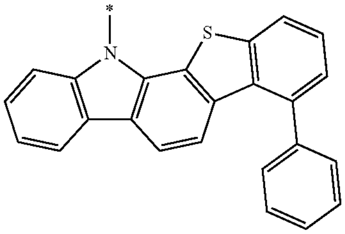
D43
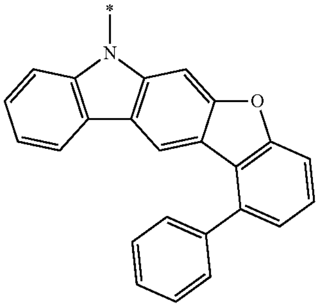
D44
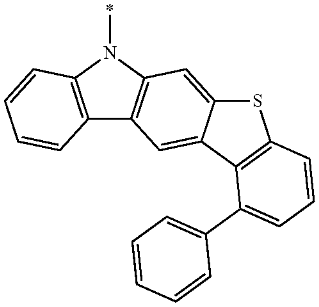
D45
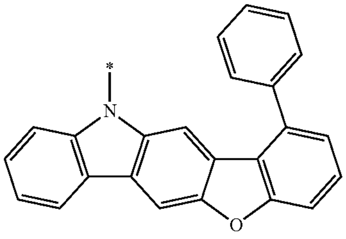
D46
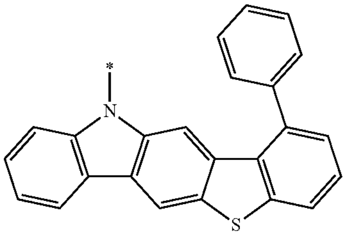
D47
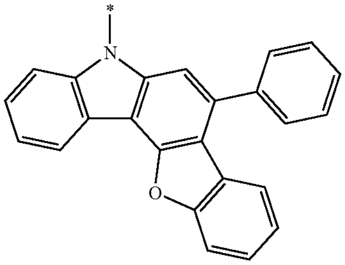

-continued
D48
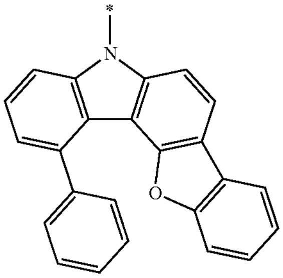
D49
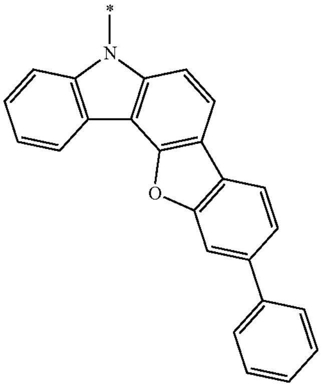
D50
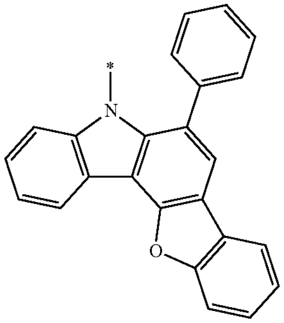
D51
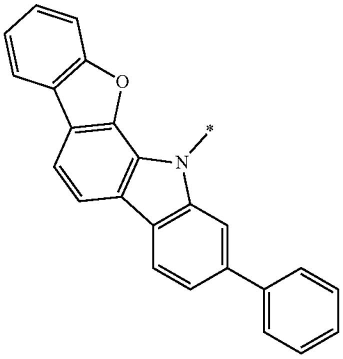
D52
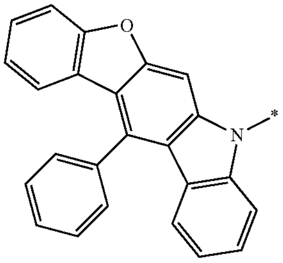
-continued
D53
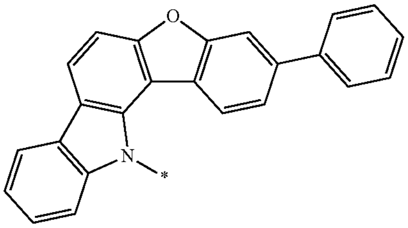
D54
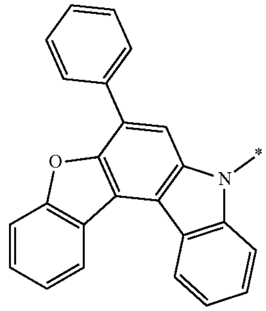
D55
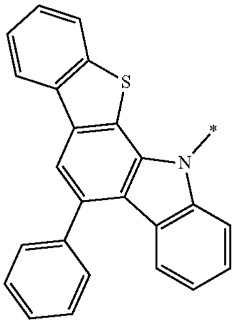
D56
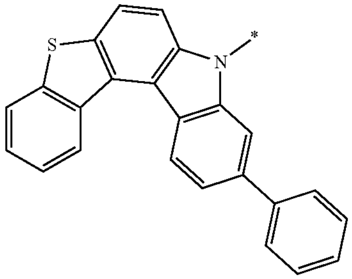
D57
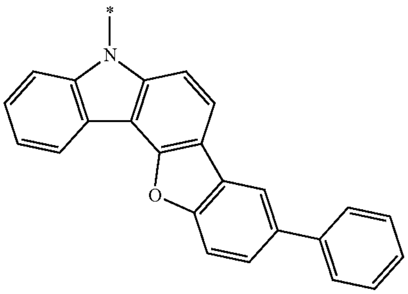

-continued
D58
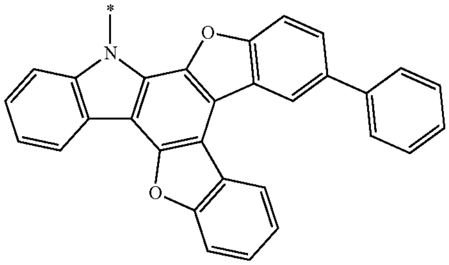
D59
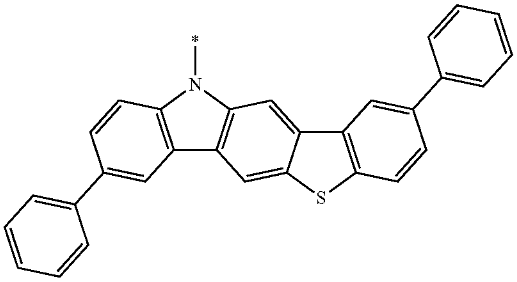
D60
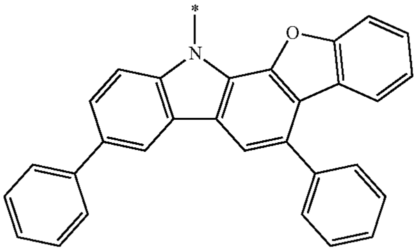
D61
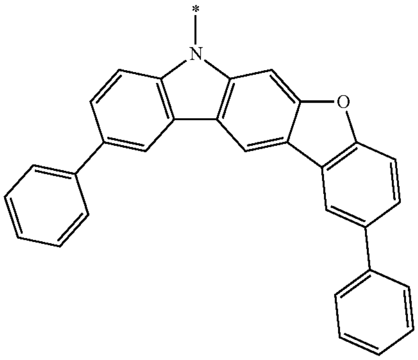
D62
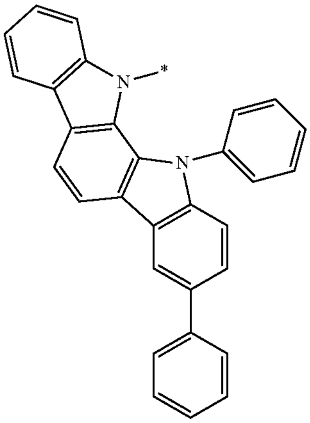
-continued
D63
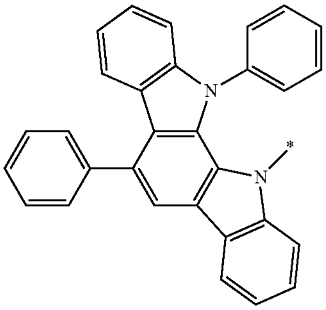
D64
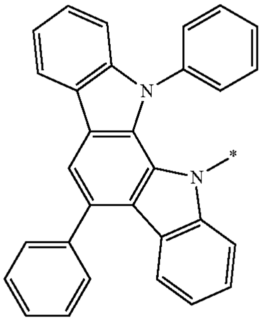
D65
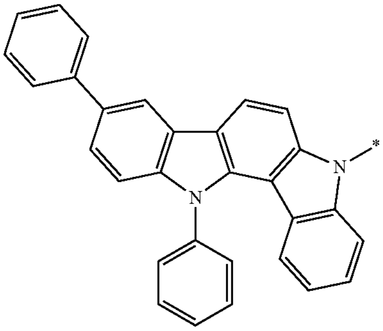
D66
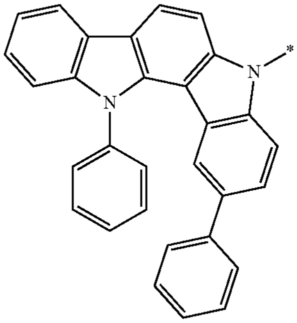

-continued
D67
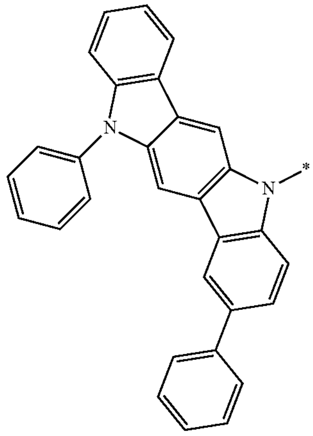
D68
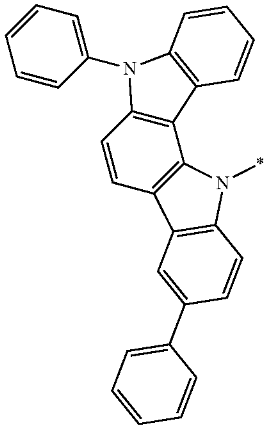
D69
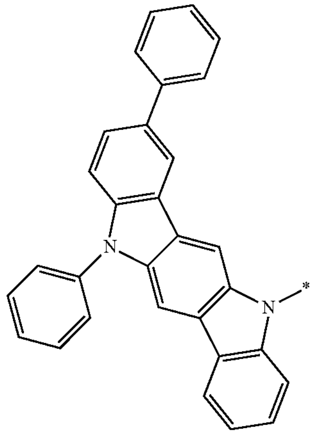
D70
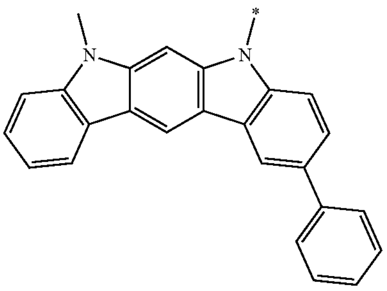
-continued
D71
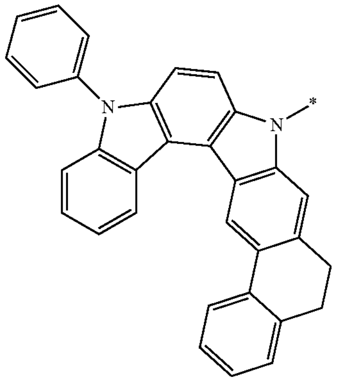
D72
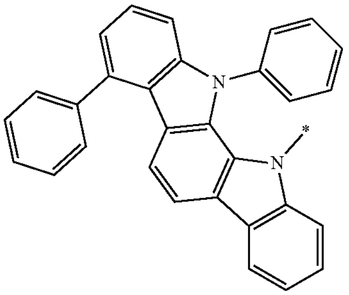
D73
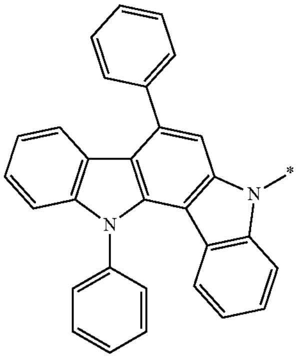
D74
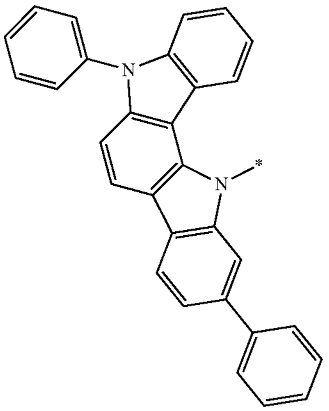

-continued
D75
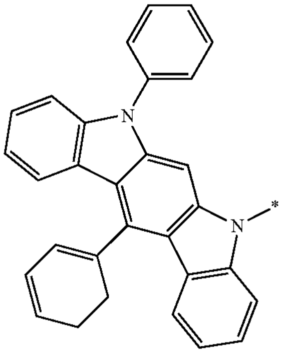
D76
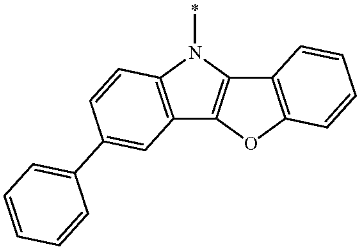
D77
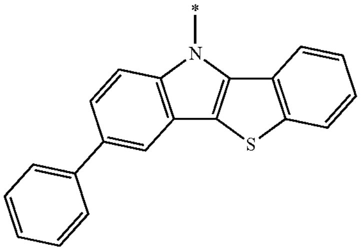
D78
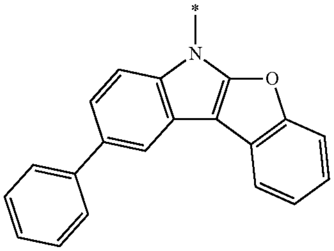
D79
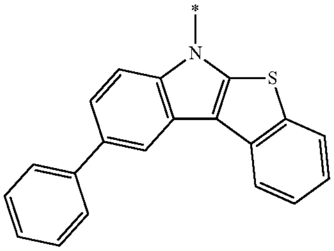
-continued
D80
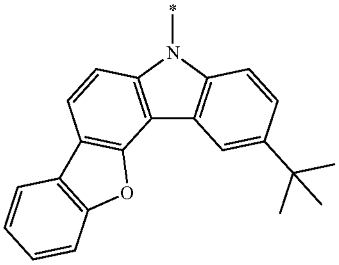
D81
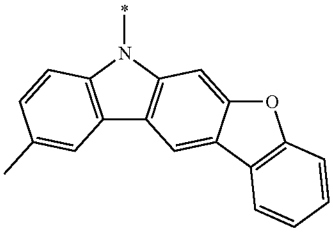
D82
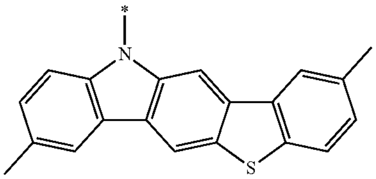
D83
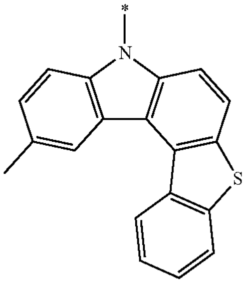
D84
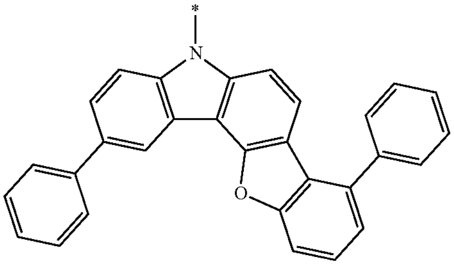
D85
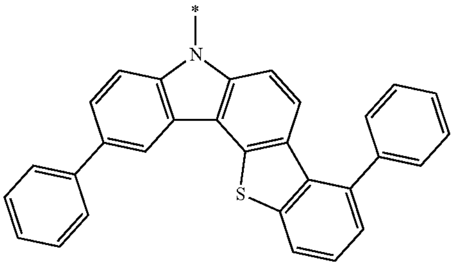

-continued
D86
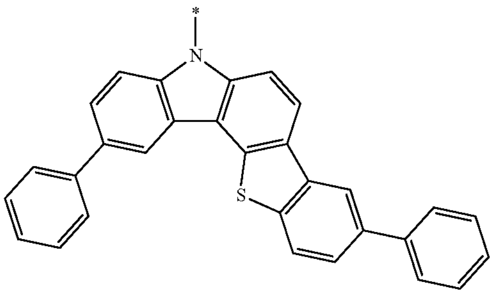
D87
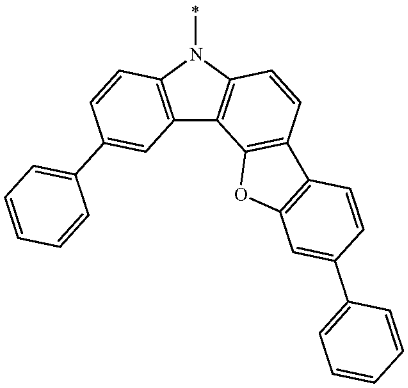
D88
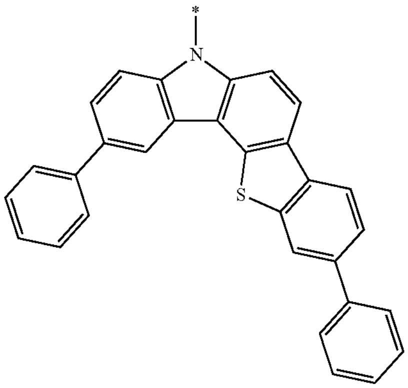
D89
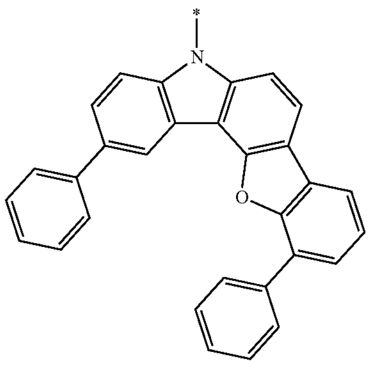
-continued
D90
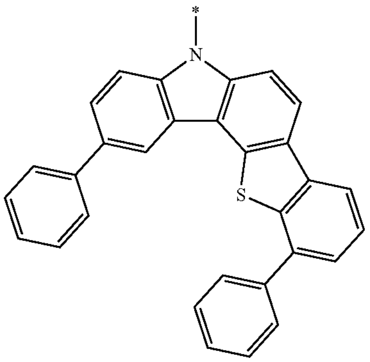
D91
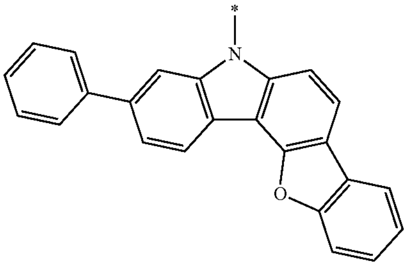
D92
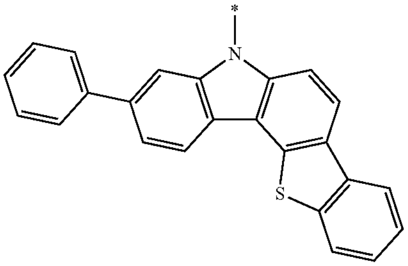
D93
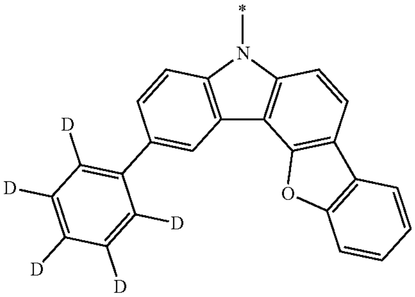
D94
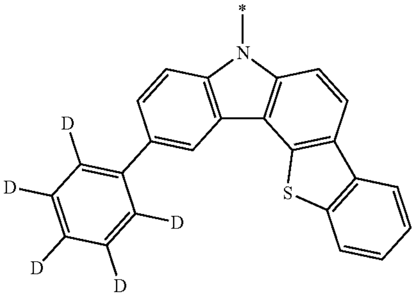

-continued
D95
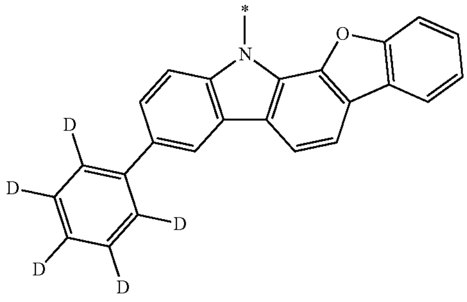
D96
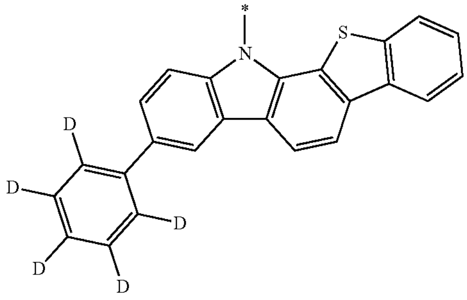
D97
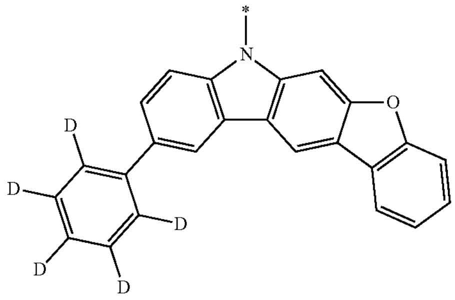
D98
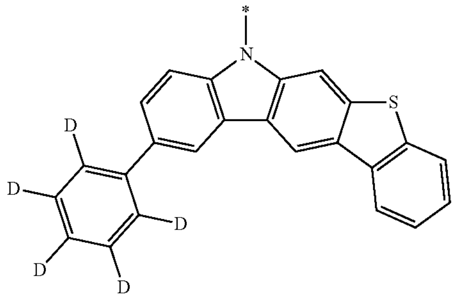
D99
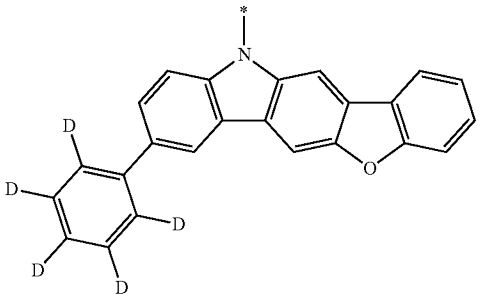
-continued
D100
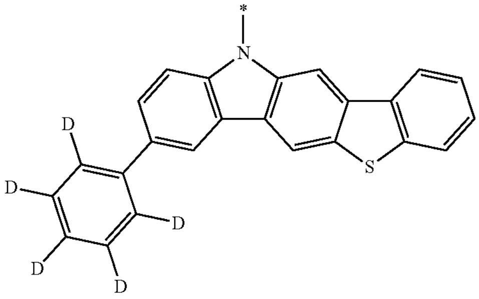
D101
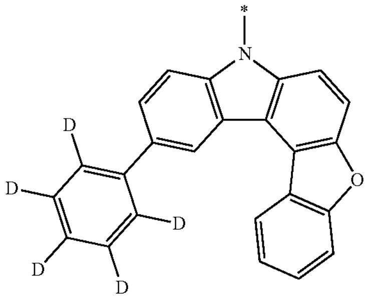
D102
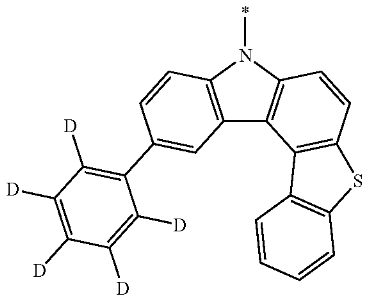
D103
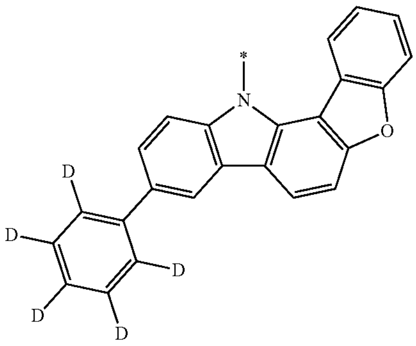
D104
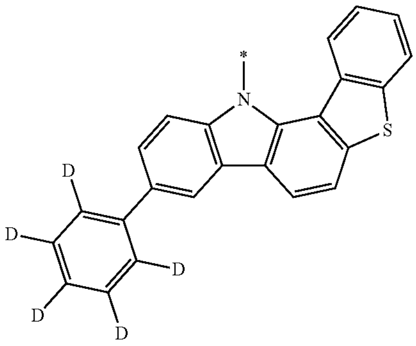

D105
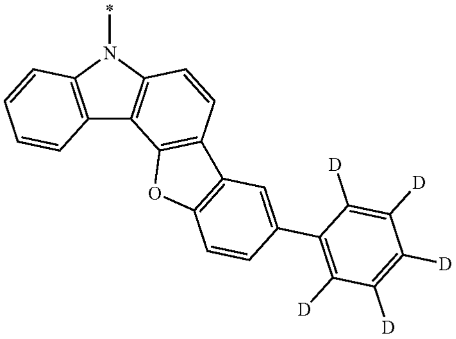
D106
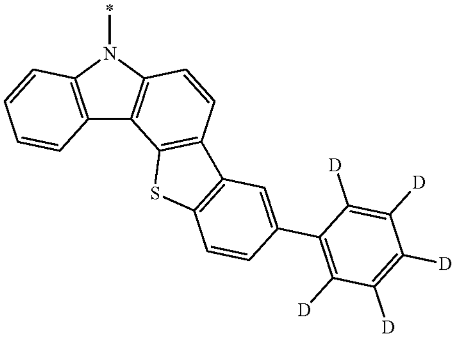
D107
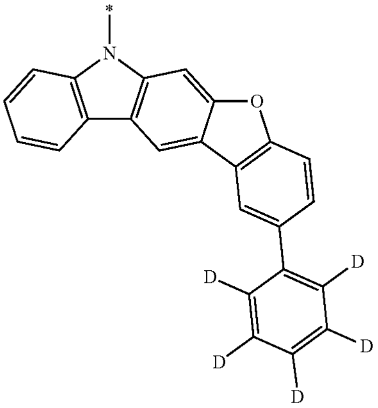
D108
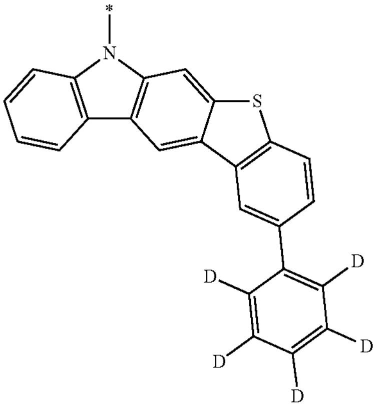
D109
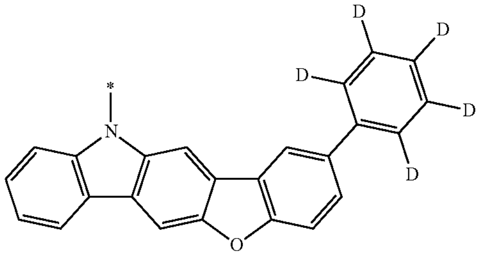
D110
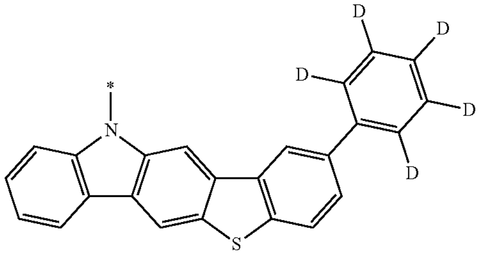
D111
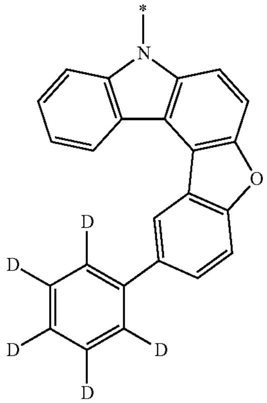
D112
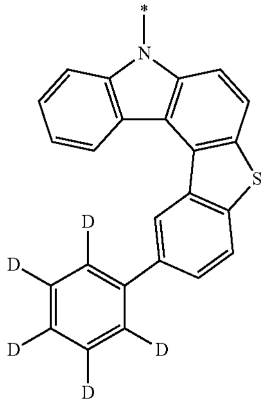

-continued
D113
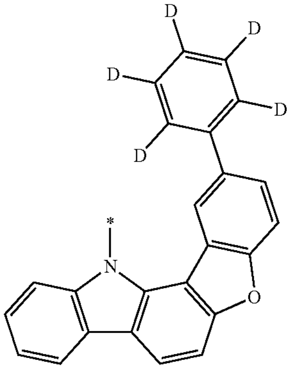
D114
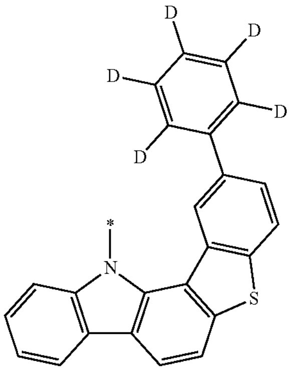
D115
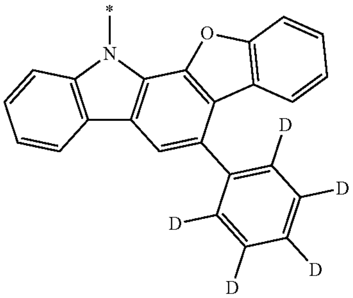
D116
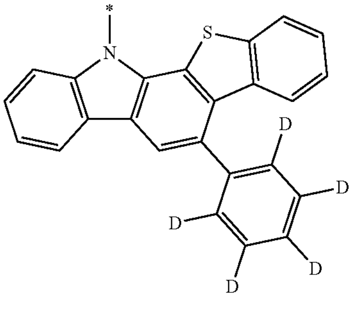
-continued
D117
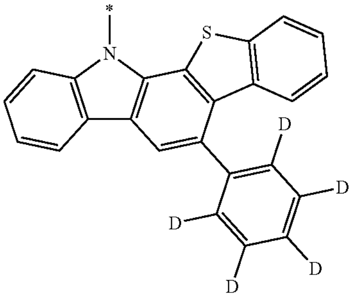
D118
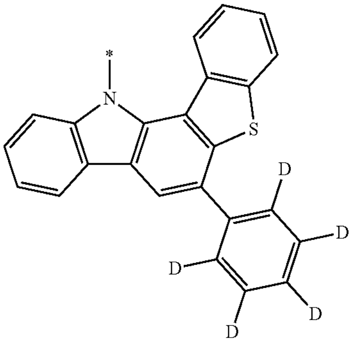
D119
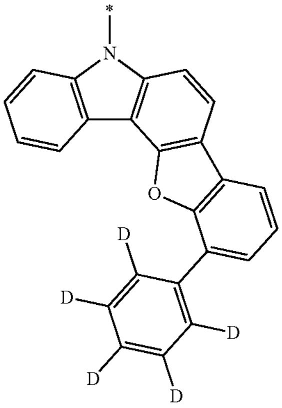
D120
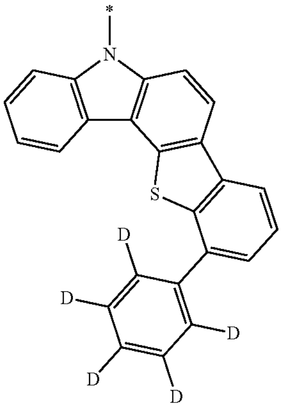

-continued
D121
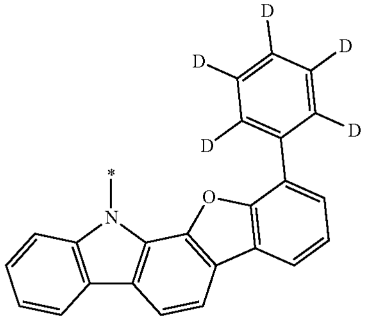
D122
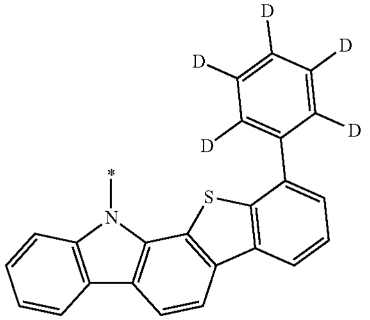
D123
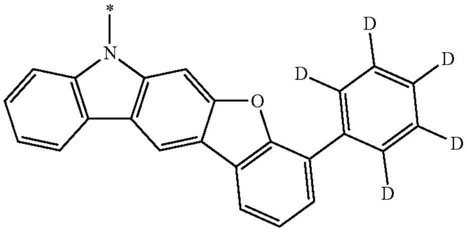
D124
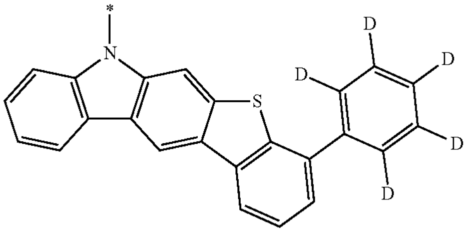
D125
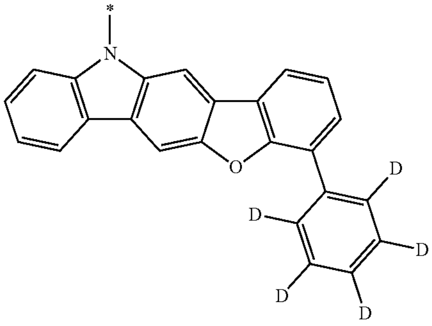
-continued
D126
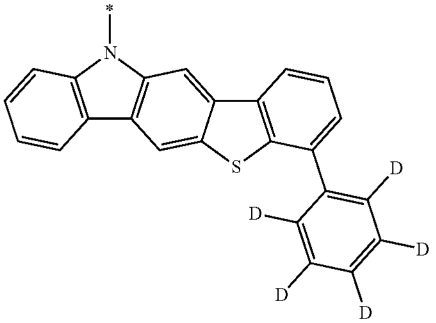
D127
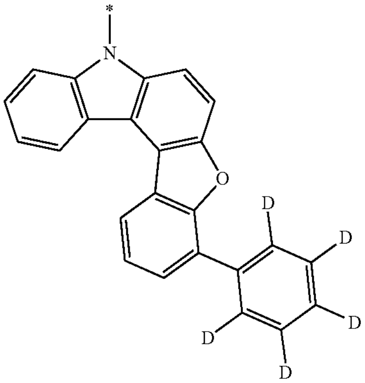
D128
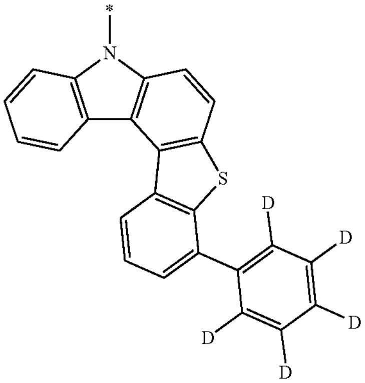
D129
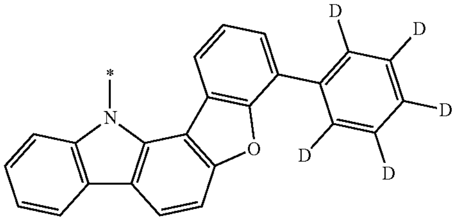
D130
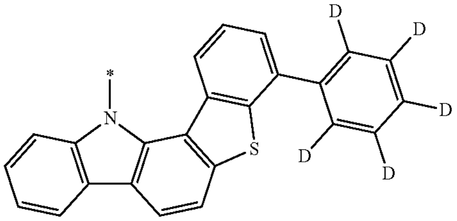

-continued
D131
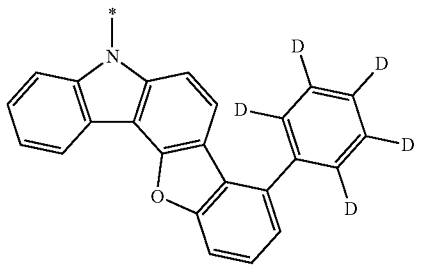
D132
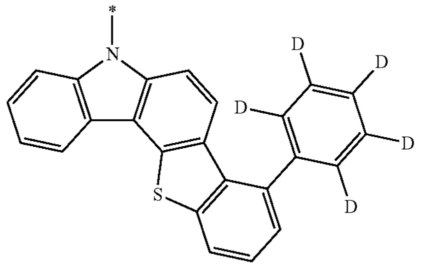
D133
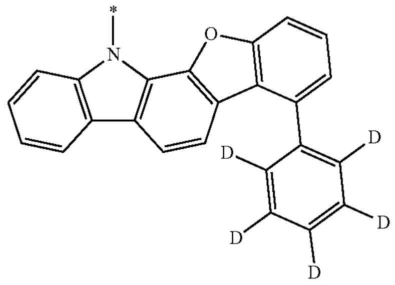
D134
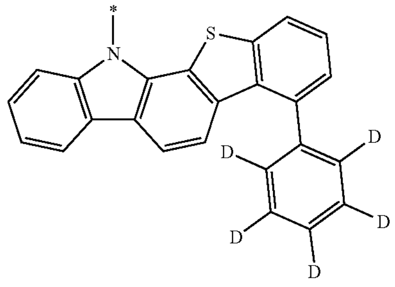
D135
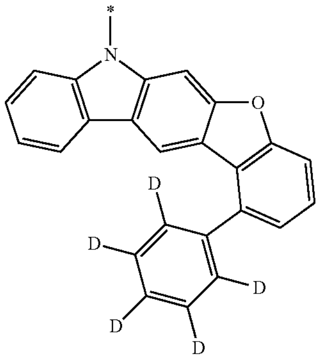
-continued
D136
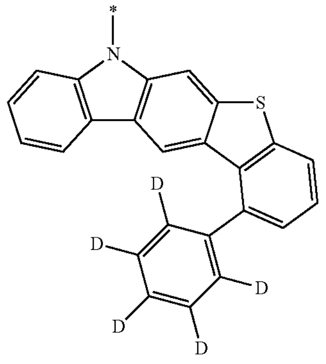
D137
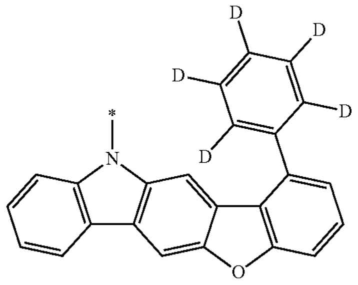
D138
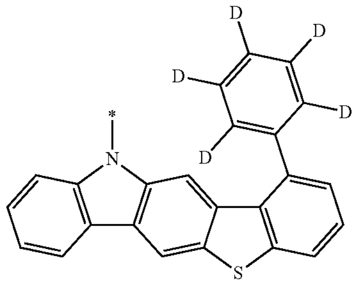
D139
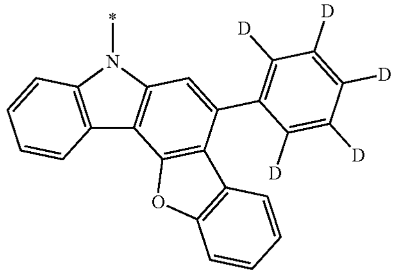
D140
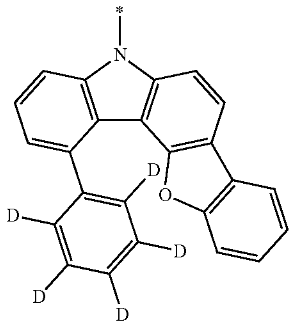

-continued
D141
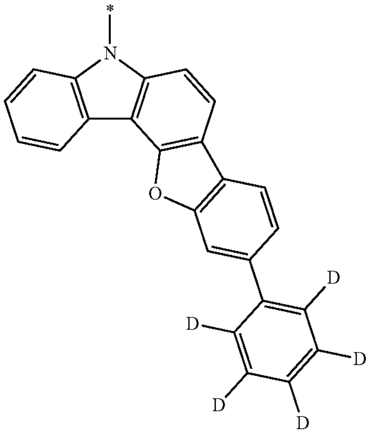
D142
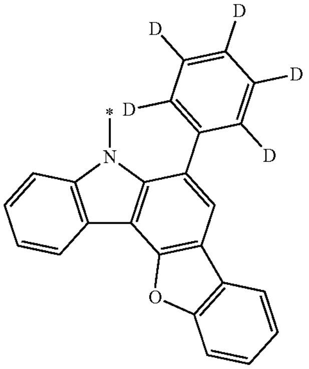
D143
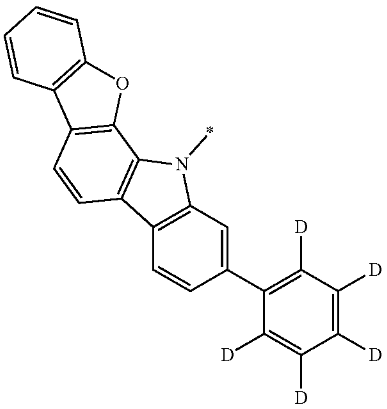
D144
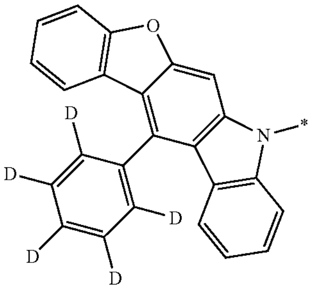
-continued
D145
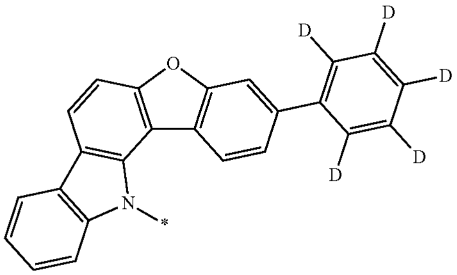
D146
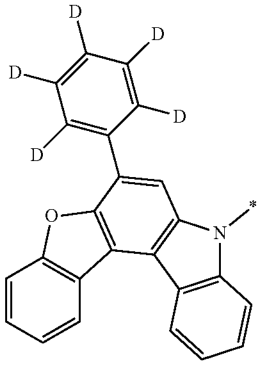
D147
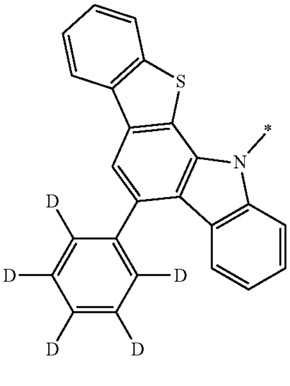
D148
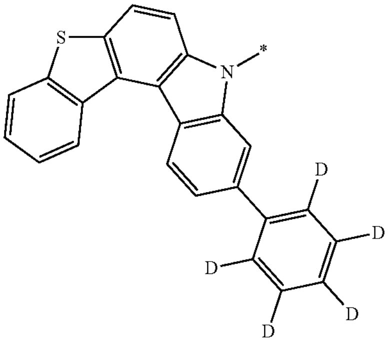

-continued
D149
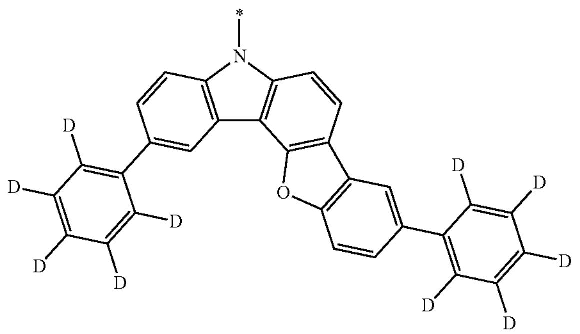
D150
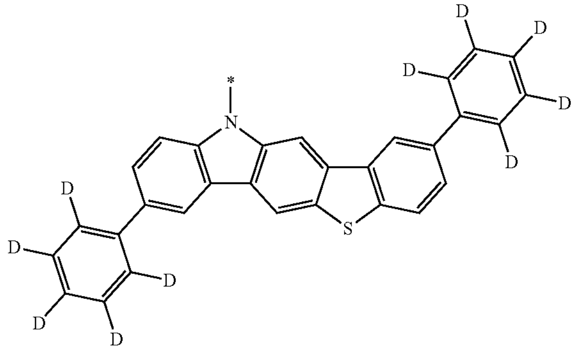
D151
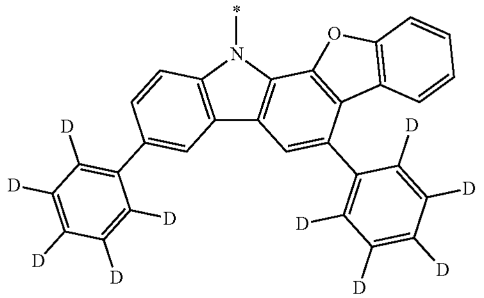
D152
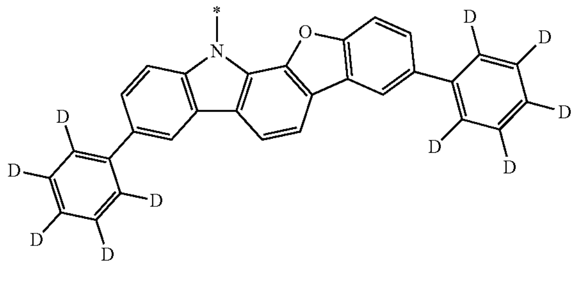
-continued
D153
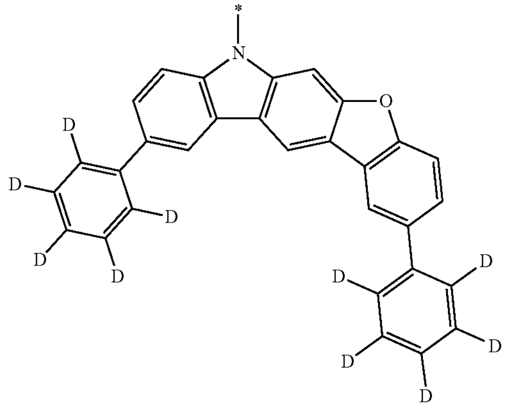
D154
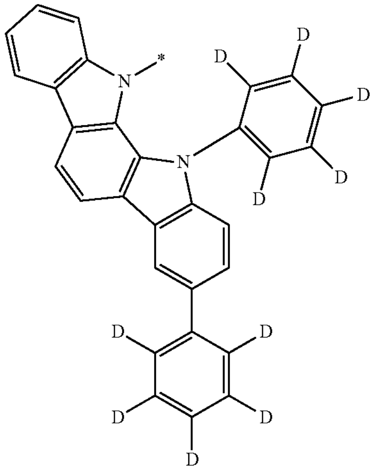
D155
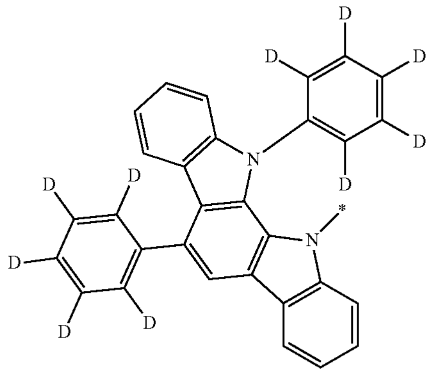

-continued
D156
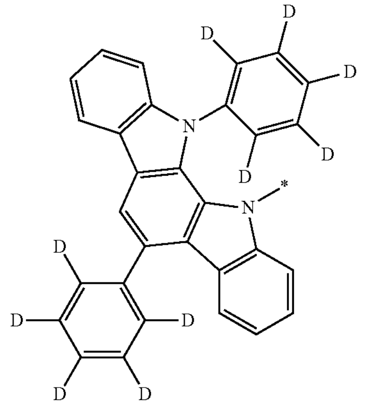
D157
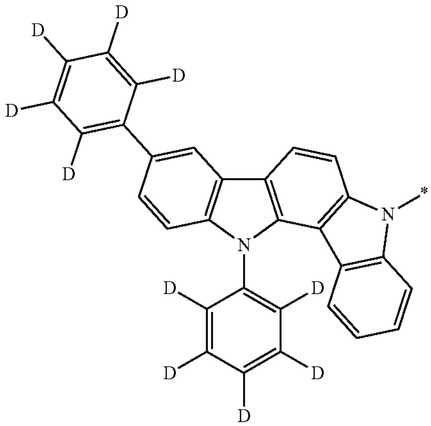
D158
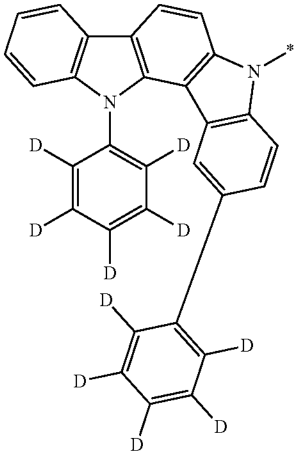
-continued
D159
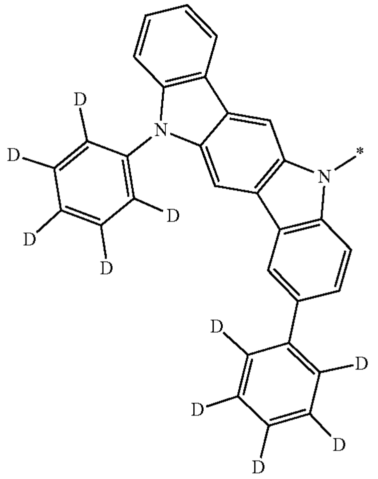
D160
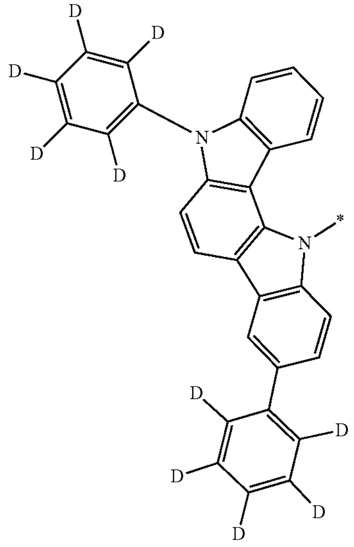
D161
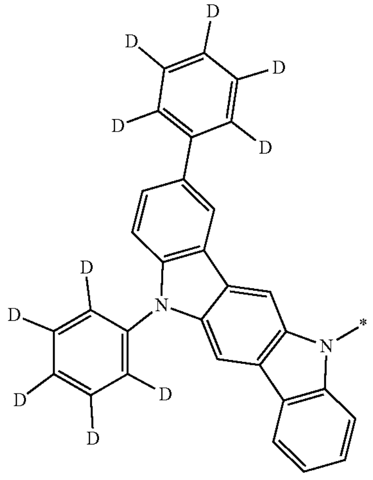

-continued
D162
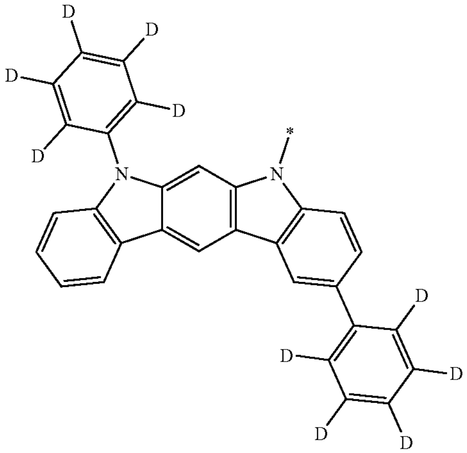
D163
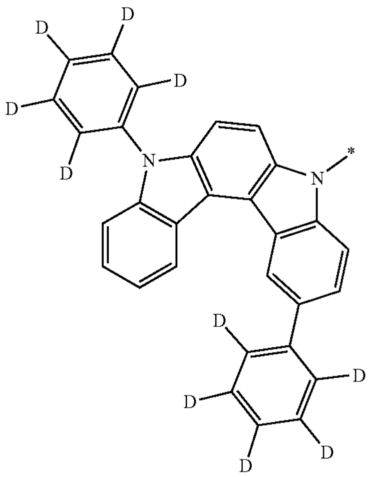
D164
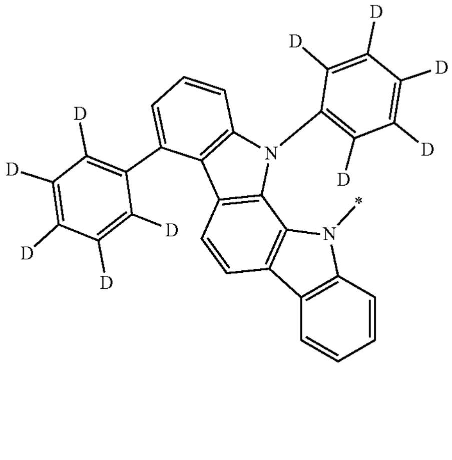
-continued
D165
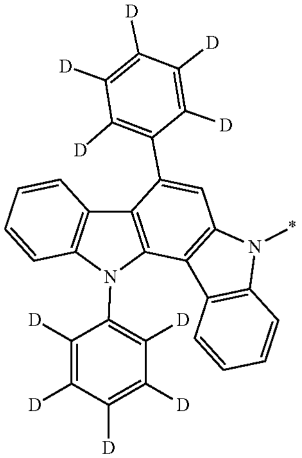
D166
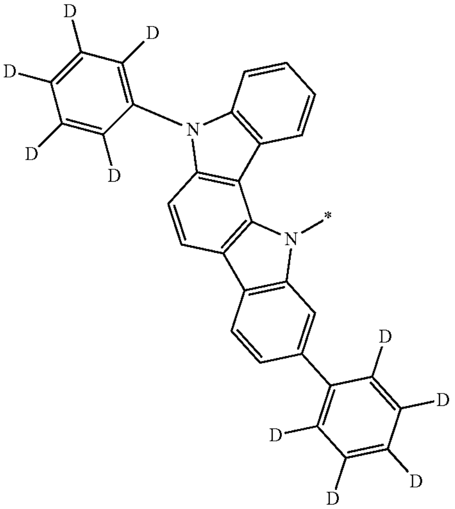
D167
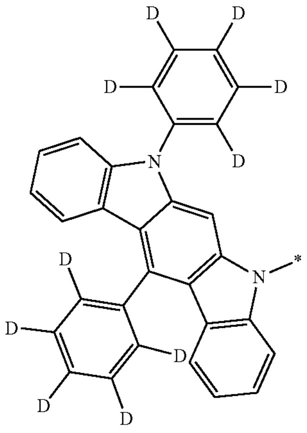

-continued
D168
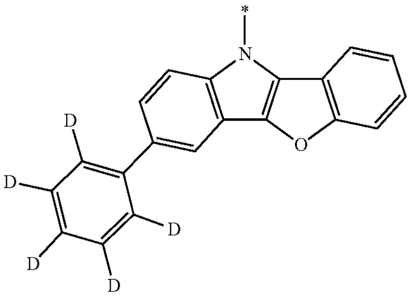
D169
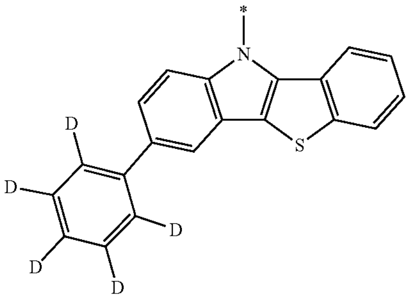
D170
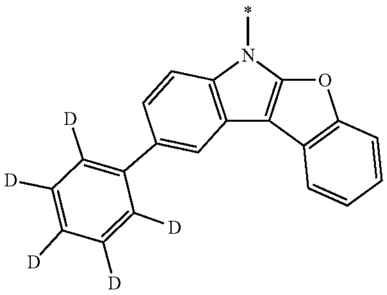
D171
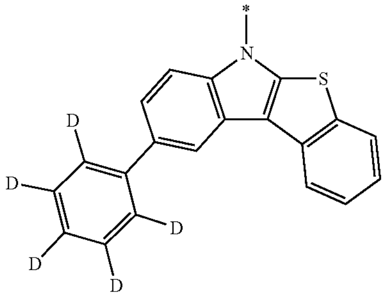
D172
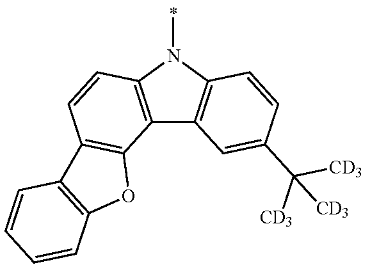
-continued
D173
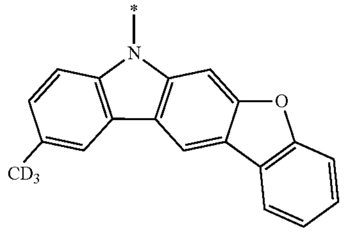
D174
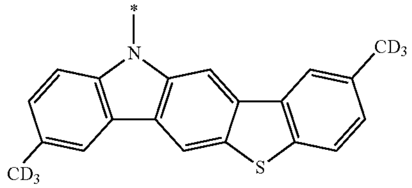
D175
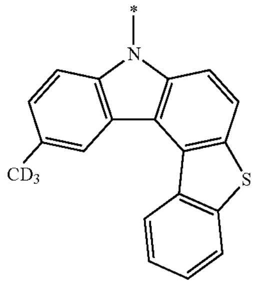
D176
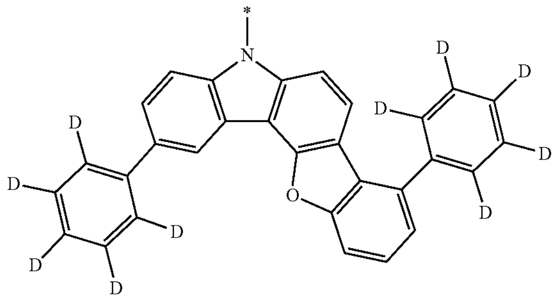
D177
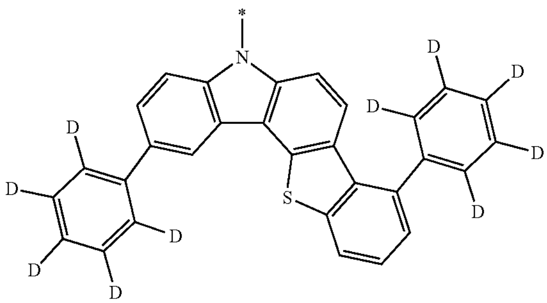

-continued
D178
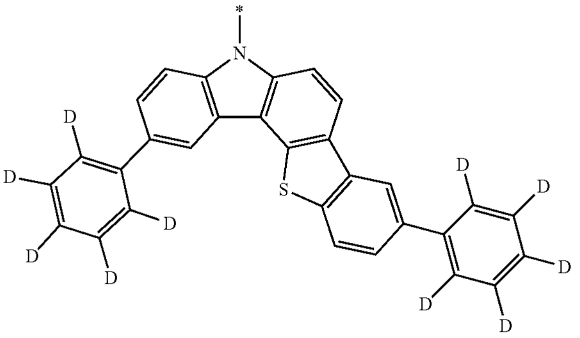
D179
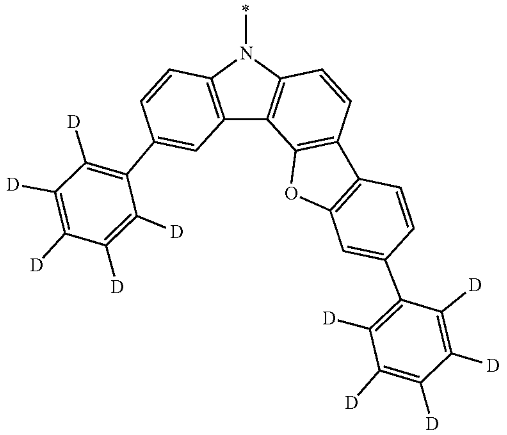
D180
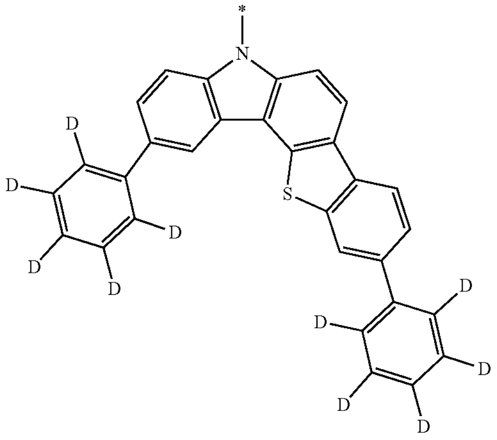
D181
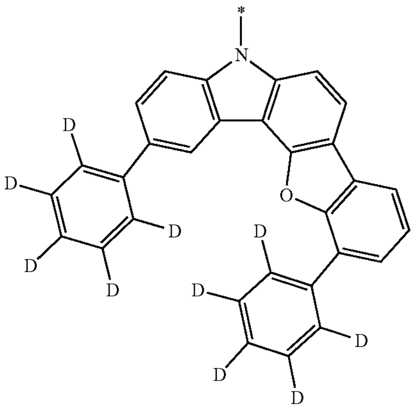
-continued
D182
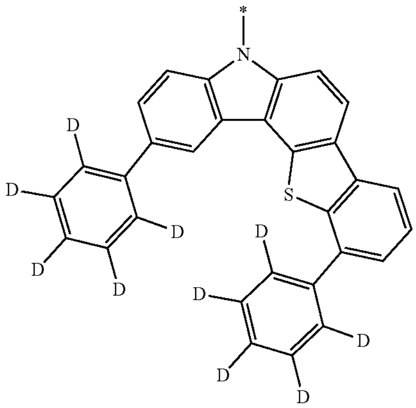
D183
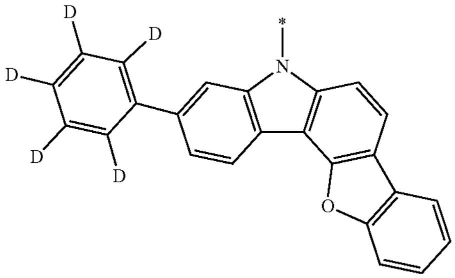
D184
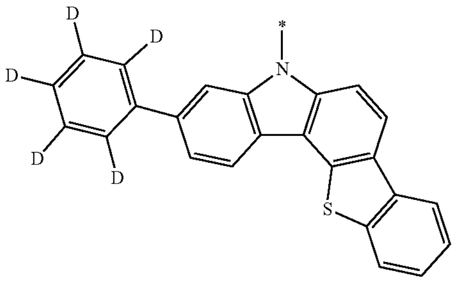
D185
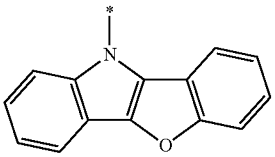
D186
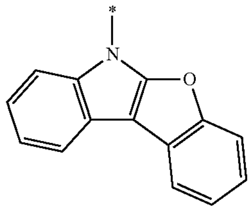
D187
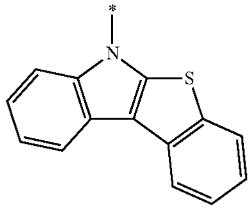

-continued
D188
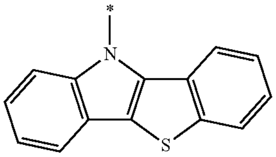
D189
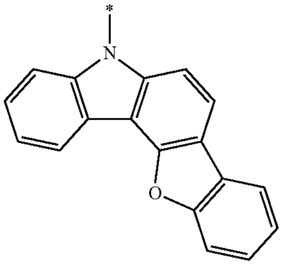
D190
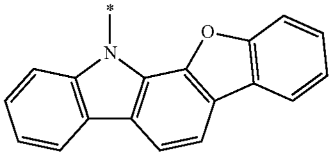
D191
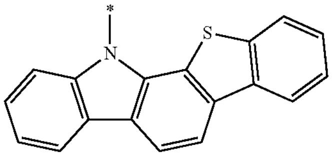
D192
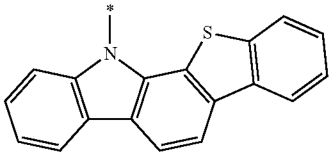
D193
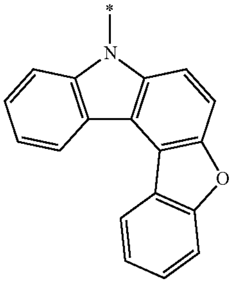
D194
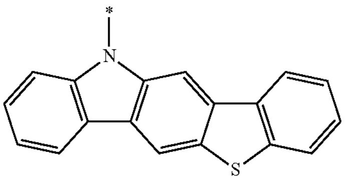
D195
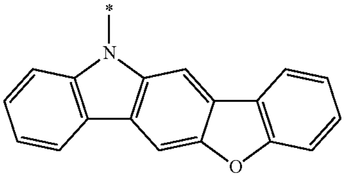
-continued
D196
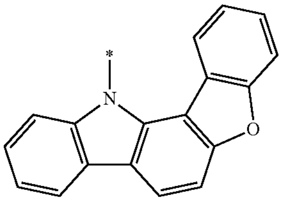
D197
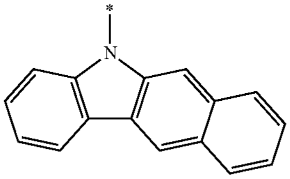
D198
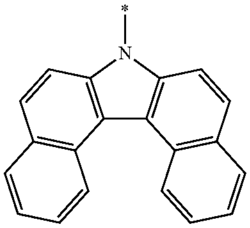
D199
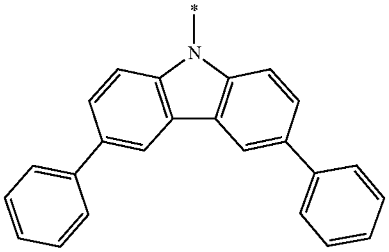
D200
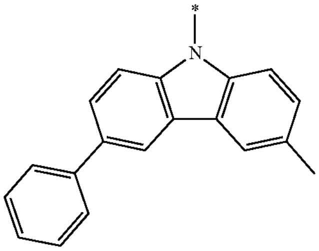
D201
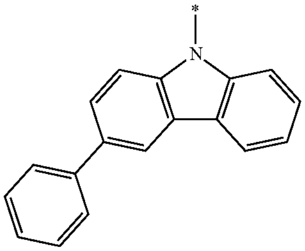
D202
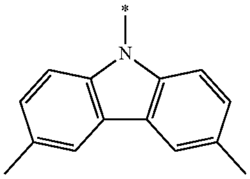

-continued

D203

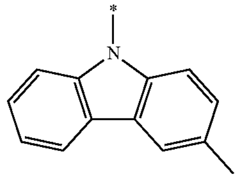

D204

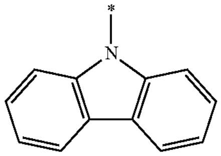

Among $R^1$ to $R^5$ in the general formula (1), groups which are not cyano groups, not substituted or unsubstituted aryl groups, not substituted or unsubstituted pyridyl groups, and not IDL groups (hereinafter referred to as "remaining $R^1$ to $R^5$") are hydrogen atoms, deuterium atoms, or substituents which are not cyano groups, not aryl groups, not pyridyl groups, and not IDL groups (hereinafter referred to as "remaining substituents"). The remaining $R^1$ to $R^5$ may be all hydrogen atoms or deuterium atoms, for example, all may be hydrogen atoms, or for example, all may be deuterium atoms. The number of the remaining substituents among the remaining $R^1$ to $R^5$ is 0 to 3, for example, may be 2 or 3, or may be 0 or 1.

The remaining substituents may be selected from Substituent Group A which will be described later, may be selected from Substituent Group B which will be described later, may be selected from Substituent Group C which will be described later, may be selected from Substituent Group D which will be described later, or may be selected from Substituent Group E which will be described later.

In one aspect of the present invention, the remaining substituents include a donor group. In one aspect of the present invention, the remaining substituents are all donor groups. In particular, when the number of the remaining substituents is 3, at least one is a donor group. The donor group as referred to herein can be selected from groups having a negative Hammett's σp value. The Hammett's σp value is proposed by L. P. Hammett and quantifies the influence of a substituent on the reaction rate or equilibrium of a para-substituted benzene derivative. Specifically, the value is a constant (σp) peculiar to the substituent in the following equation that is established between a substituent and a reaction rate constant or an equilibrium constant in a para-substituted benzene derivative:

$$\log(k/k_0)=p\sigma p$$

or $$\log(K/K_0)=p\sigma p$$

In the above equations, $k_0$ represents a rate constant of a benzene derivative not having a substituent; k represents a rate constant of a benzene derivative substituted with a substituent; $K_0$ represents an equilibrium constant of a benzene derivative not having a substituent; K represents an equilibrium constant of a benzene derivative substituted with a substituent; and ρ represents a reaction constant to be determined by the kind and the condition of reaction. Regarding the description relating to the "Hammett's σp value" and the numerical value of each substituent in the present invention, reference may be made to the description relating to up value in Hansch, C. et. al., Chem. Rev., 91, 165-195 (1991).

In one aspect of the present invention, the remaining substituents are all unsubstituted ring-fused indol-1-yl groups. In one aspect of the present invention, the remaining substituents are all unsubstituted carbazol-9-yl groups. The unsubstituted carbazol-9-yl group as referred to herein may be an unsubstituted fused carbazol-9-yl group. In one aspect of the present invention, at least one of $R^1$ to $R^5$ is a substituted fused carbazol-9-yl group, and at least one is an unsubstituted fused carbazol-9-yl group. In one aspect of the present invention, at least two of $R^1$ to $R^5$ are substituted fused carbazol-9-yl groups, and at least one of $R^1$ to $R^5$ is an unsubstituted fused carbazol-9-yl group. In one aspect of the present invention, at least one of $R^1$ to $R^5$ is a substituted fused carbazol-9-yl group, and at least two of $R^1$ to $R^5$ are unsubstituted fused carbazol-9-yl groups. In one aspect of the present invention, two of $R^1$ to $R^5$ are substituted fused carbazol-9-yl groups, and two of $R^1$ to $R^5$ are unsubstituted fused carbazol-9-yl groups.

In one aspect of the present invention, $R^1$ to $R^5$ are each independently a substituted or unsubstituted aryl group or a substituted or unsubstituted ring-fused indol-1-yl group. For example, $R^1$ and $R^5$ are an unsubstituted ring-fused indol-1-yl group, R is a substituted ring-fused indol-1-yl group, $R^4$ is a substituted or unsubstituted ring-fused indol-1-yl group, and $R^3$ is a substituted or unsubstituted aryl group. For example, $R^1$ and $R^5$ are an unsubstituted ring-fused indol-1-yl group, $R^2$ and $R^4$ are a substituted ring-fused indol-1-yl group, and $R^3$ is a substituted or unsubstituted aryl group. In one aspect of the present invention, $R^1$ to $R^5$ are each independently a substituted or unsubstituted aryl group or a substituted ring-fused indol-1-yl group.

In one aspect of the present invention, three to five groups among $R^1$ to $R^5$ in the general formula (1) are donor groups, and the remaining $R^1$ to $R^5$ represent a hydrogen atom, a deuterium atom, a substituted or unsubstituted alkyl group, or a substituted or unsubstituted aryl group. At least one of the donor groups represented by $R^1$ to $R^5$ is a fused carbazolyl group. In one aspect of the present invention, three or four groups among $R^1$ to $R^5$ in the general formula (1) are donor groups, one or two groups among $R^1$ to $R^5$ are substituted or unsubstituted aryl groups, and the remaining $R^1$ to $R^5$ are a hydrogen atom or a deuterium atom. Preferably, a part or all of the donor groups are substituted or unsubstituted carbazol-9-yl groups. In one aspect of the present invention, donor groups having structures different from each other are present in three to four donor groups. For example, substituted or unsubstituted ring-fused indol-1-yl groups having different structures from each other are present. For example, a substituted ring-fused indol-1-yl group and an unsubstituted ring-fused indol-1-yl group are present. More specifically, a case where carbazol-9-yl groups having different substitution states are present, and specifically, a substituted carbazolyl group and an unsubstituted carbazolyl group are mixed can be exemplified. For example, $R^1$ and $R^2$ may be donor groups having the same structure, and $R^4$ and $R^5$ may be donor groups having a structure different from that of $R^1$ and $R^2$. On the other hand, all of the three to four donor groups may have the same structure. In a preferred aspect of the present invention, $R^3$ is an aryl group or a pyridyl group. In one aspect of the present invention, the donor group which is employable by $R^1$ to $R^5$ has a structure represented by the following general formula (4). $R^{21}$ and $R^{22}$ each independently represent a substituted or unsubstituted alkyl group, a substituted or unsubstituted alkenyl group, a substituted or unsubstituted aryl group, or a substituted or unsubstituted heteroaryl group. $R^{21}$ and $R^{22}$ may be bonded to each other to form a cyclic structure. L represents a single bond, a substituted or unsubstituted arylene group, or a substituted or unsubstituted heteroarylene group, and * represents a bonding site to a carbon atom (C) constituting the ring skeleton of the ring in the general formula (1).

General formula (4)

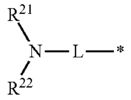

In the general formula (1), $R^1$ and $R^2$, $R^2$ and $R^1$, $R^3$ and $R^4$, or $R^4$ and $R^1$ may be bonded to each other to form a cyclic structure. For the description and specific examples of the cyclic structure referred to herein, the description and specific examples of the fused ring in the description of the above-mentioned "ring-fused" can be referred to.

In one aspect of the present invention, at least one pair of $R^1$ and $R^2$ or $R^4$ and $R^5$ is bonded to each other to form a cyclic structure. In one aspect of the present invention, at least one pair of $R^2$ and $R^3$ or $R^3$ and $R^4$ is bonded to each other to form a cyclic structure. In one aspect of the present invention, none of $R^1$ and $R^2$, or $R^4$ and $R^5$ is bonded to each other to form a cyclic structure. In one aspect of the present invention, none of $R^2$ and $R^3$, or $R^3$ and $R^4$ is bonded to each other to form a cyclic structure. In one aspect of the present invention, none of $R^1$ and $R^2$, $R^2$ and $R^3$, $R^3$ and $R^4$, or $R^4$ and $R^5$ is bonded to each other to form a cyclic structure.

The compound represented by the general formula (1) preferably does not contain a metal atom, and may be a compound composed only of atoms selected from the group consisting of a carbon atom, a hydrogen atom, a deuterium atom, a nitrogen atom, an oxygen atom, and a sulfur atom. In a preferred aspect of the present invention, the compound represented by the general formula (1) is composed only of atoms selected from the group consisting of a carbon atom, a hydrogen atom, a deuterium atom, a nitrogen atom, and an oxygen atom. In addition, the compound represented by the general formula (1) may be a compound composed only of atoms selected from the group consisting of a carbon atom, a hydrogen atom, a deuterium atom, a nitrogen atom, and a sulfur atom. The compound represented by the general formula (1) may be a compound composed only of atoms selected from the group consisting of a carbon atom, a hydrogen atom, a deuterium atom, and a nitrogen atom. The compound represented by the general formula (1) may be a compound composed only of atoms selected from the group consisting of a carbon atom, a hydrogen atom, and a nitrogen atom. Further, the compound represented by the general formula (1) may be a compound which does not contain a hydrogen atom but contains a deuterium atom. For example, the compound represented by the general formula (1) may be a compound composed only of atoms selected from the group consisting of a carbon atom, a deuterium atom, a nitrogen atom, an oxygen atom, and a sulfur atom.

In one aspect of the present invention, the compound represented by the general formula (1) has a symmetric structure. For example, the compound may have a line symmetric structure. When the compound has a line symmetric structure, $R^1$ and $R^5$ in the general formula (1) are the same, and $R^2$ and $R^4$ are also the same. In one aspect of the present invention, the compound represented by the general formula (1) has an asymmetric structure.

In the description herein, the term "Substituent Group A" means one group or a combination of two or more groups selected from the group consisting of a hydroxy group, a halogen atom (for example, a fluorine atom, a chlorine atom, a bromine atom, and an iodine atom), an alkyl group (for example, having 1 to 40 carbon atoms), an alkoxy group (for example, having 1 to 40 carbon atoms), an alkylthio group (for example, having 1 to 40 carbon atoms), an aryl group (for example, having 6 to 30 carbon atoms), an aryloxy group (for example, having 6 to 30 carbon atoms), an arylthio group (for example, having 6 to 30 carbon atoms), a heteroaryl group (for example, having 5 to 30 ring skeleton-constituting atoms), a heteroaryloxy group (for example, having 5 to 30 ring skeleton-constituting atoms), a heteroarylthio group (for example, having 5 to 30 ring skeleton-constituting atoms), an acyl group (for example, having 1 to 40 carbon atoms), an alkenyl group (for example, having 1 to 40 carbon atoms), an alkynyl group (for example, having 1 to 40 carbon atoms), an alkoxycarbonyl group (for example, having 1 to 40 carbon atoms), an aryloxycarbonyl group (for example, having 1 to 40 carbon atoms), a heteroaryloxycarbonyl group (for example, having 1 to 40 carbon atoms), a silyl group (for example, a trialkylsilyl group having 1 to 40 carbon atoms), and a nitro group.

In the description herein, the term "Substituent Group B" means one group or a combination of two or more groups selected from the group consisting of an alkyl group (for example, having 1 to 40 carbon atoms), an alkoxy group (for example, having 1 to 40 carbon atoms), an aryl group (for example, having 6 to 30 carbon atoms), an aryloxy group (for example, having 6 to 30 carbon atoms), a heteroaryl group (for example, having 5 to 30 ring skeleton-constituting atoms), a heteroaryloxy group (for example, having 5 to 30 ring skeleton-constituting atoms), and a diarylamino-amino group (for example, having 0 to 20 carbon atoms).

In the description herein, the term "Substituent Group C" means one group or a combination of two or more groups selected from the group consisting of an alkyl group (for example, having 1 to 20 carbon atoms), an aryl group (for example, having 6 to 22 carbon atoms), a heteroaryl group (for example, having 5 to 20 ring skeleton-constituting atoms), and a diarylamino group (for example, having 12 to 20 carbon atoms).

In the description herein, the term "Substituent Group D" means one group or a combination of two or more groups selected from the group consisting of an alkyl group (for example, having 1 to 20 carbon atoms), an aryl group (for example, having 6 to 22 carbon atoms), and a heteroaryl group (for example, having 5 to 20 ring skeleton-constituting atoms).

In the description herein, the term "Substituent Group E" means one group or a combination of two or more groups selected from the group consisting of an alkyl group (for example, having 1 to 20 carbon atoms), and an aryl group (for example, having 6 to 22 carbon atoms).

In the description herein, in the case where "substituent" or "substituted or unsubstituted" is described, for example, the substituent may be selected from Substituent Group A, may be selected from Substituent Group B, may be selected from Substituent Group C, may be selected from Substituent Group D, or may be selected from Substituent Group E.

In Table 1 and Table 2 below, specific examples of the compound represented by the general formula (1) are shown. However, the compound represented by the general formula (1) that can be used in the present invention should not be construed as being limited by these specific examples.

In Table 1, structures of Compound 1 to Compound 184 are individually shown by specifying $R^1$ to $R^5$ of the general formula (1) for each compound.

In Table 2, structures of Compound 1 to Compound 6748200 are shown by collectively displaying $R^1$ to $R^5$ of a plurality of compounds in each row. For example, in the row of Compounds 1 to 184 in Table 2, compounds in which $R^3$ is fixed to Ar1 (phenyl group), $R^1$ and $R^5$ are fixed to D204 (carbazol-9-yl group), and $R^2$ and $R^4$ are D1 to D184 are referred to as Compounds 1 to 184 in this order. $R^2$ and $R^4$ are the same. That is, the row of Compounds 1 to 184 in Table 2 collectively represents Compounds 1 to 184 specified in Table 1. Similarly, in the row of Compounds 185 to 37536 in Table 2, $R^3$ is fixed to Ar1 (phenyl group), $R^1$ and $R^5$ are the same and are D1 to D203, and $R^2$ and $R^4$ are the same and are D1 to D184. Among the unfixed groups, $R^1$ and $R^5$, which take D1 to D203, are fixed first, and $R^2$ and $R^4$, which take D1 to D184, are sequentially replaced and assigned compound numbers. Therefore, compound numbers are assigned in such a manner that compounds in which $R^1$ and $R^5$ are D1 and $R^2$ and $R^4$ are D1 to D184 are sequentially assigned as Compounds 185 to 368, compounds in which $R^1$ and $R^5$ are D2 and $R^2$ and $R^4$ are D1 to D184 are sequentially assigned as Compounds 369 to 552, compounds in which $R^1$ and $R^5$ are D3 and $R^2$ and $R^4$ are D1 to D184 are sequentially assigned as Compounds 553 to 736, and then compounds in which $R^1$ and $R^5$ are D203 and $R^2$ and $R^4$ are D1 to D184 are sequentially assigned as Compounds 37353 to 37536. In the same manner, Compounds 37537 to 6748200 in Table 2 are also specified.

TABLE 1

| No. | $R^1$ | $R^2$ | $R^3$ | $R^4$ | $R^5$ |
|---|---|---|---|---|---|
| 1 | D204 | D1 | Ar1 | D1 | D204 |
| 2 | D204 | D2 | Ar1 | D2 | D204 |
| 3 | D204 | D3 | Ar1 | D3 | D204 |
| 4 | D204 | D4 | Ar1 | D4 | D204 |
| 5 | D204 | D5 | Ar1 | D5 | D204 |
| 6 | D204 | D6 | Ar1 | D6 | D204 |
| 7 | D204 | D7 | Ar1 | D7 | D204 |
| 8 | D204 | D8 | Ar1 | D8 | D204 |
| 9 | D204 | D9 | Ar1 | D9 | D204 |
| 10 | D204 | D10 | Ar1 | D10 | D204 |
| 11 | D204 | D11 | Ar1 | D11 | D204 |
| 12 | D204 | D12 | Ar1 | D12 | D204 |
| 13 | D204 | D13 | Ar1 | D13 | D204 |
| 14 | D204 | D14 | Ar1 | D14 | D204 |
| 15 | D204 | D15 | Ar1 | D15 | D204 |
| 16 | D204 | D16 | Ar1 | D16 | D204 |
| 17 | D204 | D17 | Ar1 | D17 | D204 |
| 18 | D204 | D18 | Ar1 | D18 | D204 |
| 19 | D204 | D19 | Ar1 | D19 | D204 |
| 20 | D204 | D20 | Ar1 | D20 | D204 |
| 21 | D204 | D21 | Ar1 | D21 | D204 |
| 22 | D204 | D22 | Ar1 | D22 | D204 |
| 23 | D204 | D23 | Ar1 | D23 | D204 |
| 24 | D204 | D24 | Ar1 | D24 | D204 |
| 25 | D204 | D25 | Ar1 | D25 | D204 |
| 26 | D204 | D26 | Ar1 | D26 | D204 |
| 27 | D204 | D27 | Ar1 | D27 | D204 |
| 28 | D204 | D28 | Ar1 | D28 | D204 |
| 29 | D204 | D29 | Ar1 | D29 | D204 |
| 30 | D204 | D30 | Ar1 | D30 | D204 |
| 31 | D204 | D31 | Ar1 | D31 | D204 |
| 32 | D204 | D32 | Ar1 | D32 | D204 |
| 33 | D204 | D33 | Ar1 | D33 | D204 |
| 34 | D204 | D34 | Ar1 | D34 | D204 |
| 35 | D204 | D35 | Ar1 | D35 | D204 |
| 36 | D204 | D36 | Ar1 | D36 | D204 |
| 37 | D204 | D37 | Ar1 | D37 | D204 |

TABLE 1-continued

| No. | $R^1$ | $R^2$ | $R^3$ | $R^4$ | $R^5$ |
|---|---|---|---|---|---|
| 38 | D204 | D38 | Ar1 | D38 | D204 |
| 39 | D204 | D39 | Ar1 | D39 | D204 |
| 40 | D204 | D40 | Ar1 | D40 | D204 |
| 41 | D204 | D41 | Ar1 | D41 | D204 |
| 42 | D204 | D42 | Ar1 | D42 | D204 |
| 43 | D204 | D43 | Ar1 | D43 | D204 |
| 44 | D204 | D44 | Ar1 | D44 | D204 |
| 45 | D204 | D45 | Ar1 | D45 | D204 |
| 46 | D204 | D46 | Ar1 | D46 | D204 |
| 47 | D204 | D47 | Ar1 | D47 | D204 |
| 48 | D204 | D48 | Ar1 | D48 | D204 |
| 49 | D204 | D49 | Ar1 | D49 | D204 |
| 50 | D204 | D50 | Ar1 | D50 | D204 |
| 51 | D204 | D51 | Ar1 | D51 | D204 |
| 52 | D204 | D52 | Ar1 | D52 | D204 |
| 53 | D204 | D53 | Ar1 | D53 | D204 |
| 54 | D204 | D54 | Ar1 | D54 | D204 |
| 55 | D204 | D55 | Ar1 | D55 | D204 |
| 56 | D204 | D56 | Ar1 | D56 | D204 |
| 57 | D204 | D57 | Ar1 | D57 | D204 |
| 58 | D204 | D58 | Ar1 | D58 | D204 |
| 59 | D204 | D59 | Ar1 | D59 | D204 |
| 60 | D204 | D60 | Ar1 | D60 | D204 |
| 61 | D204 | D61 | Ar1 | D61 | D204 |
| 62 | D204 | D62 | Ar1 | D62 | D204 |
| 63 | D204 | D63 | Ar1 | D63 | D204 |
| 64 | D204 | D64 | Ar1 | D64 | D204 |
| 65 | D204 | D65 | Ar1 | D65 | D204 |
| 66 | D204 | D66 | Ar1 | D66 | D204 |
| 67 | D204 | D67 | Ar1 | D67 | D204 |
| 68 | D204 | D68 | Ar1 | D68 | D204 |
| 69 | D204 | D69 | Ar1 | D69 | D204 |
| 70 | D204 | D70 | Ar1 | D70 | D204 |
| 71 | D204 | D71 | Ar1 | D71 | D204 |
| 72 | D204 | D72 | Ar1 | D72 | D204 |
| 73 | D204 | D73 | Ar1 | D73 | D204 |
| 74 | D204 | D74 | Ar1 | D74 | D204 |
| 75 | D204 | D75 | Ar1 | D75 | D204 |
| 76 | D204 | D76 | Ar1 | D76 | D204 |
| 77 | D204 | D77 | Ar1 | D77 | D204 |
| 78 | D204 | D78 | Ar1 | D78 | D204 |
| 79 | D204 | D79 | Ar1 | D79 | D204 |
| 80 | D204 | D80 | Ar1 | D80 | D204 |
| 81 | D204 | D81 | Ar1 | D81 | D204 |
| 82 | D204 | D82 | Ar1 | D82 | D204 |
| 83 | D204 | D83 | Ar1 | D83 | D204 |
| 84 | D204 | D84 | Ar1 | D84 | D204 |
| 85 | D204 | D85 | Ar1 | D85 | D204 |
| 86 | D204 | D86 | Ar1 | D86 | D204 |
| 87 | D204 | D87 | Ar1 | D87 | D204 |
| 88 | D204 | D88 | Ar1 | D88 | D204 |
| 89 | D204 | D89 | Ar1 | D89 | D204 |
| 90 | D204 | D90 | Ar1 | D90 | D204 |
| 91 | D204 | D91 | Ar1 | D91 | D204 |
| 92 | D204 | D92 | Ar1 | D92 | D204 |
| 93 | D204 | D93 | Ar1 | D93 | D204 |
| 94 | D204 | D94 | Ar1 | D94 | D204 |
| 95 | D204 | D95 | Ar1 | D95 | D204 |
| 96 | D204 | D96 | Ar1 | D96 | D204 |
| 97 | D204 | D97 | Ar1 | D97 | D204 |
| 98 | D204 | D98 | Ar1 | D98 | D204 |
| 99 | D204 | D99 | Ar1 | D99 | D204 |
| 100 | D204 | D100 | Ar1 | D100 | D204 |
| 101 | D204 | D101 | Ar1 | D101 | D204 |
| 102 | D204 | D102 | Ar1 | D102 | D204 |
| 103 | D204 | D103 | Ar1 | D103 | D204 |
| 104 | D204 | D104 | Ar1 | D104 | D204 |
| 105 | D204 | D105 | Ar1 | D105 | D204 |
| 106 | D204 | D106 | Ar1 | D106 | D204 |
| 107 | D204 | D107 | Ar1 | D107 | D204 |
| 108 | D204 | D108 | Ar1 | D108 | D204 |
| 109 | D204 | D109 | Ar1 | D109 | D204 |
| 110 | D204 | D110 | Ar1 | D110 | D204 |
| 111 | D204 | D111 | Ar1 | D111 | D204 |
| 112 | D204 | D112 | Ar1 | D112 | D204 |
| 113 | D204 | D113 | Ar1 | D113 | D204 |
| 114 | D204 | D114 | Ar1 | D114 | D204 |
| 115 | D204 | D115 | Ar1 | D115 | D204 |

TABLE 1-continued

| No. | $R^1$ | $R^2$ | $R^3$ | $R^4$ | $R^5$ |
|---|---|---|---|---|---|
| 116 | D204 | D116 | Ar1 | D116 | D204 |
| 117 | D204 | D117 | Ar1 | D117 | D204 |
| 118 | D204 | D118 | Ar1 | D118 | D204 |
| 119 | D204 | D119 | Ar1 | D119 | D204 |
| 120 | D204 | D120 | Ar1 | D120 | D204 |
| 121 | D204 | D121 | Ar1 | D121 | D204 |
| 122 | D204 | D122 | Ar1 | D122 | D204 |
| 123 | D204 | D123 | Ar1 | D123 | D204 |
| 124 | D204 | D124 | Ar1 | D124 | D204 |
| 125 | D204 | D125 | Ar1 | D125 | D204 |
| 126 | D204 | D126 | Ar1 | D126 | D204 |
| 127 | D204 | D127 | Ar1 | D127 | D204 |
| 128 | D204 | D128 | Ar1 | D128 | D204 |
| 129 | D204 | D129 | Ar1 | D129 | D204 |
| 130 | D204 | D130 | Ar1 | D130 | D204 |
| 131 | D204 | D131 | Ar1 | D131 | D204 |
| 132 | D204 | D132 | Ar1 | D132 | D204 |
| 133 | D204 | D133 | Ar1 | D133 | D204 |
| 134 | D204 | D134 | Ar1 | D134 | D204 |
| 135 | D204 | D135 | Ar1 | D135 | D204 |
| 136 | D204 | D136 | Ar1 | D136 | D204 |
| 137 | D204 | D137 | Ar1 | D137 | D204 |
| 138 | D204 | D138 | Ar1 | D138 | D204 |
| 139 | D204 | D139 | Ar1 | D139 | D204 |
| 140 | D204 | D140 | Ar1 | D140 | D204 |
| 141 | D204 | D141 | Ar1 | D141 | D204 |
| 142 | D204 | D142 | Ar1 | D142 | D204 |
| 143 | D204 | D143 | Ar1 | D143 | D204 |
| 144 | D204 | D144 | Ar1 | D144 | D204 |
| 145 | D204 | D145 | Ar1 | D145 | D204 |
| 146 | D204 | D146 | Ar1 | D146 | D204 |
| 147 | D204 | D147 | Ar1 | D147 | D204 |
| 148 | D204 | D148 | Ar1 | D148 | D204 |
| 149 | D204 | D149 | Ar1 | D149 | D204 |
| 150 | D204 | D150 | Ar1 | D150 | D204 |

TABLE 1-continued

| No. | $R^1$ | $R^2$ | $R^3$ | $R^4$ | $R^5$ |
|---|---|---|---|---|---|
| 151 | D204 | D151 | Ar1 | D151 | D204 |
| 152 | D204 | D152 | Ar1 | D152 | D204 |
| 153 | D204 | D153 | Ar1 | D153 | D204 |
| 154 | D204 | D154 | Ar1 | D154 | D204 |
| 155 | D204 | D155 | Ar1 | D155 | D204 |
| 156 | D204 | D156 | Ar1 | D156 | D204 |
| 157 | D204 | D157 | Ar1 | D157 | D204 |
| 158 | D204 | D158 | Ar1 | D158 | D204 |
| 159 | D204 | D159 | Ar1 | D159 | D204 |
| 160 | D204 | D160 | Ar1 | D160 | D204 |
| 161 | D204 | D161 | Ar1 | D161 | D204 |
| 162 | D204 | D162 | Ar1 | D162 | D204 |
| 163 | D204 | D163 | Ar1 | D163 | D204 |
| 104 | D204 | D164 | Ar1 | D164 | D204 |
| 165 | D204 | D165 | Ar1 | D165 | D204 |
| 166 | D204 | D166 | Ar1 | D166 | D204 |
| 167 | D204 | D167 | Ar1 | D167 | D204 |
| 168 | D204 | D168 | Ar1 | D168 | D204 |
| 169 | D204 | D169 | Ar1 | D169 | D204 |
| 170 | D204 | D170 | Ar1 | D170 | D204 |
| 171 | D204 | D171 | Ar1 | D171 | D204 |
| 172 | D204 | D172 | Ar1 | D172 | D204 |
| 173 | D204 | D173 | Ar1 | D173 | D204 |
| 174 | D204 | D174 | Ar1 | D174 | D204 |
| 175 | D204 | D175 | Ar1 | D175 | D204 |
| 176 | D204 | D176 | Ar1 | D176 | D204 |
| 177 | D204 | D177 | Ar1 | D177 | D204 |
| 178 | D204 | D178 | Ar1 | D178 | D204 |
| 179 | D204 | D179 | Ar1 | D179 | D204 |
| 180 | D204 | D180 | Ar1 | D180 | D204 |
| 181 | D204 | D181 | Ar1 | D181 | D204 |
| 182 | D204 | D182 | Ar1 | D182 | D204 |
| 183 | D204 | D183 | Ar1 | D183 | D204 |
| 184 | D204 | D184 | Ar1 | D184 | D204 |

TABLE 2

| | $R^1$ | $R^2$ | $R^3$ | $R^4$ | | Remarks |
|---|---|---|---|---|---|---|
| Compounds 1 to 184 | D204 | D1-D184 | Ar1 | D1-D184 | D204 | $R^2$ and $R^4$ are the same. |
| Compounds 185 to 37536 | D1-D203 | D1-D184 | Ar1 | D1-D184 | D1-D203 | $R^1$ and $R^5$ are the same, and $R^2$ and $R^4$ are the same. |
| Compounds 37537 to 75072 | D1-D204 | D1-D184 | Ar1 | H | H | |
| Compounds 75073 to 112608 | D1-D204 | H | Ar1 | H | D1-D184 | |
| Compounds 112609 to 150144 | H | D1-D204 | Ar1 | D1-D184 | H | |
| Compounds 150145 to 187680 | Ar1 | Ar1 | D1-D204 | D1-D184 | H | |
| Compounds 187681 to 225216 | D1-D204 | Ar1 | H | Ar1 | D1-D184 | |
| Compounds 225217 to 262752 | Ar1 | D1-D204 | Ar1 | D1-D184 | Ar1 | |
| Compounds 262753 to 300104 | D1-D204 | D1-D204 | Ar1 | D1-D184 | D1-D204 | $R^1$, $R^2$, and $R^5$ are the same, and the case where $R^1$, $R^2$, $R^4$, and $R^5$ are the same is omitted. |
| Compounds 300105 to 337456 | D1-D184 | D1-D204 | Ar1 | D1-D204 | D1-D204 | $R^2$, $R^4$, and $R^5$ are the same, and the case where $R^1$, $R^2$, $R^4$, and $R^5$ are the same is omitted. |
| Compounds 337457 to 374992 | D1-D184 | H | Ar1 | D1-D184 | D1-D204 | $R^1$ and $R^4$ are the same. |
| Compounds 374993 to 412528 | H | D1-D184 | Ar1 | D1-D184 | D1-D204 | $R^2$ and $R^4$ are the same. |
| Compounds 412529 to 450064 | Ar1 | D1-D204 | D1-D184 | H | H | |
| Compounds 450065 to 487600 | H | Ar1 | D1-D204 | D1-D184 | H | |
| Compounds 487601 to 525136 | Ar1 | D1-D204 | D1-D184 | D1-D204 | H | $R^2$ and $R^4$ are the same. |
| Compounds 525137 to 562672 | Ar1 | D1-D204 | Ar1 | D1-D184 | D1-D204 | $R^2$ and $R^5$ are the same. |
| Compounds 562673 to 600024 | Ar1 | D1-D184 | Ar1 | D1-D204 | D1-D204 | $R^4$ and $R^5$ are the same, and the case where $R^2$, $R^4$, and $R^5$ are the same is omitted. |
| Compounds 600025 to 637560 | H | Ar1 | D1-D184 | D1-D204 | D1-D204 | $R^4$ and $R^5$ are the same. |
| Compounds 637561 to 675096 | Ar1 | H | D1-D184 | D1-D204 | D1-D204 | $R^4$ and $R^5$ are the same. |
| Compounds 675097 to 712448 | H | Ar1 | D1-D204 | D1-D184 | D1-D204 | $R^3$ and $R^5$ are the same, and the case where $R^3$, $R^4$, and $R^5$ are the same is omitted. |
| Compounds 712449 to 749800 | Ar1 | H | D1-D204 | D1-D184 | D1-D204 | $R^3$ and $R^5$ are the same, and the case where $R^3$, $R^4$, and $R^5$ are the same is omitted. |
| Compounds 749801 to 787336 | D1-D204 | D1-D184 | Ar2 | D1-D184 | D1-D204 | $R^1$ and $R^5$ are the same, and $R^2$ and $R^4$ are the same. |
| Compounds 787337 to 824872 | D1-D204 | D1-D184 | Ar2 | H | H | |
| Compounds 824873 to 862408 | D1-D204 | H | Ar2 | H | D1-D184 | |
| Compounds 862409 to 899944 | H | D1-D204 | Ar2 | D1-D184 | H | |
| Compounds 899945 to 937480 | Ar2 | Ar2 | D1-D204 | D1-D184 | H | |
| Compounds 937481 to 975016 | D1-D204 | Ar2 | H | Ar2 | D1-D184 | |
| Compounds 975017 to 1012552 | Ar2 | D1-D204 | Ar2 | D1-D184 | Ar2 | |

TABLE 2-continued

| | $R^1$ | $R^2$ | $R^3$ | $R^4$ | | Remarks |
|---|---|---|---|---|---|---|
| Compounds 1012553 to 1049904 | D1-D204 | D1-D204 | Ar2 | D1-D184 | D1-D204 | $R^1$, $R^2$, and $R^5$ are the same, and the case where $R^1$, $R^2$, $R^4$, and $R^5$ are the same is omitted. |
| Compounds 1049905 to 1087256 | D1-D184 | D1-D204 | Ar2 | D1-D204 | D1-D204 | $R^2$, $R^4$, and $R^5$ are the same, and the case where $R^1$, $R^2$, $R^4$, and $R^5$ are the same is omitted. |
| Compounds 1087257 to 1124792 | D1-D184 | H | Ar2 | D1-D184 | D1-D204 | $R^1$ and $R^4$ are the same. |
| Compounds 1124793 to 1162328 | H | D1-D184 | Ar2 | D1-D184 | D1-D204 | $R^2$ and $R^4$ are the same. |
| Compounds 1162329 to 1199864 | Ar2 | D1-D204 | D1-D184 | H | H | |
| Compounds 1199865 to 1237400 | H | Ar2 | D1-D204 | D1-D184 | H | |
| Compounds 1237401 to 1274936 | Ar2 | D1-D204 | D1-D184 | D1-D204 | H | $R^2$ and $R^4$ are the same. |
| Compounds 1274937 to 1312472 | Ar2 | D1-D204 | Ar2 | D1-D184 | D1-D204 | $R^2$ and $R^5$ are the same. |
| Compounds 1312473 to 1349824 | Ar2 | D1-D184 | Ar2 | D1-D204 | D1-D204 | $R^4$ and $R^5$ are the same, and the case where $R^2$, $R^4$, and $R^5$ are the same is omitted. |
| Compounds 1349825 to 1387360 | H | Ar2 | D1-D184 | D1-D204 | D1-D204 | $R^4$ and $R^5$ are the same. |
| Compounds 1387361 to 1424896 | Ar2 | H | D1-D184 | D1-D204 | D1-D204 | $R^4$ and $R^5$ are the same. |
| Compounds 1424897 to 1462248 | H | Ar2 | D1-D204 | D1-D184 | D1-D204 | $R^3$ and $R^5$ are the same, and the case where $R^3$, $R^4$, and $R^5$ are the same is omitted. |
| Compounds 1462249 to 1499600 | Ar2 | H | D1-D204 | D1-D184 | D1-D204 | $R^3$ and $R^5$ are the same, and the case where $R^3$, $R^4$, and $R^5$ are the same is omitted. |
| Compounds 1499601 to 1537136 | D1-D204 | D1-D184 | Ar3 | D1-D184 | D1-D204 | $R^1$ and $R^5$ are the same, and $R^2$ and $R^4$ are the same. |
| Compounds 1537137 to 1574672 | D1-D204 | D1-D184 | Ar3 | H | H | |
| Compounds 1574673 to 1612208 | D1-D204 | H | Ar3 | H | D1-D184 | |
| Compounds 1612209 to 1649744 | H | D1-D204 | Ar3 | D1-D184 | H | |
| Compounds 1649745 to 1687280 | Ar3 | Ar3 | D1-D204 | D1-D184 | H | |
| Compounds 1687281 to 1724816 | D1-D204 | Ar3 | H | Ar3 | D1-D184 | |
| Compounds 1724817 to 1762352 | Ar3 | D1-D204 | Ar3 | D1-D184 | Ar3 | |
| Compounds 1762353 to 1799704 | D1-D204 | D1-D204 | Ar3 | D1-D184 | D1-D204 | $R^1$, $R^2$, and $R^5$ are the same, and the case where $R^1$, $R^2$, $R^4$, and $R^5$ are the same is omitted. |
| Compounds 1799705 to 1837056 | D1-D184 | D1-D204 | Ar3 | D1-D204 | D1-D204 | $R^2$, $R^4$, and $R^5$ are the same, and the case where $R^1$, $R^2$, $R^4$, and $R^5$ are the same is omitted. |
| Compounds 1837057 to 1874592 | D1-D184 | H | Ar3 | D1-D184 | D1-D204 | $R^1$ and $R^4$ are the same. |
| Compounds 1874593 to 1912128 | H | D1-D184 | Ar3 | D1-D184 | D1-D204 | $R^2$ and $R^4$ are the same. |
| Compounds 1912129 to 1949664 | Ar3 | D1-D204 | D1-D184 | H | H | |
| Compounds 1949665 to 1987200 | H | Ar3 | D1-D204 | D1-D184 | H | |
| Compounds 1987201 to 2024736 | Ar3 | D1-D204 | D1-D184 | D1-D204 | H | $R^2$ and $R^4$ are the same. |
| Compounds 2024737 to 2062272 | Ar3 | D1-D204 | Ar3 | D1-D184 | D1-D204 | $R^2$ and $R^5$ are the same. |
| Compounds 2062273 to 2099624 | Ar3 | D1-D184 | Ar3 | D1-D204 | D1-D204 | $R^4$ and $R^5$ are the same, and the case where $R^2$, $R^4$, and $R^5$ are the same is omitted. |
| Compounds 2099625 to 2137160 | H | Ar3 | D1-D184 | D1-D204 | D1-D204 | $R^4$ and $R^5$ are the same. |
| Compounds 2137161 to 2174696 | Ar3 | H | D1-D184 | D1-D204 | D1-D204 | $R^4$ and $R^5$ are the same. |
| Compounds 2174697 to 2212048 | H | Ar3 | D1-D204 | D1-D184 | D1-D204 | $R^3$ and $R^5$ are the same, and the case where $R^3$, $R^4$, and $R^5$ are the same is omitted. |
| Compounds 2212049 to 2249400 | Ar3 | H | D1-D204 | D1-D184 | D1-D204 | $R^3$ and $R^5$ are the same, and the case where $R^3$, $R^4$, and $R^5$ are the same is omitted. |
| Compounds 2249401 to 2286936 | D1-D204 | D1-D184 | Ar4 | D1-D184 | D1-D204 | $R^1$ and $R^5$ are the same, and $R^2$ and $R^4$ are the same. |
| Compounds 2286937 to 2324472 | D1-D204 | D1-D184 | Ar4 | H | H | |
| Compounds 2324473 to 2362008 | D1-D204 | H | Ar4 | H | D1-D184 | |
| Compounds 2362009 to 2399544 | H | D1-D204 | Ar4 | D1-D184 | H | |
| Compounds 2399545 to 2437080 | Ar4 | Ar4 | D1-D204 | D1-D184 | H | |
| Compounds 2437081 to 2474616 | D1-D204 | Ar4 | H | Ar4 | D1-D184 | |
| Compounds 2474617 to 2512152 | Ar4 | D1-D204 | Ar4 | D1-D184 | Ar4 | |
| Compounds 2512153 to 2549504 | D1-D204 | D1-D204 | Ar4 | D1-D184 | D1-D204 | $R^1$, $R^2$, and $R^5$ are the same, and the case where $R^1$, $R^2$, $R^4$, and $R^5$ are the same is omitted. |
| Compounds 2549505 to 2586856 | D1-D184 | D1-D204 | Ar4 | D1-D204 | D1-D204 | $R^2$, $R^4$, and $R^5$ are the same, and the case where $R^1$, $R^2$, $R^4$, and $R^5$ are the same is omitted. |
| Compounds 2586857 to 2624392 | D1-D184 | H | Ar4 | D1-D184 | D1-D204 | $R^1$ and $R^4$ are the same. |
| Compounds 2624393 to 2661928 | H | D1-D184 | Ar4 | D1-D184 | D1-D204 | $R^2$ and $R^4$ are the same. |
| Compounds 2661929 to 2699464 | Ar4 | D1-D204 | D1-D184 | H | H | |
| Compounds 2699465 to 2737000 | H | Ar4 | D1-D204 | D1-D184 | H | |
| Compounds 2737001 to 2774536 | Ar4 | D1-D204 | D1-D184 | D1-D204 | H | $R^2$ and $R^4$ are the same. |
| Compounds 2774537 to 2812072 | Ar4 | D1-D204 | Ar4 | D1-D184 | D1-D204 | $R^2$ and $R^5$ are the same. |
| Compounds 2812073 to 2849424 | Ar4 | D1-D184 | Ar4 | D1-D204 | D1-D204 | $R^4$ and $R^5$ are the same, and the case where $R^2$, $R^4$, and $R^5$ are the same is omitted. |
| Compounds 2849425 to 2886960 | H | Ar4 | D1-D184 | D1-D204 | D1-D204 | $R^4$ and $R^5$ are the same. |
| Compounds 2886961 to 2924496 | Ar4 | H | D1-D184 | D1-D204 | D1-D204 | $R^4$ and $R^5$ are the same. |
| Compounds 2924497 to 2961848 | H | Ar4 | D1-D204 | D1-D184 | D1-D204 | $R^3$ and $R^5$ are the same, and the case where $R^3$, $R^4$, and $R^5$ are the same is omitted. |

TABLE 2-continued

| | $R^1$ | $R^2$ | $R^3$ | $R^4$ | | Remarks |
|---|---|---|---|---|---|---|
| Compounds 2961849 to 2999200 | Ar4 | H | D1-D204 | D1-D184 | D1-D204 | $R^3$ and $R^5$ are the same, and the case where $R^3$, $R^4$, and $R^5$ are the same is omitted. |
| Compounds 2999201 to 3036736 | D1-D204 | D1-D184 | Ar5 | D1-D184 | D1-D204 | $R^1$ and $R^5$ are the same, and $R^2$ and $R^4$ are the same. |
| Compounds 3036737 to 3074272 | D1-D204 | D1-D184 | Ar5 | H | H | |
| Compounds 3074273 to 3111808 | D1-D204 | H | Ar5 | H | D1-D184 | |
| Compounds 3111809 to 3149344 | H | D1-D204 | Ar5 | D1-D184 | H | |
| Compounds 3149345 to 3186880 | Ar5 | Ar5 | D1-D204 | D1-D184 | H | |
| Compounds 3186881 to 3224416 | D1-D204 | Ar5 | H | Ar5 | D1-D184 | |
| Compounds 3224417 to 3261952 | Ar5 | D1-D204 | Ar5 | D1-D184 | Ar5 | |
| Compounds 3261953 to 3299304 | D1-D204 | D1-D204 | Ar5 | D1-D184 | D1-D204 | $R^1$, $R^2$, and $R^5$ are the same, and the case where $R^1$, $R^2$, $R^4$, and $R^5$ are the same is omitted. |
| Compounds 3299305 to 3336656 | D1-D184 | D1-D204 | Ar5 | D1-D204 | D1-D204 | $R^2$, $R^4$, and $R^5$ are the same, and the case where $R^1$, $R^2$, $R^4$, and $R^5$ are the same is omitted. |
| Compounds 3336657 to 3374192 | D1-D184 | H | Ar5 | D1-D184 | D1-D204 | $R^1$ and $R^4$ are the same. |
| Compounds 3374193 to 3411728 | H | D1-D184 | Ar5 | D1-D184 | D1-D204 | $R^2$ and $R^4$ are the same. |
| Compounds 3411729 to 3449264 | Ar5 | D1-D204 | D1-D184 | H | H | |
| Compounds 3449265 to 3486800 | H | Ar5 | D1-D204 | D1-D184 | H | |
| Compounds 3486801 to 3524336 | Ar5 | D1-D204 | D1-D184 | D1-D204 | H | $R^2$ and $R^4$ are the same. |
| Compounds 3524337 to 3561872 | Ar5 | D1-D204 | Ar5 | D1-D184 | D1-D204 | $R^2$ and $R^5$ are the same. |
| Compounds 3561873 to 3599224 | Ar5 | D1-D184 | Ar5 | D1-D204 | D1-D204 | $R^4$ and $R^5$ are the same, and the case where $R^2$, $R^4$, and $R^5$ are the same is omitted. |
| Compounds 3599225 to 3636760 | H | Ar5 | D1-D184 | D1-D204 | D1-D204 | $R^4$ and $R^5$ are the same. |
| Compounds 3636761 to 3674296 | Ar5 | H | D1-D184 | D1-D204 | D1-D204 | $R^4$ and $R^5$ are the same. |
| Compounds 3674297 to 3711648 | H | Ar5 | D1-D204 | D1-D184 | D1-D204 | $R^3$ and $R^5$ are the same, and the case where $R^3$, $R^4$, and $R^5$ are the same is omitted. |
| Compounds 3711649 to 3749000 | Ar5 | H | D1-D204 | D1-D184 | D1-D204 | $R^3$ and $R^5$ are the same, and the case where $R^3$, $R^4$, and $R^5$ are the same is omitted. |
| Compounds 3749001 to 3786536 | D1-D204 | D1-D184 | Ar6 | D1-D184 | D1-D204 | $R^1$ and $R^5$ are the same, and $R^2$ and $R^4$ are the same. |
| Compounds 3786537 to 3824072 | D1-D204 | D1-D184 | Ar6 | H | H | |
| Compounds 3824073 to 3861608 | D1-D204 | H | Ar6 | H | D1-D184 | |
| Compounds 3861609 to 3899144 | H | D1-D204 | Ar6 | D1-D184 | H | |
| Compounds 3899145 to 3936680 | Ar6 | Ar6 | D1-D204 | D1-D184 | H | |
| Compounds 3936681 to 3974216 | D1-D204 | Ar6 | H | Ar6 | D1-D184 | |
| Compounds 3974217 to 4011752 | Ar6 | D1-D204 | Ar6 | D1-D184 | Ar6 | |
| Compounds 4011753 to 4049104 | D1-D204 | D1-D204 | Ar6 | D1-D184 | D1-D204 | $R^1$, $R^2$, and $R^5$ are the same, and the case where $R^1$, $R^2$, $R^4$, and $R^5$ are the same is omitted. |
| Compounds 4049105 to 4086456 | D1-D184 | D1-D204 | Ar6 | D1-D204 | D1-D204 | $R^2$, $R^4$, and $R^5$ are the same, and the case where $R^1$, $R^2$, $R^4$, and $R^5$ are the same is omitted. |
| Compounds 4086457 to 4123992 | D1-D184 | H | Ar6 | D1-D184 | D1-D204 | $R^1$ and $R^4$ are the same. |
| Compounds 4123993 to 4161528 | H | D1-D184 | Ar6 | D1-D184 | D1-D204 | $R^2$ and $R^4$ are the same. |
| Compounds 4161529 to 4199064 | Ar6 | D1-D204 | D1-D184 | H | H | |
| Compounds 4199065 to 4236600 | H | Ar6 | D1-D204 | D1-D184 | H | |
| Compounds 4236601 to 4274136 | Ar6 | D1-D204 | D1-D184 | D1-D204 | H | $R^2$ and $R^4$ are the same. |
| Compounds 4274137 to 4311672 | Ar6 | D1-D204 | Ar6 | D1-D184 | D1-D204 | $R^2$ and $R^5$ are the same. |
| Compounds 4311673 to 4349024 | Ar6 | D1-D184 | Ar6 | D1-D204 | D1-D204 | $R^4$ and $R^5$ are the same, and the case where $R^2$, $R^4$, and $R^5$ are the same is omitted. |
| Compounds 4349025 to 4386560 | H | Ar6 | D1-D184 | D1-D204 | D1-D204 | $R^4$ and $R^5$ are the same. |
| Compounds 4386561 to 4424096 | Ar6 | H | D1-D184 | D1-D204 | D1-D204 | $R^4$ and $R^5$ are the same. |
| Compounds 4424097 to 4461448 | H | Ar6 | D1-D204 | D1-D184 | D1-D204 | $R^3$ and $R^5$ are the same, and the case where $R^3$, $R^4$, and $R^5$ are the same is omitted. |
| Compounds 4461449 to 4498800 | Ar6 | H | D1-D204 | D1-D184 | D1-D204 | $R^3$ and $R^5$ are the same, and the case where $R^3$, $R^4$, and $R^5$ are the same is omitted. |
| Compounds 4498801 to 4536336 | D1-D204 | D1-D184 | Ar7 | D1-D184 | D1-D204 | $R^1$ and $R^5$ are the same, and $R^2$ and $R^4$ are the same. |
| Compounds 4536337 to 4573872 | D1-D204 | D1-D184 | Ar7 | H | H | |
| Compounds 4573873 to 4611408 | D1-D204 | H | Ar7 | H | D1-D184 | |
| Compounds 4611409 to 4648944 | H | D1-D204 | Ar7 | D1-D184 | H | |
| Compounds 4648945 to 4686480 | Ar7 | Ar7 | D1-D204 | D1-D184 | H | |
| Compounds 4686481 to 4724016 | D1-D204 | Ar7 | H | Ar7 | D1-D184 | |
| Compounds 4724017 to 4761552 | Ar7 | D1-D204 | Ar7 | D1-D184 | Ar7 | |

TABLE 2-continued

| | $R^1$ | $R^2$ | $R^3$ | $R^4$ | | Remarks |
|---|---|---|---|---|---|---|
| Compounds 4761553 to 4798904 | D1-D204 | D1-D204 | Ar7 | D1-D184 | D1-D204 | $R^1$, $R^2$, and $R^5$ are the same, and the case where $R^1$, $R^2$, $R^4$, and $R^5$ are the same is omitted. |
| Compounds 4798905 to 4836256 | D1-D184 | D1-D204 | Ar7 | D1-D204 | D1-D204 | $R^2$, $R^4$, and $R^5$ are the same, and the case where $R^1$, $R^2$, $R^4$, and $R^5$ are the same is omitted. |
| Compounds 4836257 to 4873792 | D1-D184 | H | Ar7 | D1-D184 | D1-D204 | $R^1$ and $R^4$ are the same. |
| Compounds 4873793 to 4911328 | H | D1-D184 | Ar7 | D1-D184 | D1-D204 | $R^2$ and $R^4$ are the same. |
| Compounds 4911329 to 4948864 | Ar7 | D1-D204 | D1-D184 | H | H | |
| Compounds 4948865 to 4986400 | H | Ar7 | D1-D204 | D1-D184 | H | |
| Compounds 4986401 to 5023936 | Ar7 | D1-D204 | D1-D184 | D1-D204 | H | $R^2$ and $R^4$ are the same. |
| Compounds 5023937 to 5061472 | Ar7 | D1-D204 | Ar7 | D1-D184 | D1-D204 | $R^2$ and $R^5$ are the same. |
| Compounds 5061473 to 5098824 | Ar7 | D1-D184 | Ar7 | D1-D204 | D1-D204 | $R^4$ and $R^5$ are the same, and the case where $R^2$, $R^4$, and $R^5$ are the same is omitted. |
| Compounds 5098825 to 5136360 | H | Ar7 | D1-D184 | D1-D204 | D1-D204 | $R^4$ and $R^5$ are the same. |
| Compounds 5136361 to 5173896 | Ar7 | H | D1-D184 | D1-D204 | D1-D204 | $R^4$ and $R^5$ are the same. |
| Compounds 5173897 to 5211248 | H | Ar7 | D1-D204 | D1-D184 | D1-D204 | $R^3$ and $R^5$ are the same, and the case where $R^3$, $R^4$, and $R^5$ are the same is omitted. |
| Compounds 5211249 to 5248600 | Ar7 | H | D1-D204 | D1-D184 | D1-D204 | $R^3$ and $R^5$ are the same, and the case where $R^3$, $R^4$, and $R^5$ are the same is omitted. |
| Compounds 5248601 to 5286136 | D1-D204 | D1-D184 | Ar8 | D1-D184 | D1-D204 | $R^1$ and $R^5$ are the same, and $R^2$ and $R^4$ are the same. |
| Compounds 5286137 to 5323672 | D1-D204 | D1-D184 | Ar8 | H | H | |
| Compounds 5323673 to 5361208 | D1-D204 | H | Ar8 | H | D1-D184 | |
| Compounds 5361209 to 5398744 | H | D1-D204 | Ar8 | D1-D184 | H | |
| Compounds 5398745 to 5436280 | Ar8 | Ar8 | D1-D204 | D1-D184 | H | |
| Compounds 5436281 to 5473816 | D1-D204 | Ar8 | H | Ar8 | D1-D184 | |
| Compounds 5473817 to 5511352 | Ar8 | D1-D204 | Ar8 | D1-D184 | Ar8 | |
| Compounds 5511353 to 5548704 | D1-D204 | D1-D204 | Ar8 | D1-D184 | D1-D204 | $R^1$, $R^2$, and $R^5$ are the same, and the case where $R^1$, $R^2$, $R^4$, and $R^5$ are the same is omitted. |
| Compounds 5548705 to 5586056 | D1-D184 | D1-D204 | Ar8 | D1-D204 | D1-D204 | $R^2$, $R^4$, and $R^5$ are the same, and the case where $R^1$, $R^2$, $R^4$, and $R^5$ are the same is omitted. |
| Compounds 5586057 to 5623592 | D1-D184 | H | Ar8 | D1-D184 | D1-D204 | $R^1$ and $R^4$ are the same. |
| Compounds 5623593 to 5661128 | H | D1-D184 | Ar8 | D1-D184 | D1-D204 | $R^2$ and $R^4$ are the same. |
| Compounds 5661129 to 5698664 | Ar8 | D1-D204 | D1-D184 | H | H | |
| Compounds 5698665 to 5736200 | H | Ar8 | D1-D204 | D1-D184 | H | |
| Compounds 5736201 to 5773736 | Ar8 | D1-D204 | D1-D184 | D1-D204 | H | $R^2$ and $R^4$ are the same. |
| Compounds 5773737 to 5811272 | Ar8 | D1-D204 | Ar8 | D1-D184 | D1-D204 | $R^2$ and $R^5$ are the same. |
| Compounds 5811273 to 5848624 | Ar8 | D1-D184 | Ar8 | D1-D204 | D1-D204 | $R^4$ and $R^5$ are the same, and the case where $R^2$, $R^4$, and $R^5$ are the same is omitted. |
| Compounds 5848625 to 5886160 | H | Ar8 | D1-D184 | D1-D204 | D1-D204 | $R^4$ and $R^5$ are the same. |
| Compounds 5886161 to 5923696 | Ar8 | H | D1-D184 | D1-D204 | D1-D204 | $R^4$ and $R^5$ are the same. |
| Compounds 5923697 to 5961048 | H | Ar8 | D1-D204 | D1-D184 | D1-D204 | $R^3$ and $R^5$ are the same, and the case where $R^3$, $R^4$, and $R^5$ are the same is omitted. |
| Compounds 5961049 to 5998400 | Ar8 | H | D1-D204 | D1-D184 | D1-D204 | $R^3$ and $R^5$ are the same, and the case where $R^3$, $R^4$, and $R^5$ are the same is omitted. |
| Compounds 5998401 to 6035936 | D1-D204 | D1-D184 | Ar27 | D1-D184 | D1-D204 | $R^1$ and $R^5$ are the same, and $R^2$ and $R^4$ are the same. |
| Compounds 6035937 to 6073472 | D1-D204 | D1-D184 | Ar27 | H | H | |
| Compounds 6073473 to 6111008 | D1-D204 | H | Ar27 | H | D1-D184 | |
| Compounds 6111009 to 6148544 | H | D1-D204 | Ar27 | D1-D184 | H | |
| Compounds 6148545 to 6186080 | Ar27 | Ar27 | D1-D204 | D1-D184 | H | |
| Compounds 6186081 to 6223616 | D1-D204 | Ar27 | H | Ar27 | D1-D184 | |
| Compounds 6223617 to 6261152 | Ar27 | D1-D204 | Ar27 | D1-D184 | Ar27 | |
| Compounds 6261153 to 6298504 | D1-D204 | D1-D204 | Ar27 | D1-D184 | D1-D204 | $R^1$, $R^2$, and $R^5$ are the same, and the case where $R^1$, $R^2$, $R^4$, and $R^5$ are the same is omitted. |
| Compounds 6298505 to 6335856 | D1-D184 | D1-D204 | Ar27 | D1-D204 | D1-D204 | $R^2$, $R^4$, and $R^5$ are the same, and the case where $R^1$, $R^2$, $R^4$, and $R^5$ are the same is omitted. |
| Compounds 6335857 to 6373392 | D1-D184 | H | Ar27 | D1-D184 | D1-D204 | $R^1$ and $R^4$ are the same. |
| Compounds 6373393 to 6410928 | H | D1-D184 | Ar27 | D1-D184 | D1-D204 | $R^2$ and $R^4$ are the same. |
| Compounds 6410929 to 6448464 | Ar27 | D1-D204 | D1-D184 | H | H | |
| Compounds 6448465 to 6486000 | H | Ar27 | D1-D204 | D1-D184 | H | |
| Compounds 6486001 to 6523536 | Ar27 | D1-D204 | D1-D184 | D1-D204 | H | $R^2$ and $R^4$ are the same. |
| Compounds 6523537 to 6561072 | Ar27 | D1-D204 | Ar27 | D1-D184 | D1-D204 | $R^2$ and $R^5$ are the same. |
| Compounds 6561073 to 6598424 | Ar27 | D1-D184 | Ar27 | D1-D204 | D1-D204 | $R^4$ and $R^5$ are the same, and the case where $R^2$, $R^4$, and $R^5$ are the same is omitted. |
| Compounds 6598425 to 6635960 | H | Ar27 | D1-D184 | D1-D204 | D1-D204 | $R^4$ and $R^5$ are the same. |
| Compounds 6635961 to 6673496 | Ar27 | H | D1-D184 | D1-D204 | D1-D204 | $R^4$ and $R^5$ are the same. |

TABLE 2-continued

| | $R^1$ | $R^2$ | $R^3$ | $R^4$ | | Remarks |
|---|---|---|---|---|---|---|
| Compounds 6673497 to 6710848 | H | Ar27 | D1-D204 | D1-D184 | D1-D204 | $R^3$ and $R^5$ are the same, and the case where $R^3$, $R^4$, and $R^5$ are the same is omitted. |
| Compounds 6710849 to 6748200 | Ar27 | H | D1-D204 | D1-D184 | D1-D204 | $R^3$ and $R^5$ are the same, and the case where $R^3$, $R^4$, and $R^5$ are the same is omitted. |

Compounds obtained by substituting all hydrogen atoms present in the molecules of the above Compound 1 to Compound 6412032 with deuterium atoms are disclosed as Compound 1(D) to Compound 6412032(D). In addition, among the specific examples of the compound, in the case where a rotamer is present, a mixture of rotamers and each separated rotamer are also disclosed in the description herein.

In a preferred aspect of the present invention, the compound represented by the general formula (1) is selected from the following group of compounds.

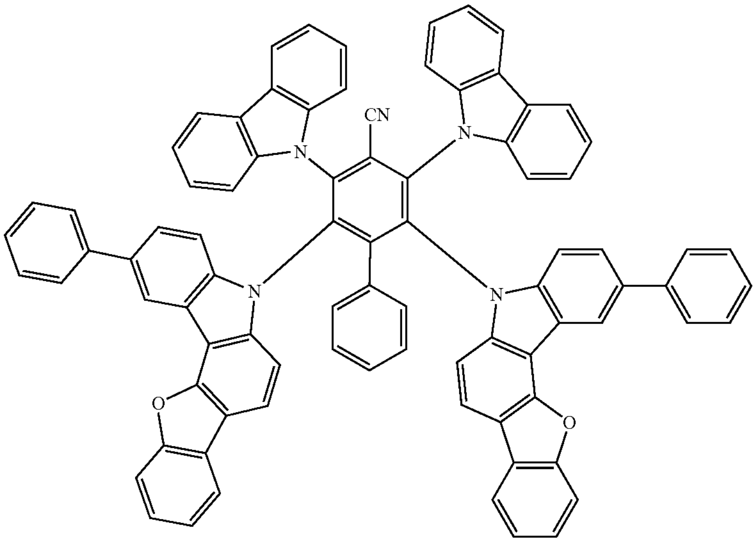

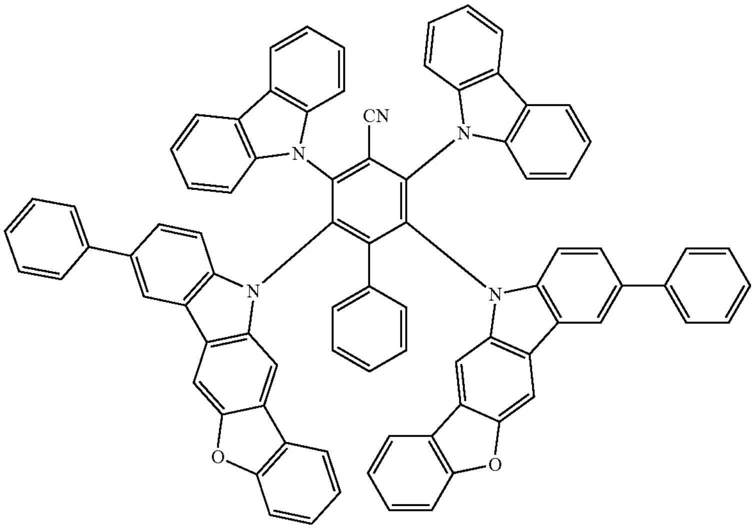

-continued
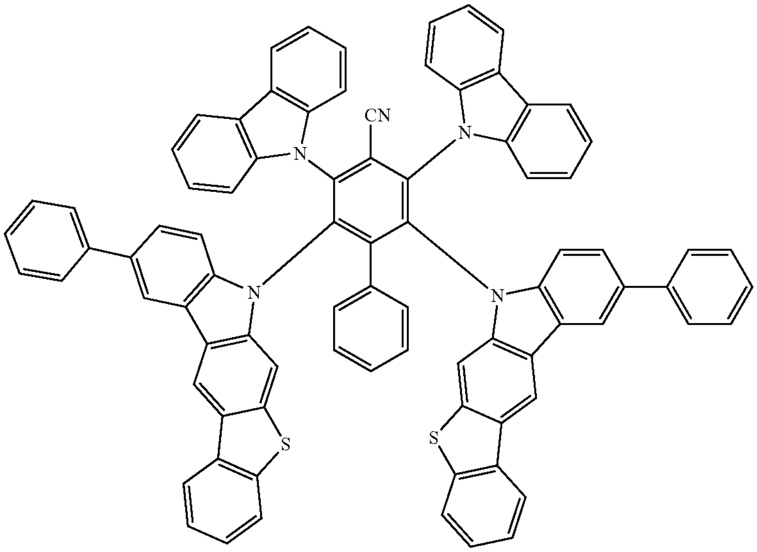
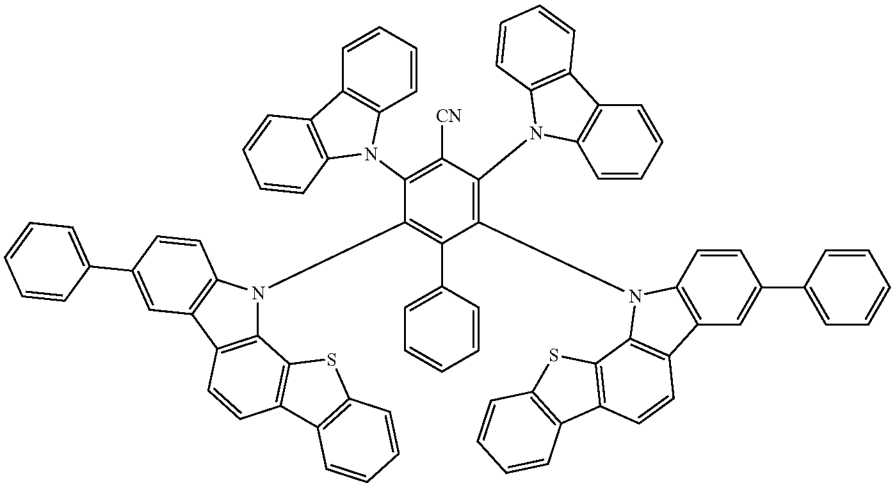
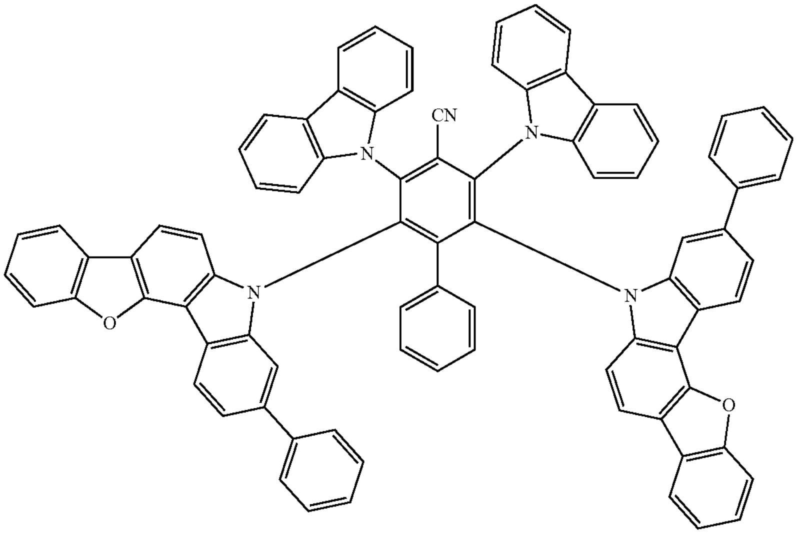

-continued
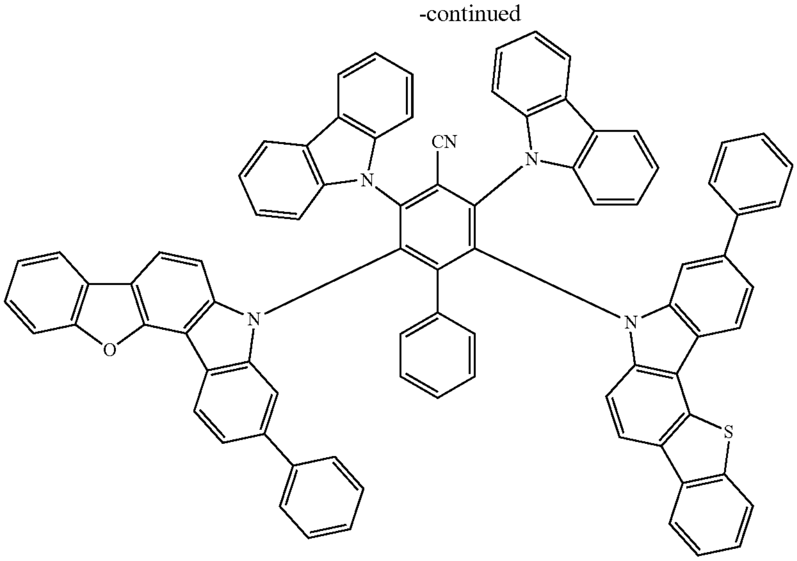
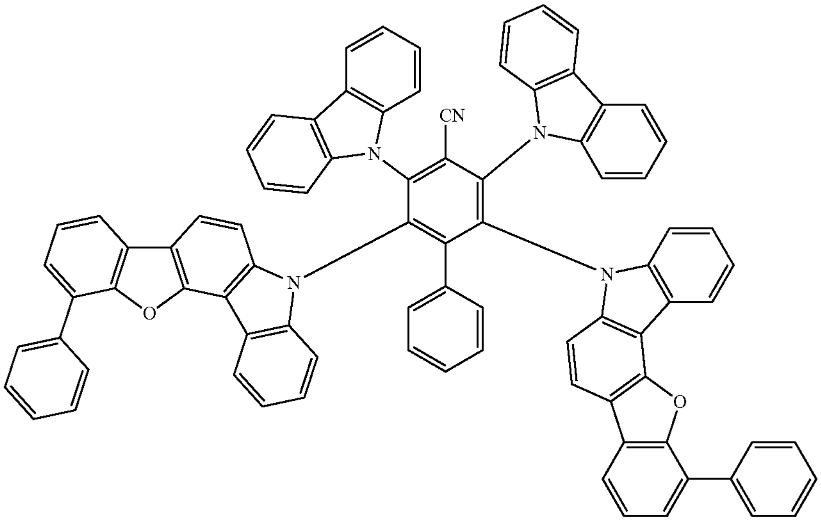
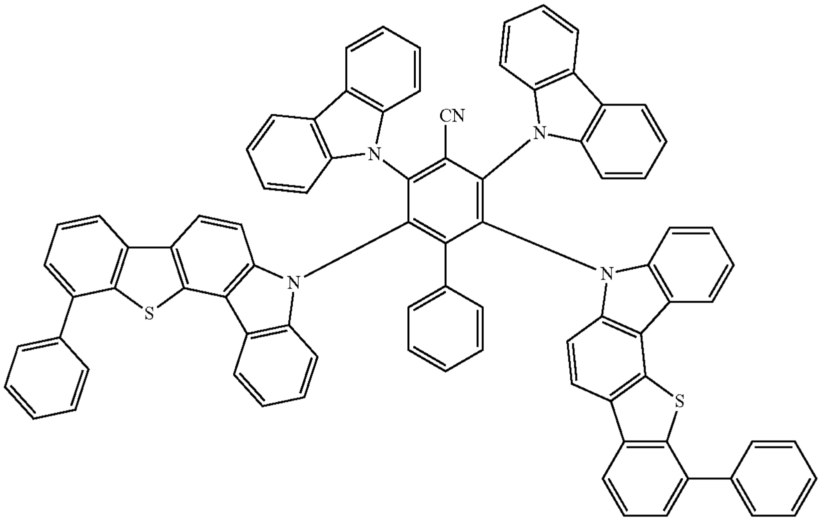

-continued
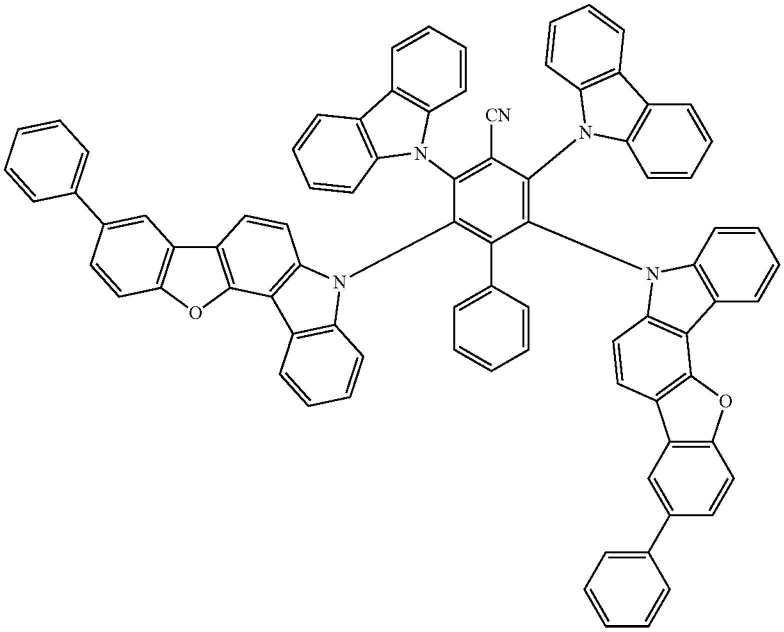
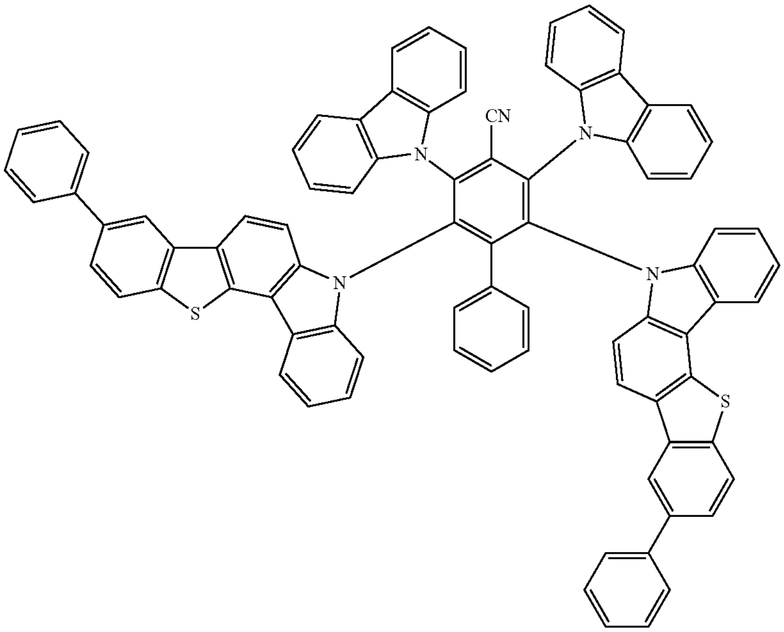
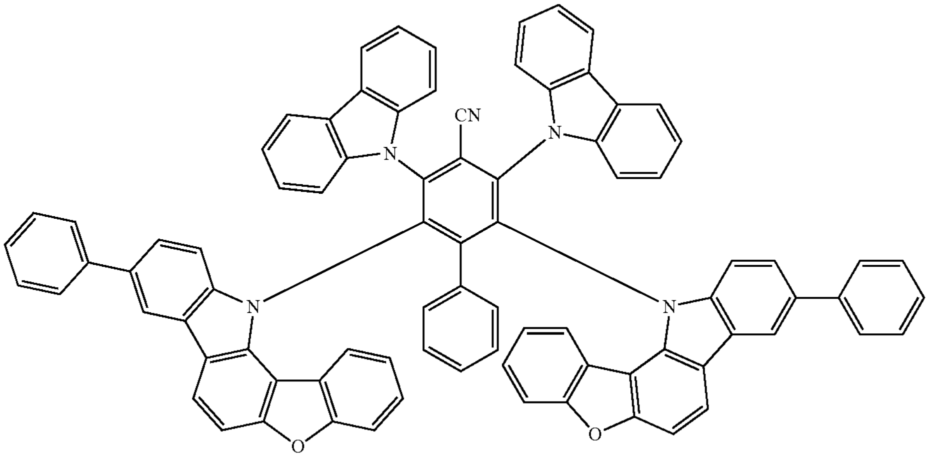

-continued
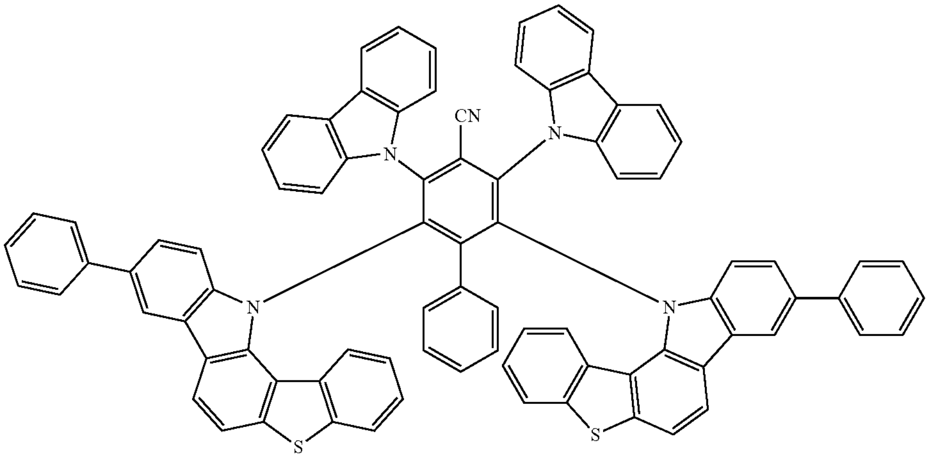
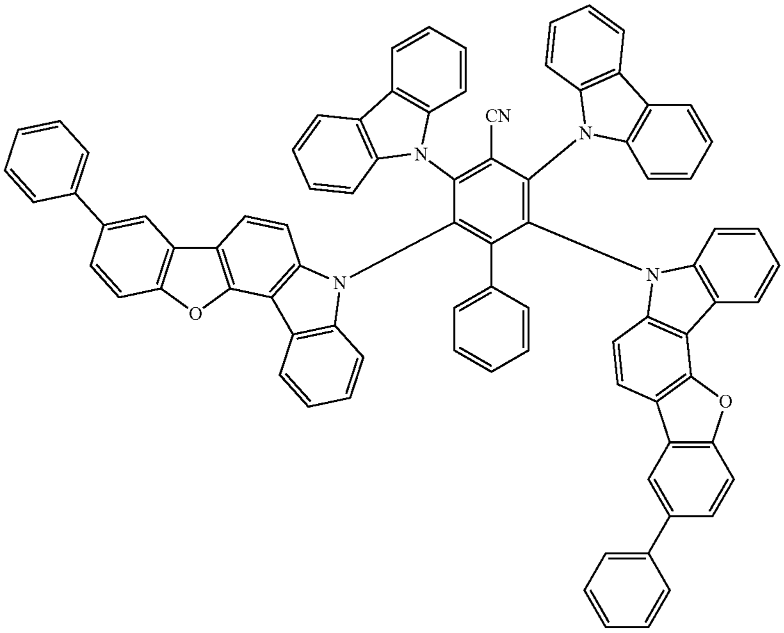

-continued

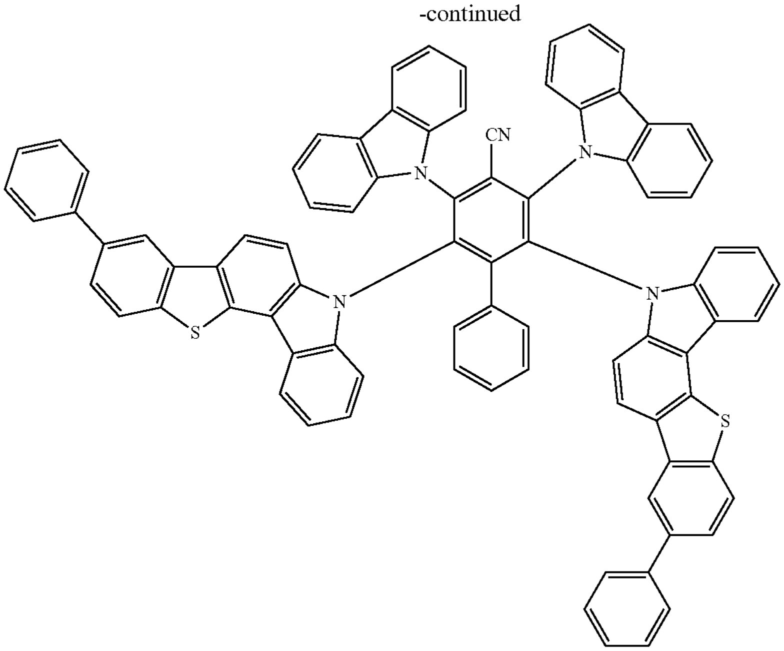

In one aspect of the present invention, only $R^2$ in the general formula (1) is a substituted ring-fused indol-1-yl group (the number of rings constituting the fused ring is 4 or more), and $R^1$, $R^4$, and $R^5$ are other donor groups. In a preferred aspect of the present invention, the compound represented by the general formula (1) is selected from the following group of compounds.

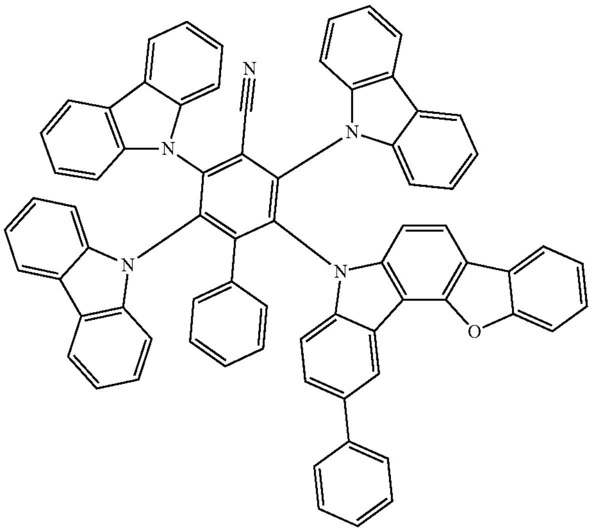

-continued
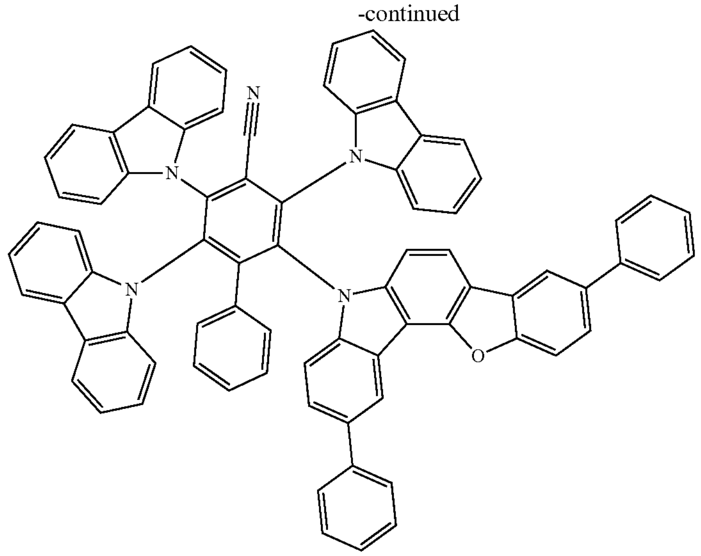
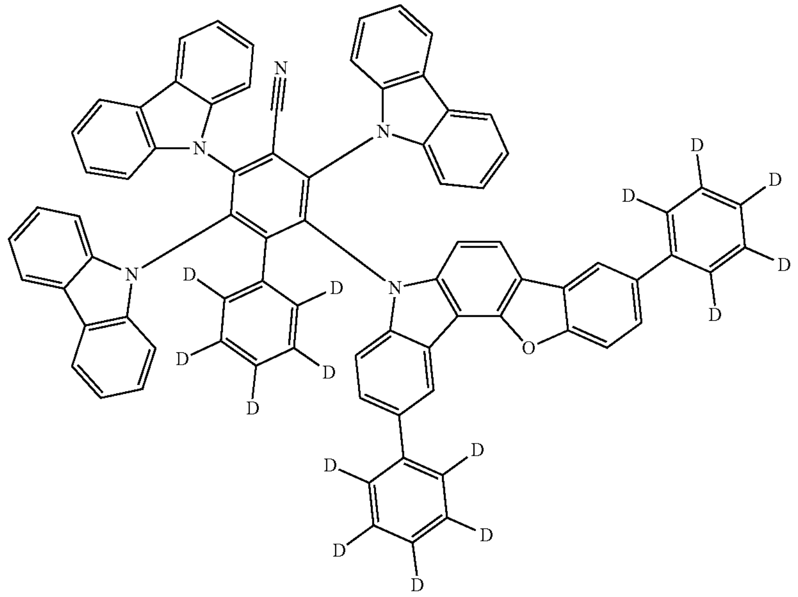
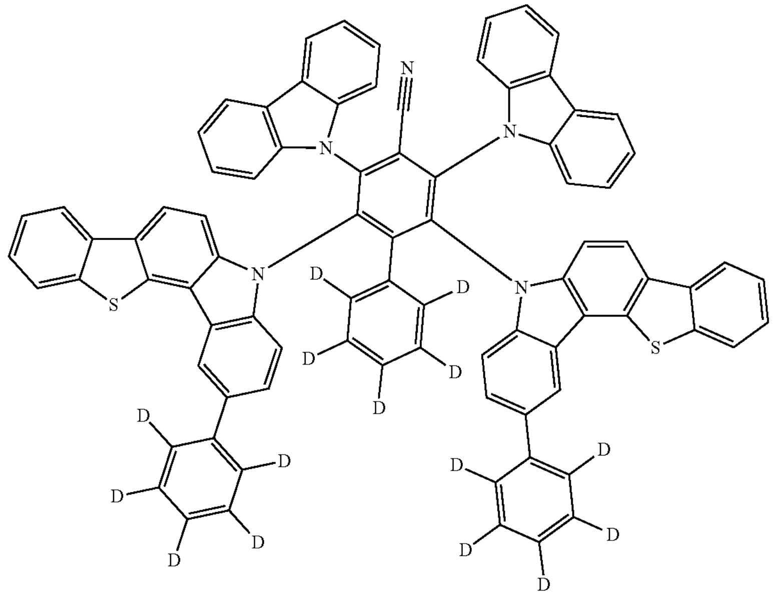

-continued
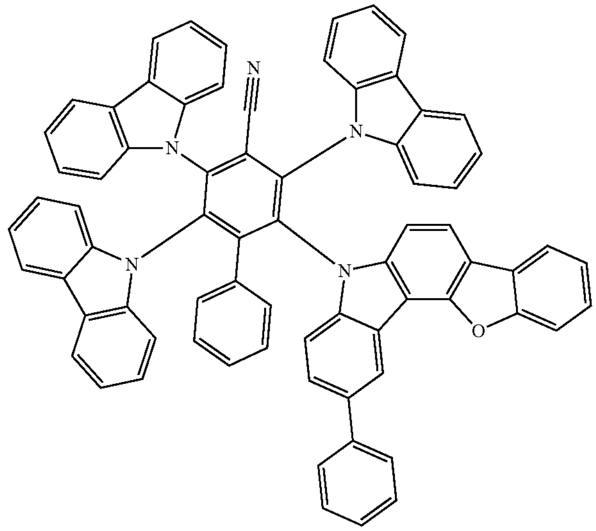
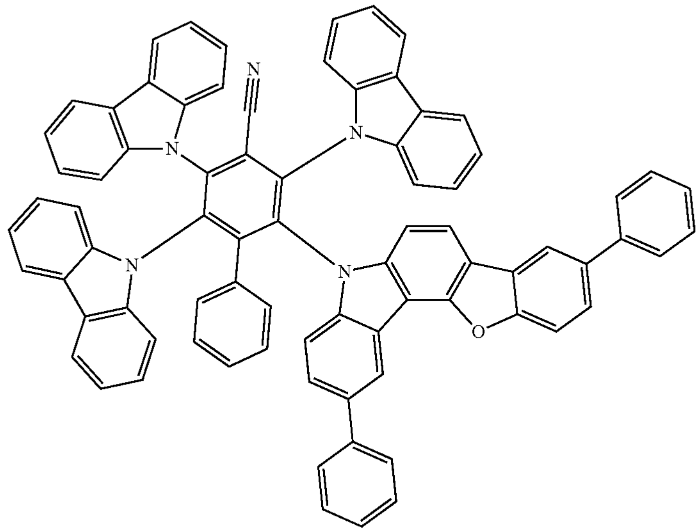
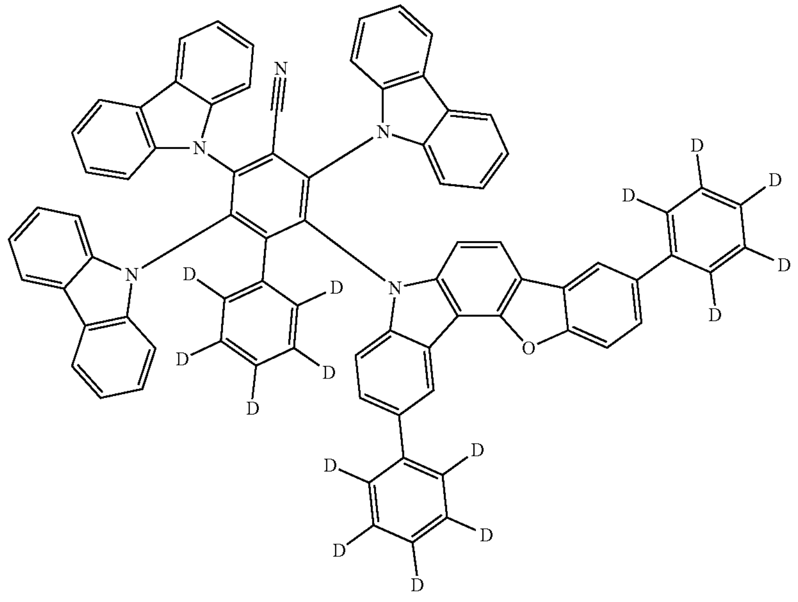

The molecular weight of the compound represented by the general formula (1) is preferably 1500 or less, more preferably 1200 or less, still more preferably 1000 or less, and even more preferably 900 or less, for example, in the case where an organic layer containing the compound represented by the general formula (1) is intended to be film-formed and used by a vapor deposition method. The lower limit of the molecular weight is the molecular weight of the minimum compound represented by the general formula (1).

The compound represented by the general formula (1) may be formed into a film by a coating method regardless of the molecular weight. When the coating method is used, even a compound having a relatively large molecular weight can be formed into a film. The compound represented by the general formula (1) has an advantage of being easily dissolved in an organic solvent. For this reason, the compound represented by the general formula (1) is easily applicable to a coating method and is easily purified to increase its purity.

It is also conceivable to use a compound containing a plurality of strictures represented by the general formula (1) in a molecule as a light emitting material by applying the present invention.

For example, a polymer obtained by allowing a polymerizable group to be present in the structure represented by the general formula (1) in advance and polymerizing the polymerizable group may be used as the light emitting material. For example, a polymer having a repeating unit may be obtained by preparing a monomer containing a polymerizable functional group at any site of the general formula (1) and polymerizing the monomer alone or copolymerizing the monomer with another monomer, and the polymer may be used as the light emitting material. Alternatively, it is also conceivable to obtain a dimer or a trimer by coupling compounds having a structure represented by the general formula (1) to each other and to use the dimer or the trimer as a light emitting material.

Examples of the polymer having a repeating unit containing a structure represented by the general formula (1) include polymers containing a structure represented by any one of the following two general formulae.

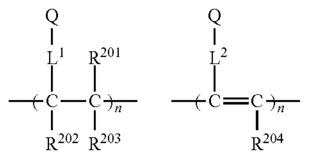

In the above general formulae, Q represents a group containing the structure represented by the general formula (1), and $L^1$ and $L^2$ represent a linking group. The linking group preferably has 0 to 20 carbon atoms, more preferably 1 to 15 carbon atoms, and still more preferably 2 to 10 carbon atoms. The linking group preferably has a structure represented by $—X^{11}\text{-}L^{11}\text{-}$. Here, $X^{11}$ represents an oxygen atom or a sulfur atom, and is preferably an oxygen atom. $L^{11}$ represents a linking group, and is preferably a substituted or unsubstituted alkylene group or a substituted or unsubstituted arylene group, and more preferably a substituted or unsubstituted alkylene group having 1 to 10 carbon atoms or a substituted or unsubstituted phenylene group.

In the above general formulae, $R^{201}$, $R^{202}$, $R^{203}$ and $R^{204}$ each independently represent a substituent. It is preferably a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom, or a chlorine atom, and still more preferably an unsubstituted alkyl group having 1 to 3 carbon atoms or an unsubstituted alkoxy group having 1 to 3 carbon atoms.

The linking group represented by $L^1$ and $L^2$ can be bonded to any site of the general formula (1) constituting Q. Two or more linking groups may be linked to one Q to form a cross-linked structure or a network structure.

Specific structural examples of the repeating unit include structures represented by the following formulae.

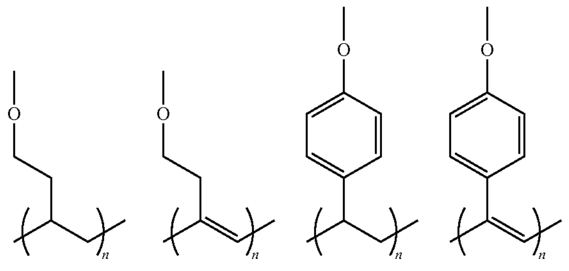

The polymer having a repeating unit including these formulae can be synthesized by introducing a hydroxy group into any site of the general formula (1), reacting the following compound using the hydroxy group as a linker to introduce a polymerizable group, and polymerizing the polymerizable group.

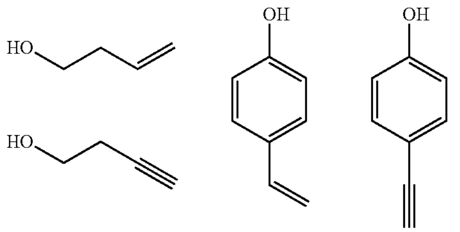

The polymer having a structure represented by the general formula (1) in the molecule can be a polymer having only a repeating unit that has the structure represented by the general formula (1), or can be a polymer containing a repeating unit that has any other structure. The repeating unit having the structure represented by the general formula (1) to be contained in the polymer may be a single kind or two or more kinds. The repeating unit not having the structure of the general formula (1) includes those derived from monomers used in general copolymerization. For example, it includes repeating units derived from monomers having an ethylenically unsaturated bond, such as ethylene or styrene.

In some embodiments, the compound represented by the general formula (1) is a light emitting material.

In some embodiments, the compound represented by the general formula (1) is a compound capable of emitting delayed fluorescence.

In some embodiments of the present disclosure, the compound represented by the general formula (1) is, when excited thermally or by an electronic means, able to emit light in a UV region, emit light of blue, green, yellow, orange, or red in a visible region (e.g., about 420 nm to about 500 un, about 500 nm to about 600 nm, or about 600 nm to about 700 nm) or in a near IR region.

In some embodiments of the present disclosure, the compound represented by the general formula (1) is, when excited thermally or by an electronic means, able to emit light of red or orange in a visible region (e.g., about 620 nm to about 780 nm, about 650 nm).

In some embodiments of the present disclosure, the compound represented by the general formula (1) is, when excited thermally or by an electronic means, able to emit light of orange or yellow in a visible region (e.g., about 570 nm to about 620 nm, about 590 nm, about 570 nm).

In some embodiments of the present disclosure, the compound represented by the general formula (1) is, when excited thermally or by an electronic means, able to emit light of green in a visible region (e.g., about 490 nm to about 575 nm, about 510 nm).

In some embodiments of the present disclosure, the compound represented by the general formula (1) is, when excited thermally or by an electronic means, able to emit light of blue in a visible region (e.g., about 400 nm to about 490 nm, about 475 nm).

In some embodiments of the present disclosure, the compound represented by the general formula (1) is, when excited thermally or by an electronic means, able to emit light in a IV region (e.g., about 280 to 400 nm).

In some embodiments of the present disclosure, the compound represented by the general formula (1) is, when excited thermally or by an electronic means, able to emit light in an IR region (e.g., about 780 nm to 2 μm).

In some embodiments of the present disclosure, an organic semiconductor device using the compound represented by the general formula (1) can be produced. The organic semiconductor device referred to herein may be an organic optical device in which light is interposed or an organic device in which light is not interposed. The organic optical device may be an organic light emitting device in which the device emits light, an organic light receiving device in which the device receives light, or a device in which energy transfer by light occurs in the device. In some embodiments of the present disclosure, an organic optical device such as an organic electroluminescent device or a solid-state imaging device (for example, a CMOS image sensor) can be produced by using the compound represented by the general formula (1). In some embodiments of the present disclosure, a CMOS (complementary metal-oxide semiconductor) or the like using the compound represented by the general formula (1) can be produced.

Electronic characteristics of small-molecule chemical substance libraries can be calculated by known ab initio quantum chemistry calculation. For example, according to time-dependent density functional theory calculation using 6-31G* as a basis, and a functional group known as Becke's three parameters, Lee-Yang-Parr hybrid functionals, the Hartree-Fock equation (TD-DFT/B3LYP/6-31G*) is analyzed and molecular fractions (parts) having HOMO not lower than a specific threshold value and LUMO not higher than a specific threshold value can be screened.

With that, for example, in the presence of a HOMO energy (for example, ionizing potential) of −6.5 eV or more, a donor part ("D") can be selected. On the other hand, for example, in the presence of a LUMO energy (for example, electron affinity) of −0.5 eV or less, an acceptor part ("A") can be selected. Abridge part ("B") is a strong conjugated system, for example, capable of strictly limiting the acceptor part and the donor part in a specific three-dimensional configuration, and therefore prevents the donor part and the acceptor part from overlapping in the pai-conjugated system.

In some embodiments, a compound library is screened using at least one of the following characteristics.

1. Light emission around a specific wavelength.
2. A triplet state over a calculated specific energy level.
3. $\Delta E_{ST}$ value lower than a specific value.
4. Quantum yield more than a specific value.
5. HOMO level.
6. LUMO level.

In some embodiments, the difference ($\Delta E_{ST}$) between the lowest singlet excited state and the lowest triplet excited state at 77 K is less than about 0.5 eV, less than about 0.4 eV, less than about 0.3 eV, less than about 0.2 eV, or less than about 0.1 eV In some embodiments, $\Delta E_{ST}$ value is less than about 0.09 eV, less than about 0.08 eV, less than about 0.07 eV, less than about 0.06 eV, less than about 0.05 eV, less than about 0.04 eV, less than about 0.03 eV, less than about 0.02 eV, or less than about 0.01 eV.

In some embodiments, the compound represented by the general formula (1) shows a quantum yield of more than 25%, for example, about 30%, about 35%, about 40%, about 45%, about 50%, about 55%, about 60%, about 65%, about 70%, about 75%, about 80%, about 85%, about 90%, about 95% or more.

[Method for Synthesizing Compound Represented by General Formula (1)]

The compound represented by the general formula (1) includes a novel compound.

The compound represented by the general formula (1) can be synthesized by combining known reactions. For example, by reacting cyanobenzene having an alkyl group and a halogen atom with a substituted or unsubstituted carbazole, the compound represented by the general formula (1) substituted with a substituted or unsubstituted carbazol-9-yl group can be synthesized. For details of the reaction conditions, Synthesis Examples described later can be referred to.

[Structure Using Compound Represented by General Formula (1)]

In some embodiments, the compound represented by the general formula (1) is used along with one or more materials (e.g., small molecules, polymers, metals, metal complexes), by combining them, or by dispersing the compound, or by covalent-bonding with the compound, or by coating with the compound, or by carrying the compound, or by associating with the compound, and solid films or layers are formed. For example, by combining the compound represented by the general formula (1) with an electroactive material, a film can be formed. In some cases, the compound represented by the general formula (1) can be combined with a hole transporting polymer. In some cases, the compound represented by the general formula (1) can be combined with an electron transporting polymer. In some cases, the compound represented by the general formula (1) can be combined with a hole transporting polymer and an electron transporting polymer. In some cases, the compound represented by the general formula (1) can be combined with a copolymer having both a hole transporting moiety and an electron transporting moiety In the embodiments mentioned above, the electrons and/or the holes formed in a solid film or layer can be interacted with the compound represented by the general formula (1).

[Film Formation]

In some embodiments, a film containing the compound represented by the general formula (1) can be formed in a wet process. In a wet process, a solution prepared by dissolving a composition containing the compound of the present invention is applied onto a surface, and then the solvent is removed to form a film. The wet process includes a spin coating method, a slit coating method, an ink jet method (a spraying method), a gravure printing method, an offset printing method and flexographic printing method, which, however are not limitative. In the wet process, an appropriate organic solvent capable of dissolving a composition containing the compound of the present invention is selected and used. In some embodiments, a substituent (e.g., an alkyl group) capable of increasing the solubility in an organic solvent can be introduced into the compound contained in the composition.

In some embodiments, a film containing the compound of the present invention can be formed in a dry process. In some embodiments, a vacuum deposition method is employable as a dry process, which, however, is not limitative. In the case where a vacuum deposition method is employed, compounds to constitute a film can be vapor co-deposited from individual vapor deposition sources, or can be vapor co-deposited from a single vapor deposition source formed by mixing the compounds. In the case where a single vapor deposition source is used, a mixed powder prepared by mixing compound powders can be used, or a compression molded body prepared by compression-molding the mixed powder can be used, or a mixture prepared by heating and melting the constituent compounds and cooling the resulting melt can be used. In some embodiments, by vapor co-deposition under the condition where the vapor deposition rate (weight reduction rate) of the plural compounds contained in a single vapor deposition source is the same or is nearly the same, a film having a compositional ratio corresponding to the compositional ratio of the plural compounds contained in the vapor deposition source can be formed. When plural compounds are mixed in the same compositional ratio as the compositional ratio of the film to be formed to prepare a vapor deposition source, a film having a desired compositional ratio can be formed in a simplified manner. In some embodiments, the temperature at which the compounds to be vapor co-deposited have the same weight reduction ratio is specifically defined, and the temperature can be employed as the temperature of vapor co-deposition.

Use Examples of Compound Represented by General Formula (1)

The compound represented by the general formula (1) is useful as a material for an organic light emitting device. In particular, the compound is preferably used for an organic light emitting diode or the like.

Organic Light Emitting Diode:

One embodiment of the present invention relates to use of the compound represented by the general formula (1) of the present invention as a light emitting material for organic light emitting devices. In some embodiments, the compound represented by the general formula (1) of the present invention can be effectively used as a light emitting material in a light emitting layer in an organic light emitting device. In some embodiments, the compound represented by the general formula (1) of the present invention includes delayed fluorescence (delayed fluorescent material) that emits delayed fluorescence. In some embodiments, the present invention provides a delayed fluorescent material having a structure represented by the general formula (1) of the present invention. In some embodiments, the present invention relates to use of the compound represented by the general formula (1) of the present invention as a delayed fluorescent material. In some embodiments, the compound represented by the general formula (1) of the present invention can be used as a host material, and can be used along with one or more light emitting materials, and the light emitting material can be a fluorescent material, a phosphorescent material or a TADF. In some embodiments, the compound represented by the general formula (1) can be used as a hole transporting material. In some embodiments, the compound represented by the general formula (1) can be used as an electron transporting material. In some embodiments, the present invention relates to a method of generating delayed fluorescence from the compound represented by the general formula (1). In some embodiments, the organic light emitting device containing the compound as a light emitting material emits delayed fluorescence and shows a high light emission efficiency.

In some embodiments, the light emitting layer contains the compound represented by the general formula (1), and the compound represented by the general formula (1) is aligned in parallel to the substrate. In some embodiments, the substrate is a film-forming surface. In some embodiment, the alignment of the compound represented by the general formula (1) relative to the film-forming surface can have some influence on the propagation direction of light emitted by the aligned compounds, or can determine the direction. In some embodiments, by aligning the propagation direction of light emitted by the compound represented by the general formula (1), the light extraction efficiency from the light emitting layer can be improved.

One embodiment of the present invention relates to an organic light emitting device. In some embodiments, the organic light emitting device includes a light emitting layer. In some embodiments, the light emitting layer contains, as a light emitting material therein, the compound represented by the general formula (1). In some embodiments, the organic light emitting device is an organic photoluminescent device (organic PL device). In some embodiments, the organic light emitting device is an organic electroluminescent device (organic EL device). In some embodiments, the compound represented by the general formula (1) assists light irradiation from the other light emitting materials contained in the light emitting layer (as a so-called assist dopant). In some embodiments, the compound represented by the general formula (1) contained in the light emitting layer is in a lowest excited energy level, and is contained between the lowest excited single energy level of the host material contained in the light emitting layer and the lowest excited singlet energy level of the other light emitting materials contained in the light emitting layer.

In some embodiments, the organic photoluminescent device comprises at least one light emitting layer. In some embodiments, the organic electroluminescent device comprises at least an anode, a cathode, and an organic layer between the anode and the cathode. In some embodiments, the organic layer comprises at least a light emitting layer. In some embodiments, the organic layer comprises only a light emitting layer. In some embodiments, the organic layer comprises one or more organic layers in addition to the light emitting layer. Examples of the organic layer include a hole transporting layer, a hole injection layer, an electron barrier layer, a hole barrier layer, an electron injection layer, an electron transporting layer and an exciton barrier layer. In some embodiments, the hole transporting layer may be a hole injection and transporting layer having a hole injection function, and the electron transporting layer may be an electron injection and transporting layer having an electron injection function. An example of an organic electroluminescent device is shown in FIG. 1.

Light Emitting Layer:

In some embodiments, the light emitting layer is a layer where holes and electrons injected from the anode and the cathode, respectively, are recombined to form excitons. In some embodiments, the layer emits light.

In some embodiments, only a light emitting material is used as the light emitting layer. In some embodiments, the light emitting layer contains a light emitting material and a host material. In some embodiments, the light emitting material is one or more compounds of the general formula (1). In some embodiments, for improving luminous radiation efficiency of an organic electroluminescent device and an organic photoluminescence device, the singlet exciton and the triplet exciton generated in a light emitting material is confined inside the light emitting material. In some embodiments, a host material is used in the light emitting layer in addition to a light emitting material therein. In some embodiments, the host material is an organic compound. In some embodiments, the organic compound has an excited singlet energy and an excited triplet energy, and at least one of them is higher than those in the light emitting material of the present invention. In some embodiments, the singlet exciton and the triplet exciton generated in the light emitting material of the present invention are confined in the molecules of the light emitting material of the present invention. In some embodiments, the singlet and triplet excitons are fully confined for improving luminous radiation efficiency. In some embodiments, although high luminous radiation efficiency is still attained, singlet excitons and triplet excitons are not fully confined, that is, a host material capable of attaining high luminous radiation efficiency can be used in the present invention with no specific limitation. In some embodiments, in the light emitting material in the light emitting layer of the device of the present invention, luminous radiation occurs. In some embodiments, radiated light includes both fluorescence and delayed fluorescence. In some embodiments, radiated light includes radiated light from a host material. In some embodiments, radiated light is composed of radiated light from a host material. In some embodiments, radiated light includes radiated light from the compound represented by the general formula (1) and radiated light from a host material. In some embodiment, a TADF molecule and a host material are used. In some embodiments, TADF is an assist dopant and has a lower excited singlet energy than the host material in the light emitting layer and a higher excited singlet energy than the light emitting material in the light emitting layer.

In the case where the compound of the general formula (1) is used as an assist dopant, various compounds can be employed as a light emitting material (preferably a fluorescent material). As such light emitting materials, employable are an anthracene derivative, a tetracene derivative, a naphthacene derivative, a pyrene derivative, a perylene derivative, a chrysene derivative, a rubrene derivative, a coumarin derivative, a pyran derivative, a stilbene derivative, a fluorenone derivative, an anthryl derivative, a pyrromethene derivative, a terphenyl derivative, a terphenylene derivative, a fluoranthene derivative, an amine derivative, a quinacridone derivative, an oxadiazole derivative, a malononitrile derivative, a pyran derivative, a carbazole derivative, a julolidine derivative, a thiazole derivative, and a metal (Al, Zn)-having derivative. These exemplified skeletons can have a substituent, or may not have a substituent. These exemplified skeletons can be combined.

Light emitting materials that can be used in combination with the assist dopant represented by the general formula (1) are shown below.

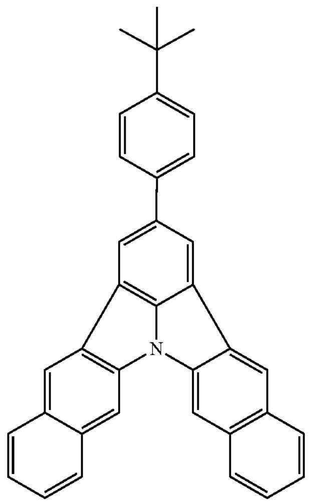

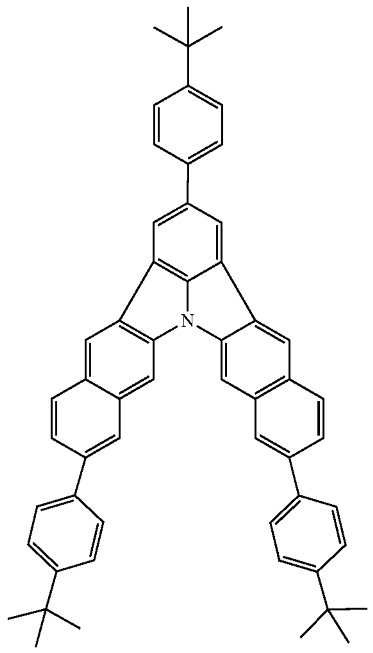

-continued
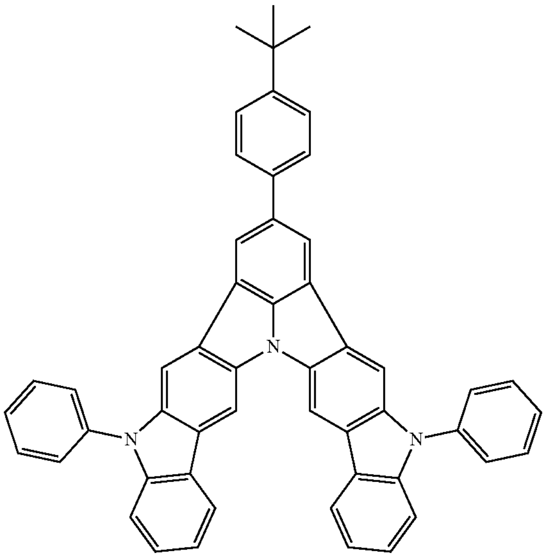
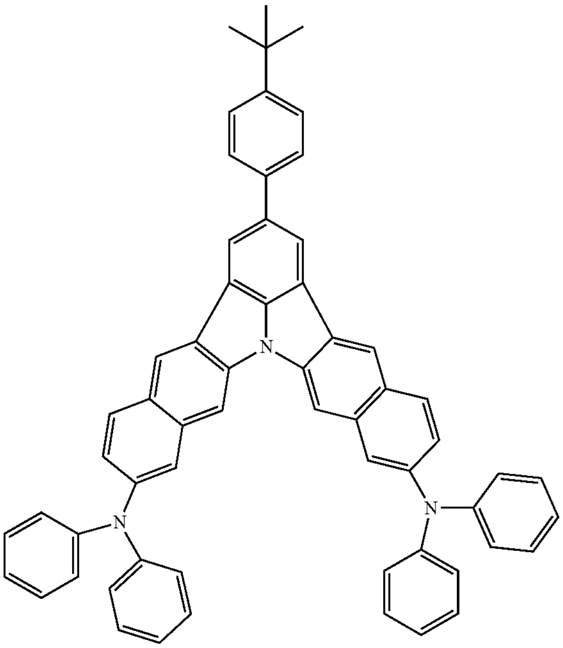
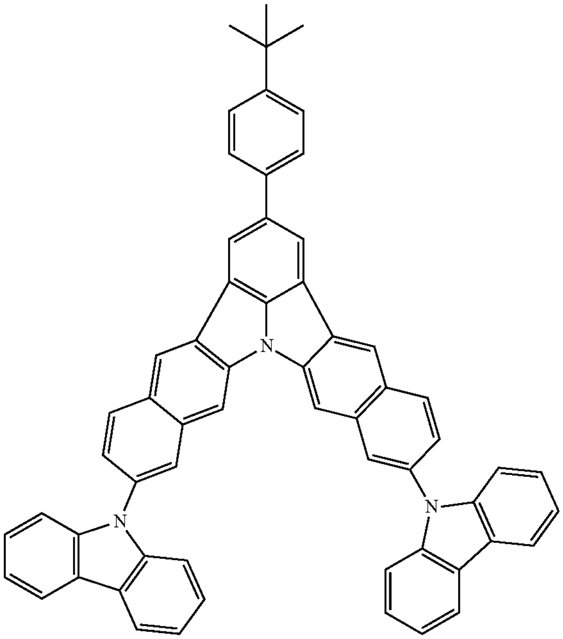
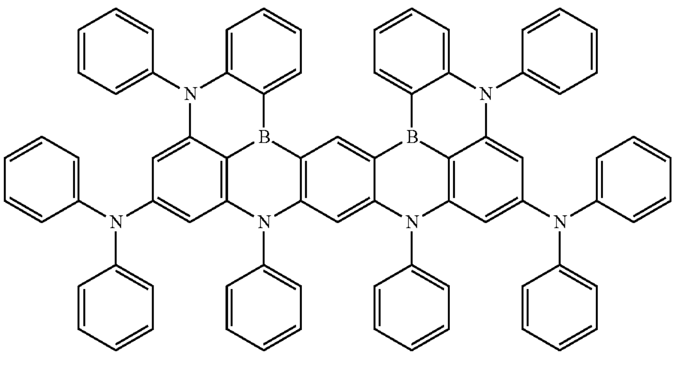
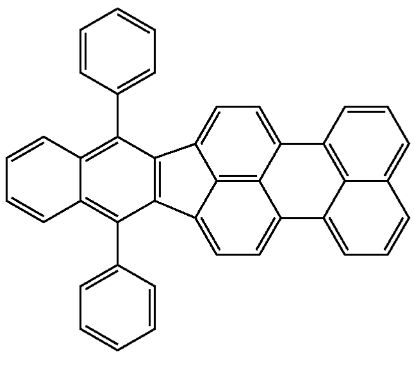

-continued
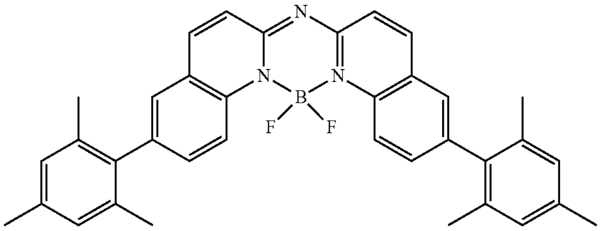
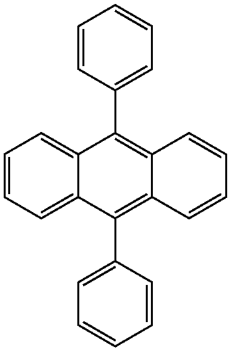
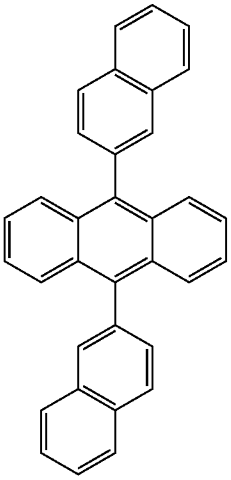
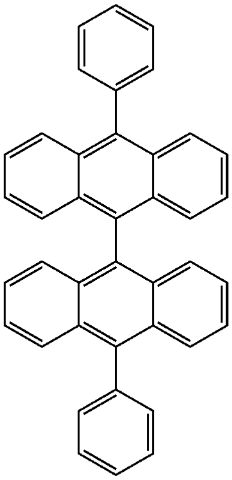
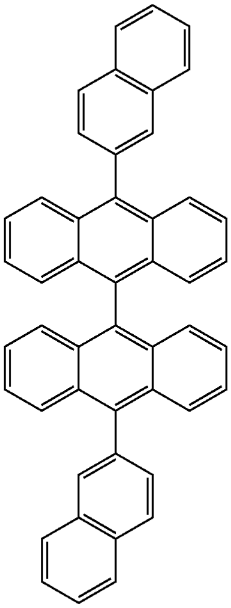
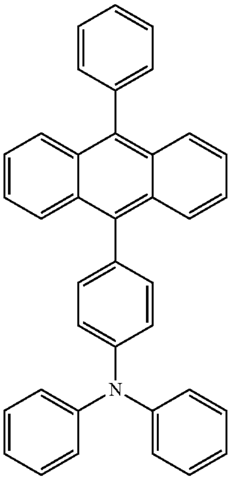
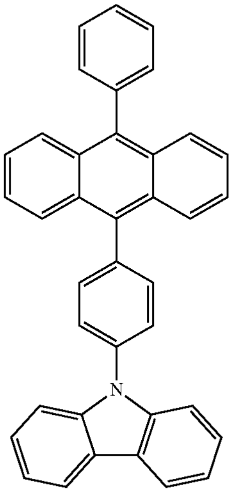
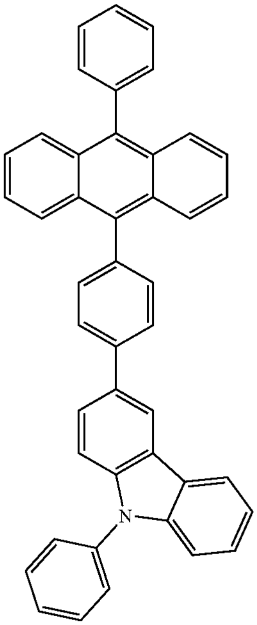
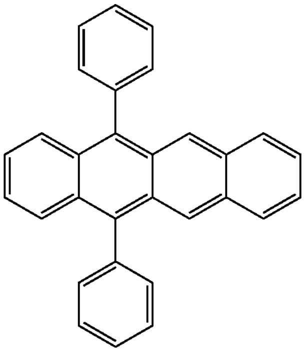
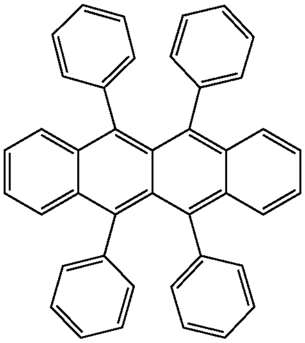

-continued
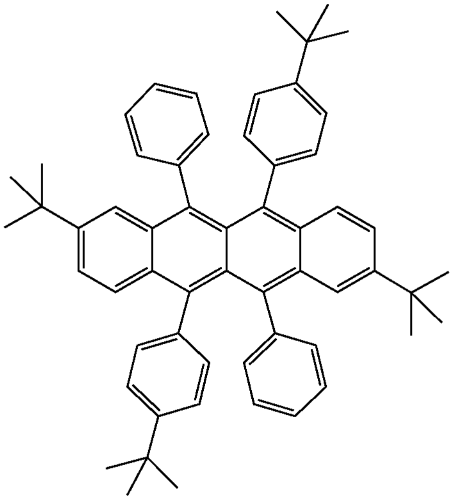
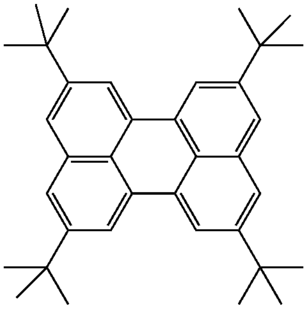
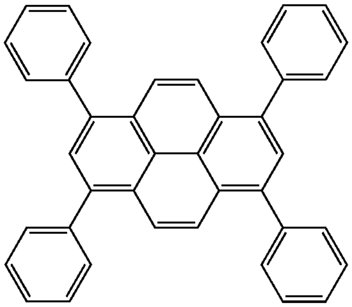
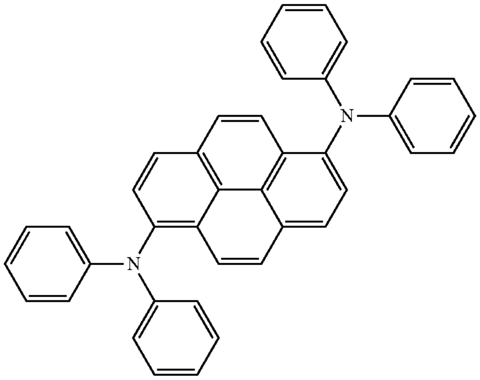
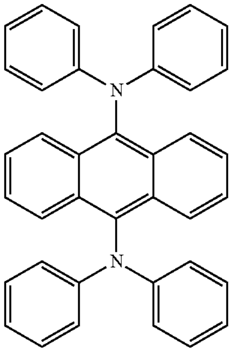
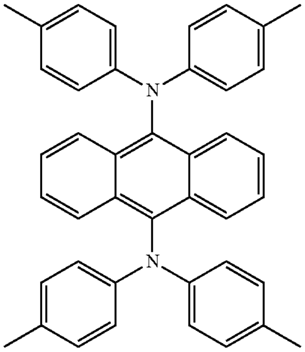
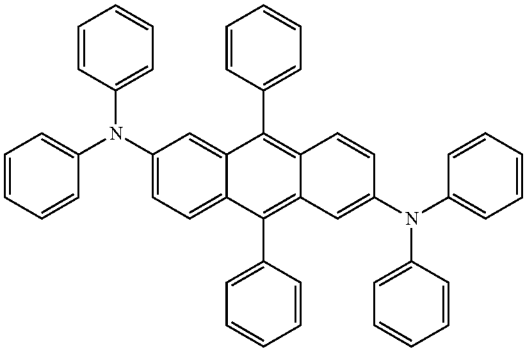
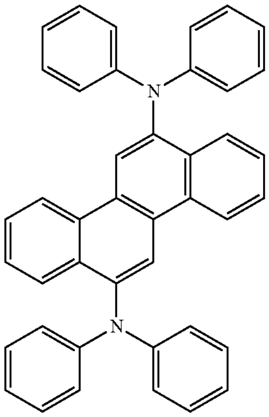
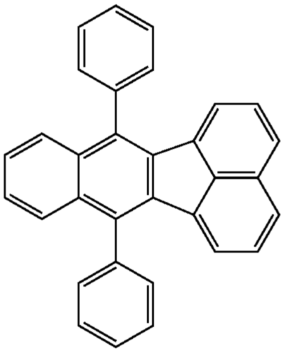
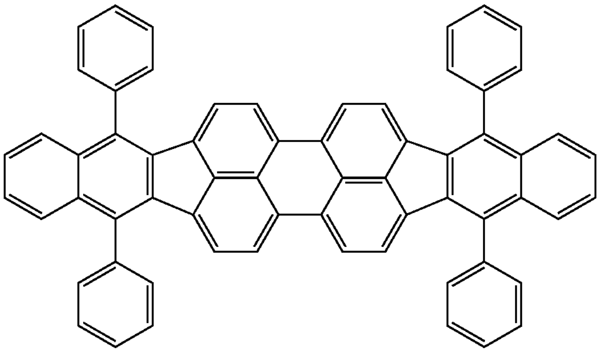

-continued

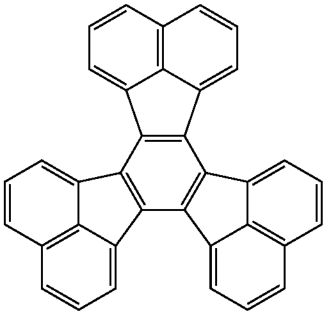

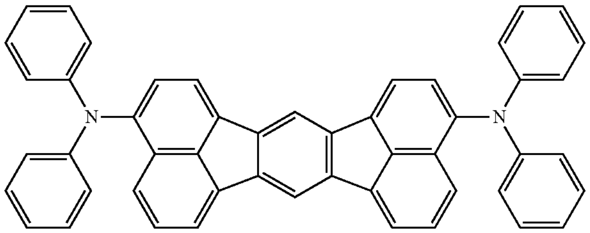

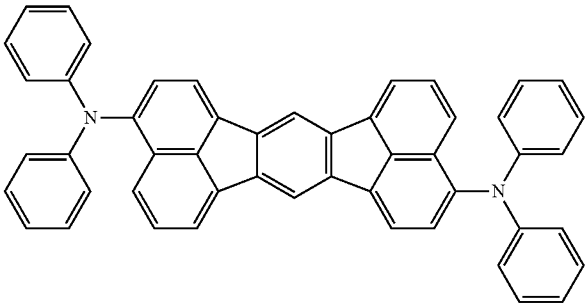

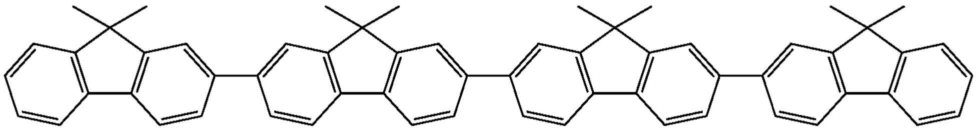

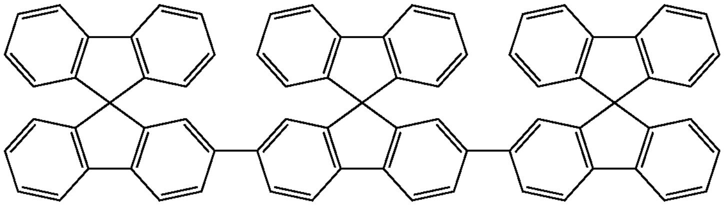

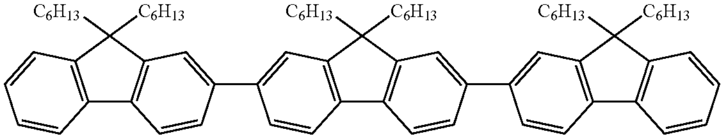

In addition, the compounds described in WO2015/022974, paragraphs 0220 to 0239 are also especially favorably employable as a light emitting material for use along with the assist dopant represented by the general formula (1).

In some embodiments where a host material is used, the amount of the compound of the present invention contained in a light emitting layer as a light emitting material is 0.1% by weight or more. In some embodiments where a host material is used, the amount of the compound of the present invention contained in a light emitting layer as a light emitting material is 1% by weight or more. In some embodiments where a host material is used, the amount of the compound of the present invention contained in a light emitting layer as a light emitting material is 50% by weight or less. In some embodiments where a host material is used, the amount of the compound of the present invention contained in a light emitting layer as a light emitting material is 20% by weight or less. In some embodiments where a host material is used, the amount of the compound of the present invention contained in a light emitting layer as a light emitting material is 10% by weight or less.

In some embodiments, the host material in a light emitting layer is an organic compound having a hole transporting capability and an electron transporting capability. In some embodiments, the host material in a light emitting layer is an organic compound that prevents increase in the wavelength of emitted light. In some embodiments, the host material in a light emitting layer is an organic compound having a high glass transition temperature.

In some embodiments, the host material is selected from the following group:

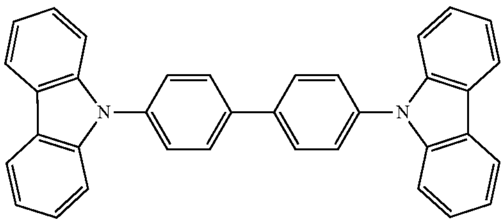

-continued
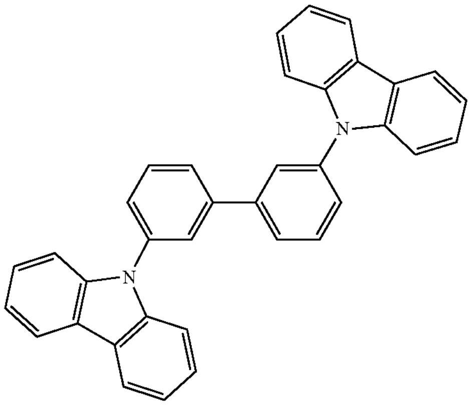
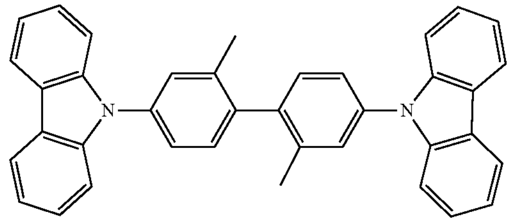
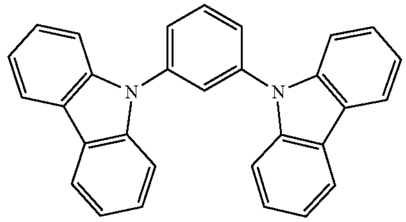
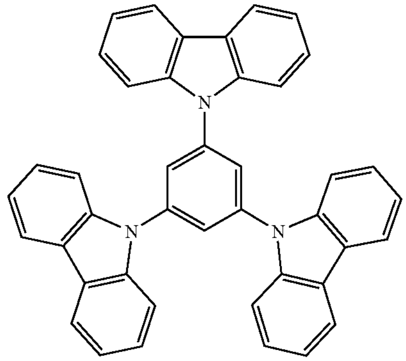
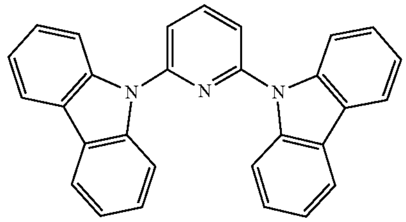
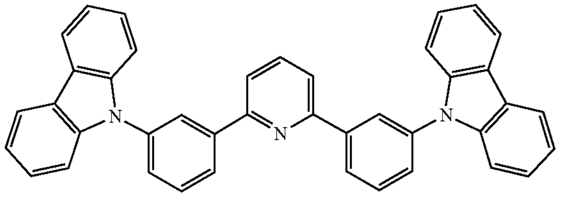
-continued
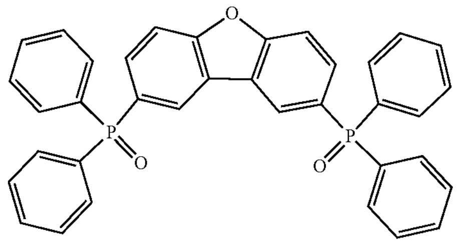
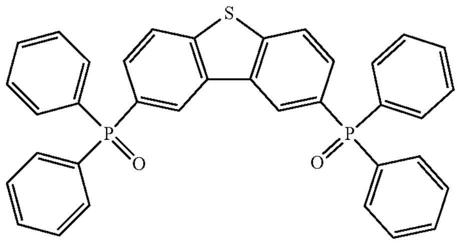
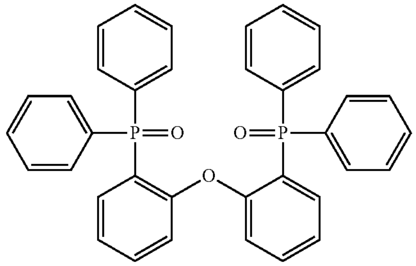
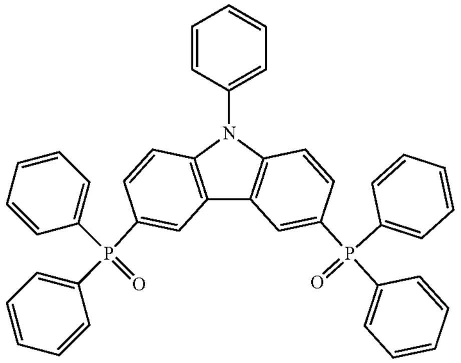
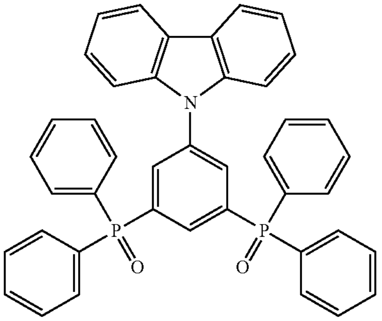
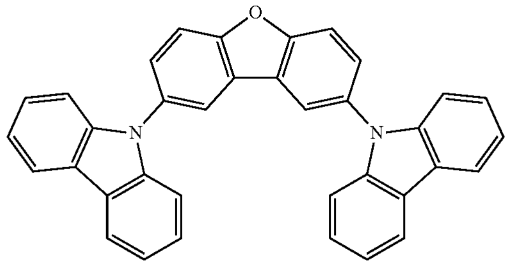

-continued
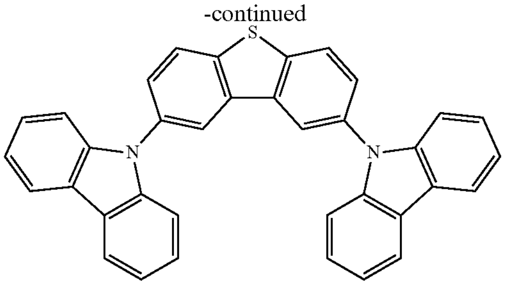
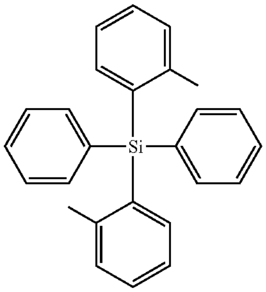
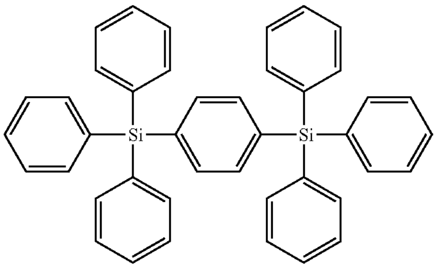
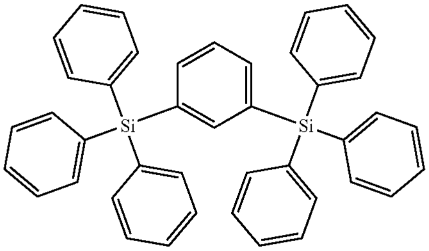
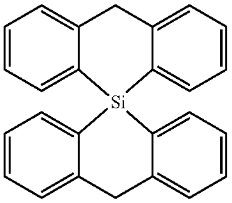
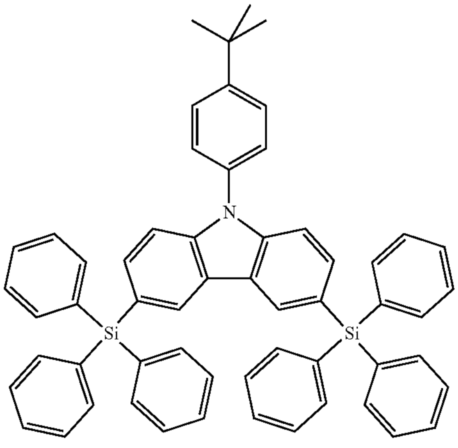
-continued
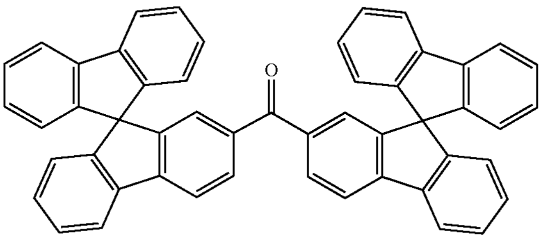
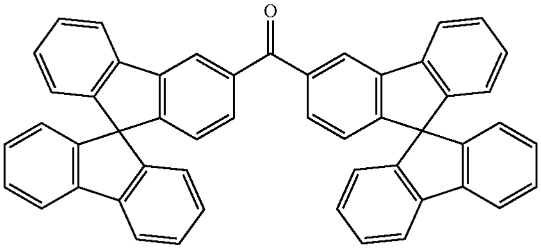
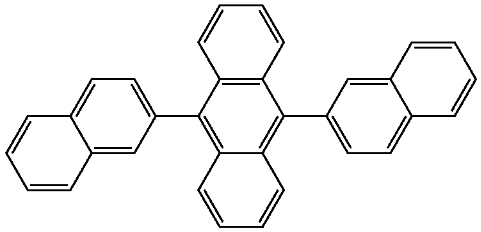
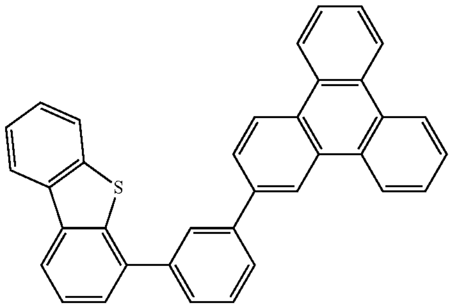
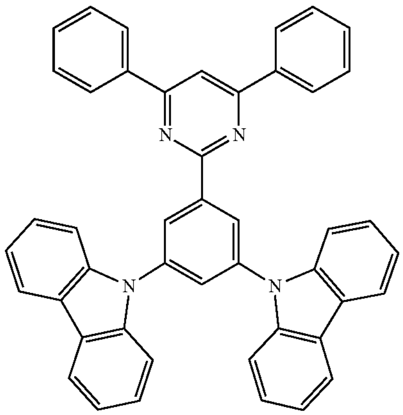

-continued

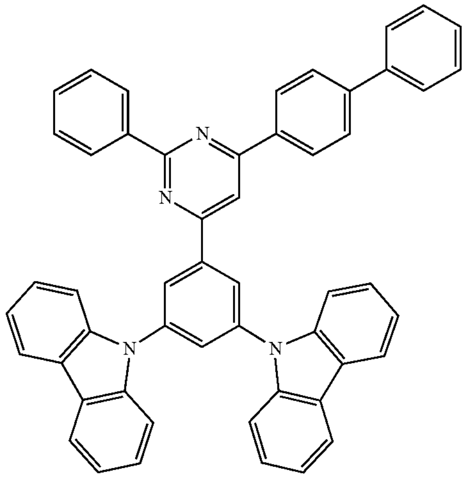

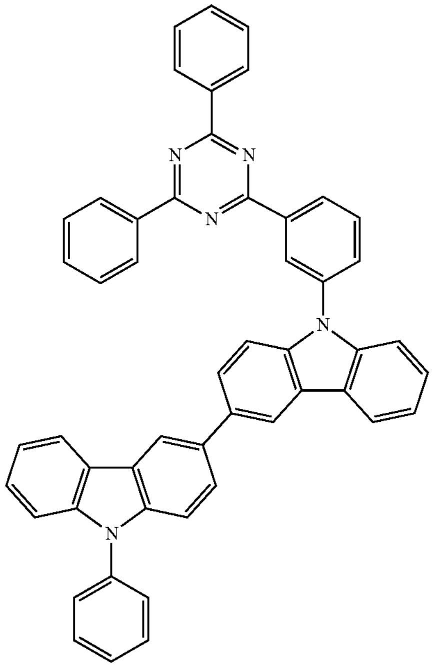

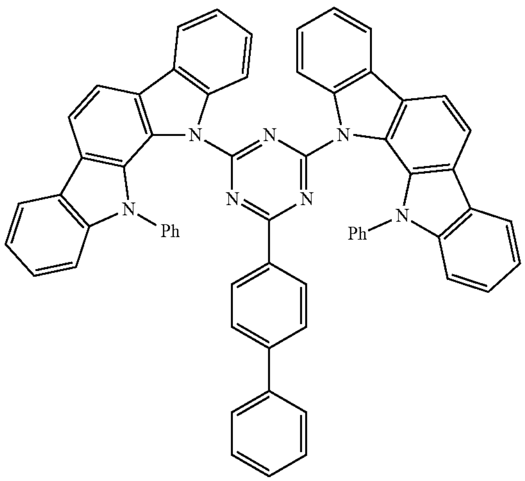

-continued

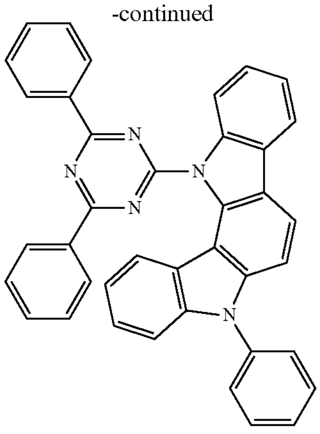

In some embodiments, the light emitting layer contains two or more kinds of TADF molecules differing in the structure. For example, the light emitting layer can contain three kinds of materials of a host material, a first TADF molecule and a second TADF molecule whose excited singlet energy level is higher in that order. In that case, both the first TADF molecule and the second TADF molecule are preferably such that the difference $\Delta E_{ST}$ between the lowest excited single energy level and the lowest excited triplet energy level at 77 K is 0.3 eV or less, more preferably 0.25 eV or less, even more preferably 0.2 eV or less, further more preferably 0.15 eV or less, further more preferably 0.1 eV or less, further more preferably 0.07 eV or less, further more preferably 0.05 eV or less, further more preferably 0.03 eV or less, further more preferably 0.01 eV or less. The content of the first TADF molecule in the light emitting layer is preferably larger than the content of the second TADF molecule therein. The content of the host material in the light emitting layer is preferably larger than the content of the second TADF molecule therein. The content of the first TADF molecule in the light emitting layer can be larger than or can be smaller than or can be the same as the content of the host material therein. In some embodiments, the composition in the light emitting layer can be 10 to 70% by weight of a host material, 10 to 80% by weight of a first TADF molecule, and 0.1 to 30% by weighty of a second TADF molecule. In some embodiments, the composition in the light emitting layer can be 20 to 45% by weight of a host material, 50 go 75% by weight of a first TADF molecule, and 5 to 20% by weighty of a second TADF molecule. In some embodiments, the emission quantum yield φPL1(A) by photo-excitation of a vapor co-deposited film of a first TADF molecule and a host material (the content of the first TADF molecule in the vapor co-deposited film=A % by weight) and the emission quantum yield φPL2(A) by photo-excitation of a vapor co-deposited film of a second TADF molecule and a host material (the content of the second TADF molecule in the vapor co-deposited film=A % by weight) satisfy a relational formula φPL1(A) φPL2(A). In some embodiments, the emission quantum yield φPL2(B) by photo-excitation of a vapor co-deposited film of a second TADF molecule and a host material (the content of the second TADF molecule in the vapor co-deposited film=B % by weight) and the emission quantum yield φPL2(100) by photo-excitation of a single film of a second TADF molecule satisfy a relational formula (PL2(B)>φPL2(100). In some embodiments, the light emitting layer can contain three kinds of TADF molecules differing in the structure. The compound of the present invention can be any of the plural TADF compounds contained in the light emitting layer.

In some embodiments, the light emitting layer can be composed of materials selected from the group consisting of a host material an assist dopant and a light emitting material. In some embodiments, the light emitting layer does not contain a metal element. In some embodiments, the light emitting layer can be formed of a material composed of atoms alone selected from the group consisting of a carbon atom, a hydrogen atom, a deuterium atom, a nitrogen atom, an oxygen atom and a sulfur atom. Or the light emitting layer can be formed of a material composed of atoms alone selected from the group consisting of a carbon atom, a hydrogen atom, a deuterium atom, a nitrogen atom and an oxygen atom. Or the light emitting layer can be formed of a material composed of atoms alone selected from the group consisting of a carbon atom, a hydrogen atom, a nitrogen atom and an oxygen atom.

In the case where the light emitting layer contain any other TADF material than the compound of the present invention, the TADF material can be a known delayed fluorescent material. As preferred delayed fluorescent materials, there can be mentioned compounds included in the general formulae described in WO2013/154064, paragraphs 0008 to 0048 and 0095 to 0133; WO2013/011954, paragraphs 0007 to 0047 and 0073 to 0085; WO2013/011955, paragraphs 0007 to 0033 and 0059 to 0066; WO2013/081088, paragraphs 0008 to 0071 and 0118 to 0133; JP 2013-256490 A, paragraphs 0009 to 0046 and 0093 to 0134; JP 2013-116975 A, paragraphs 0008 to 0020 and 0038 to 0040; WO2013/133359, paragraphs 0007 to 0032 and 0079 to 0084; WO2013/161437, paragraphs 0008 to 0054 and 0101 to 0121; JP 2014-9352 A, paragraphs 0007 to 0041 and 0060 to 0069; and JP 2014-9224 A, paragraphs 0008 to 0048 and 0067 to 0076; JP 2017-119663 A, paragraphs 0013 to 0025; JP 2017-119664 A, paragraphs 0013 to 0026; JP 2017-222623 A, paragraphs 0012 to 0025; JP 2017-226838 A, paragraphs 0010 to 0050; JP 2018-100411 A, paragraphs 0012 to 0043; WO2018/047853, paragraphs 0016 to 0044; and especially, exemplary compounds therein capable of emitting delayed fluorescence. In addition, also preferably employable here are light emitting materials capable of emitting delayed fluorescence, as described in JP 2013-253121 A, WO2013/133359, WO2014/034535, WO2014/115743, WO2014/122895, WO2014/126200, WO2014/136758, WO2014/133121, WO2014/136860, WO2014/196585, WO2014/189122, WO2014/168101, WO2015/008580, WO2014/203840, WO2015/002213, WO2015/016200, WO2015/019725, WO2015/072470, WO2015/108049, WO2015/080182, WO2015/072537, WO2015/080183, JP 2015-129240 A, WO2015/129714, WO2015/129715, WO2015/133501, WO2015/136880, WO2015/137244, WO2015/137202, WO2015/137136, WO2015/146541, and WO2015/159541. These patent publications described in this paragraph are hereby incorporated as a part of this description by reference.

In the following, the constituent members and the other layers than the light emitting layer of the organic electroluminescent device are described.

Substrate:

In some embodiments, the organic electroluminescent device of the invention is supported by a substrate, wherein the substrate is not particularly limited and may be any of those that have been commonly used in an organic electroluminescent device, for example those formed of glass, transparent plastics, quartz and silicon.

Anode

In some embodiments, the anode of the organic electroluminescent device is made of a metal, an alloy, an electroconductive compound, or a combination thereof. In some embodiments, the metal, alloy, or electroconductive compound has a large work function (4 eV or more). In some embodiments, the metal is Au. In some embodiments, the electroconductive transparent material is selected from CuI, indium tin oxide (ITO), $SnO_2$, and ZnO. In some embodiments, an amorphous material capable of forming a transparent electroconductive film, such as IDIXO ($In_2O_3$—ZnO), is be used. In some embodiments, the anode is a thin film. In some embodiments the thin film is made by vapor deposition or sputtering. In some embodiments, the film is patterned by a photolithography method. In some embodiments, where the pattern may not require high accuracy (for example, approximately 100 μm or more), the pattern may be formed with a mask having a desired shape on vapor deposition or sputtering of the electrode material. In some embodiments, when a material can be applied as a coating, such as an organic electroconductive compound, a wet film forming method, such as a printing method and a coating method is used. In some embodiments, when the emitted light goes through the anode, the anode has a transmittance of more than 10%, and the anode has a sheet resistance of several hundred Ohm per square or less. In some embodiments, the thickness of the anode is from 10 to 1,000 nm. In some embodiments, the thickness of the anode is from 10 to 200 nm. In some embodiments, the thickness of the anode varies depending on the material used.

Cathode

In some embodiments, the cathode is made of an electrode material a metal having a small work function (4 eV or less) (referred to as an electron injection metal), an alloy, an electroconductive compound, or a combination thereof. In some embodiments, the electrode material is selected from sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. In some embodiments, a mixture of an electron injection metal and a second metal that is a stable metal having a larger work function than the electron injection metal is used. In some embodiments, the mixture is selected from a magnesium-silver mixture, a magnesium-aluminum mixture, a magnesium-indium mixture, an aluminum-aluminum oxide ($Al_2O_3$) mixture, a lithium-aluminum mixture, and aluminum. In some embodiments, the mixture increases the electron injection property and the durability against oxidation. In some embodiments, the cathode is produced by forming the electrode material into a thin film by vapor deposition or sputtering. In some embodiments, the cathode has a sheet resistance of several hundred Ohm per square or less. In some embodiments, the thickness of the cathode ranges from 10 nm to 5 μm. In some embodiments, the thickness of the cathode ranges from 50 to 200 nm. In some embodiments, for transmitting the emitted light, any one of the anode and the cathode of the organic electroluminescent device is transparent or translucent. In some embodiments, the transparent or translucent electroluminescent devices enhances the light emission luminance.

In some embodiments, the cathode is formed with an electroconductive transparent material, as described for the anode, to form a transparent or translucent cathode. In some embodiments, a device comprises an anode and a cathode, both being transparent or translucent.

Injection Layer

An injection layer is a layer between the electrode and the organic layer. In some embodiments, the injection layer decreases the driving voltage and enhances the light emission luminance. In some embodiments the injection layer includes a hole injection layer and an electron injection layer. The injection layer can be positioned between the anode and the light emitting layer or the hole transporting layer, and between the cathode and the light emitting layer or the electron transporting layer. In some embodiments, an injection layer is present. In some embodiments, no injection layer is present.

Preferred compound examples for use as a hole injection material are shown below.

$MoO_3$,

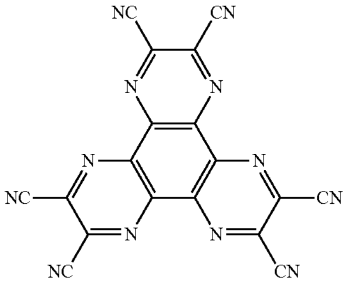

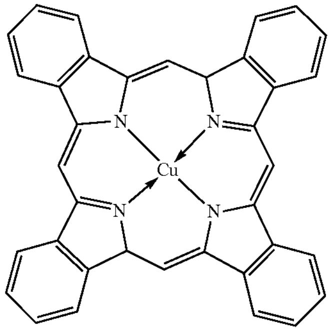

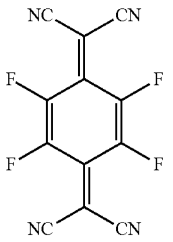

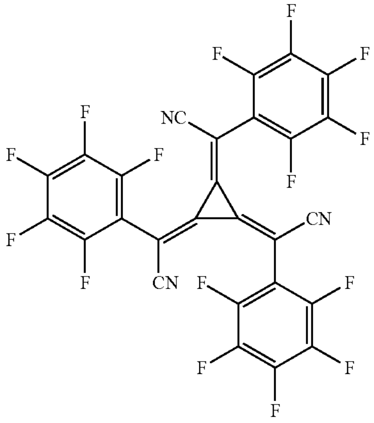

-continued

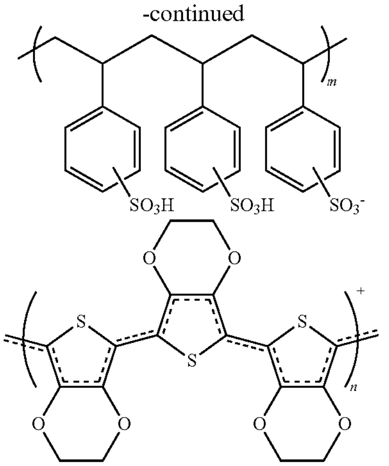

Next, preferred compound examples for use as an electron injection material are shown below.

LiF, CsF,

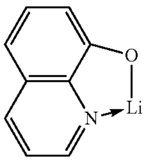

Barrier Layer

A barrier layer is a layer capable of inhibiting charges (electrons or holes) and/or excitons present in the light emitting layer from being diffused outside the light emitting layer. In some embodiments, the electron barrier layer is between the light emitting layer and the hole transporting layer, and inhibits electrons from passing through the light emitting layer toward the hole transporting layer. In some embodiments, the hole barrier layer is between the light emitting layer and the electron transporting layer, and inhibits holes from passing through the light emitting layer toward the electron transporting layer. In some embodiments, the barrier layer inhibits excitons from being diffused outside the light emitting layer. In some embodiments, the electron barrier layer and the hole barrier layer are exciton barrier layers. As used herein, the term "electron barrier layer" or "exciton barrier layer" includes a layer that has the functions of both electron barrier layer and of an exciton barrier layer.

Hole Barrier Layer

A hole barrier layer acts as an electron transporting layer. In some embodiments, the hole barrier layer inhibits holes from reaching the electron transporting layer while transporting electrons. In some embodiments, the hole barrier layer enhances the recombination probability of electrons and holes in the light emitting layer. The material for the hole barrier layer may be the same materials as the ones described for the electron transporting layer.

Preferred compound examples for use for the hole barrier layer are shown below.

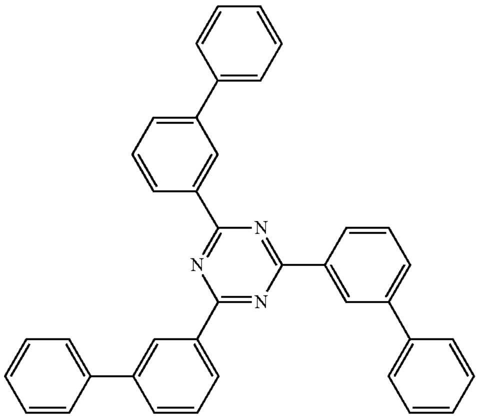

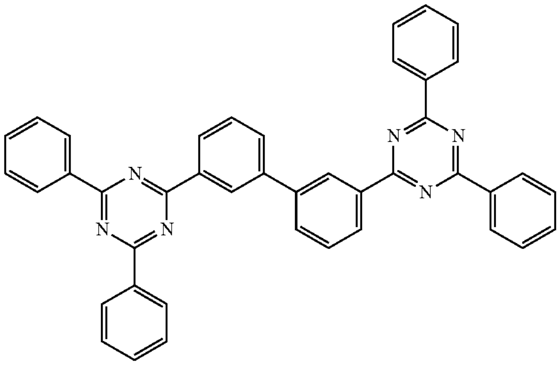

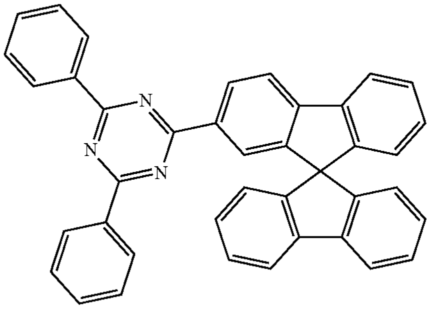

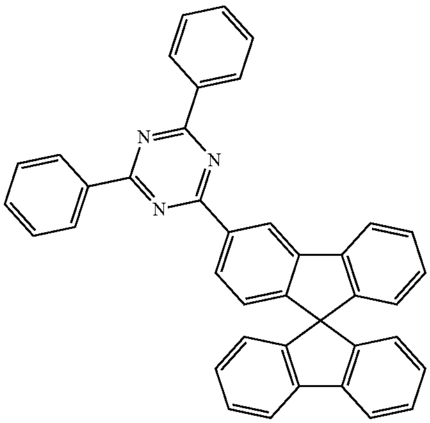

-continued

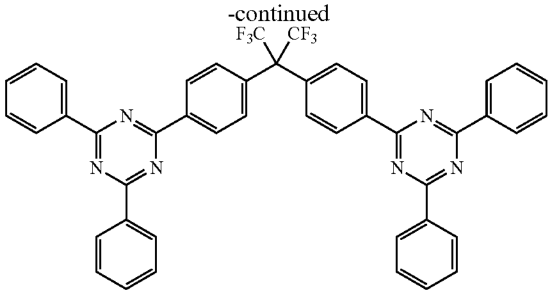

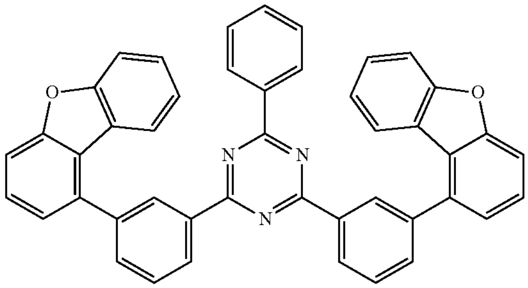

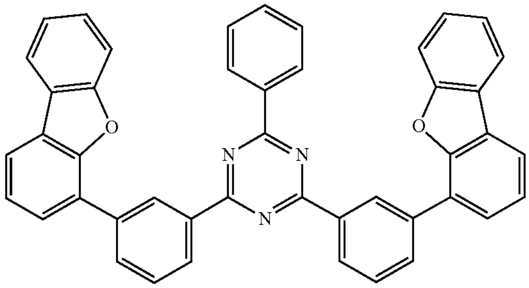

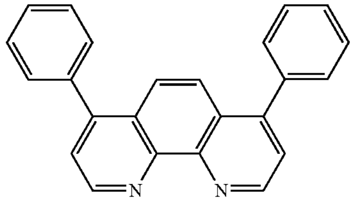

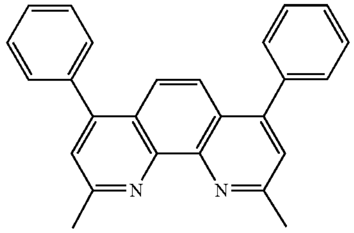

Electron Barrier Layer

As electron barrier layer transports holes. In some embodiments, the electron barrier layer inhibits electrons from reaching the hole transporting layer while transporting holes. In some embodiments, the electron barrier layer enhances the recombination probability of electrons and holes in the light emitting layer. The material used for the electron barrier layer may be the same material as the ones described above for the hole transporting layer.

Preferred compound examples for use as the electron barrier material are shown below.

-continued
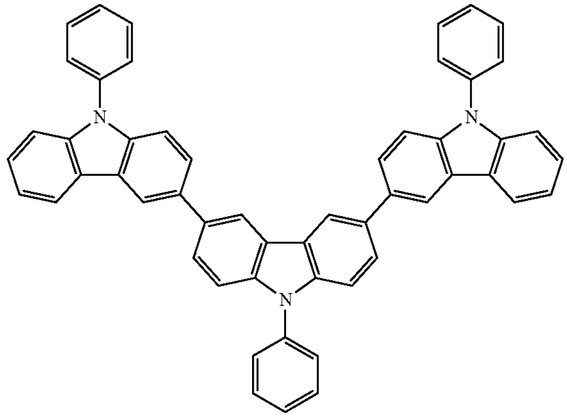
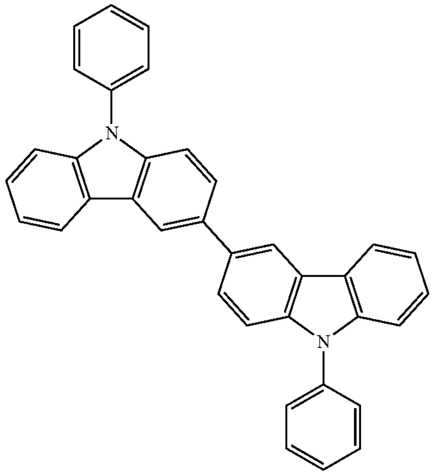
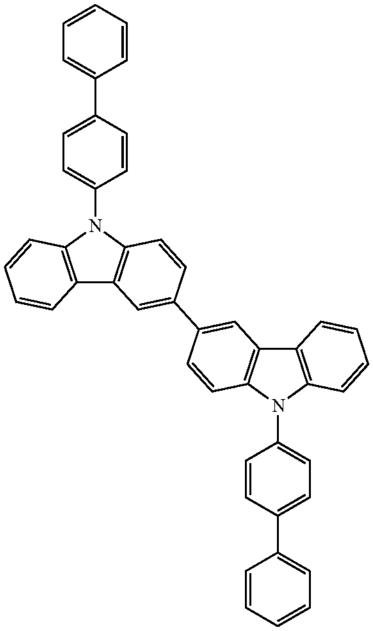
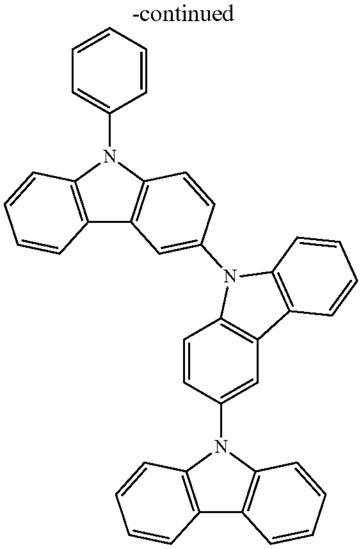
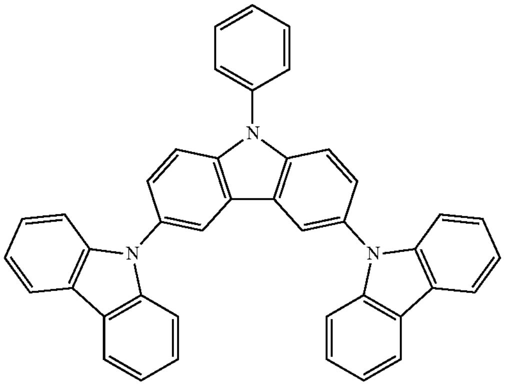
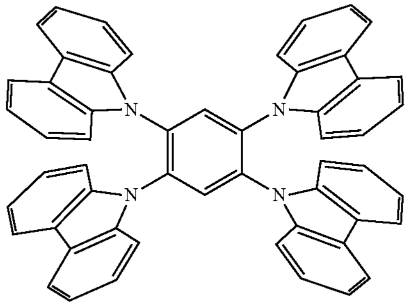
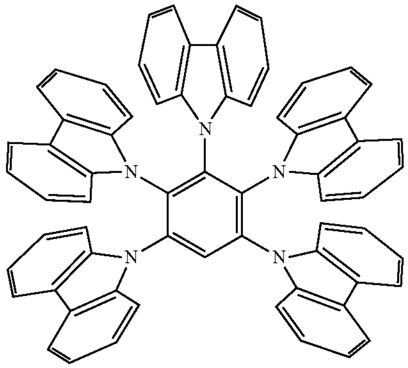
Exciton Barrier Layer
An exciton barrier layer inhibits excitons generated through recombination of holes and electrons in the light emitting layer from being diffused to the charge transporting layer. In some embodiments, the exciton barrier layer enables effective confinement of excitons in the light emitting layer. In some embodiments, the light emission efficiency of the device is enhanced. In some embodiments, the exciton barrier layer is adjacent to the light emitting layer on any of the side of the anode and the side of the cathode, and on both the sides. In some embodiments, where the exciton barrier layer is on the side of the anode, the layer can be between the hole transporting layer and the light emitting layer and adjacent to the light emitting layer. In some embodiments, where the exciton barrier layer is on the side of the cathode, the layer can be between the light emitting layer and the cathode and adjacent to the light emitting layer. In some embodiments, a hole injection layer, an electron barrier layer, or a similar layer is between the anode and the exciton barrier layer that is adjacent to the light emitting layer on the side of the anode. In some embodiments, a hole injection layer, an electron barrier layer, a hole barrier layer, or a similar layer is between the cathode and the exciton barrier layer that is adjacent to the light emitting layer on the side of the cathode. In some embodiments, the exciton barrier layer comprises excited singlet energy and excited triplet energy, at least one of which is higher than the excited singlet energy and the excited triplet energy of the light emitting material, respectively.

Hole Transporting Layer

The hole transporting layer comprises a hole transporting material. In some embodiments, the hole transporting layer is a single layer. In some embodiments, the hole transporting layer comprises a plurality layers.

In some embodiments, the hole transporting material has one of injection or transporting property of holes and barrier property of electrons. In some embodiments, the hole transporting material is an organic material. In some embodiments, the hole transporting material is an inorganic material. Examples of known hole transporting materials that may be used herein include but are not limited to a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer, or a combination thereof. In some embodiments, the hole transporting material is selected from a porphyrin compound, an aromatic tertiary amine compound, and a styrylamine compound. In some embodiments, the hole transporting material is an aromatic tertiary amine compound. Preferred compound examples for use as the hole transporting material are shown below.

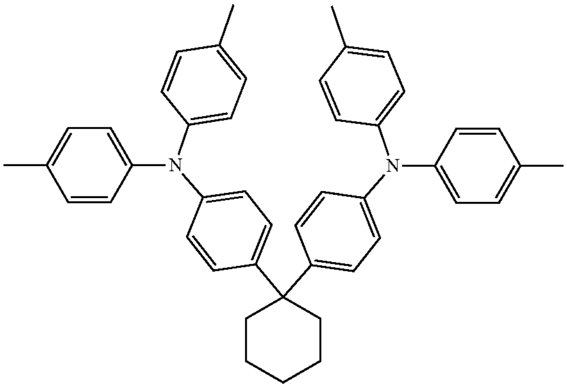

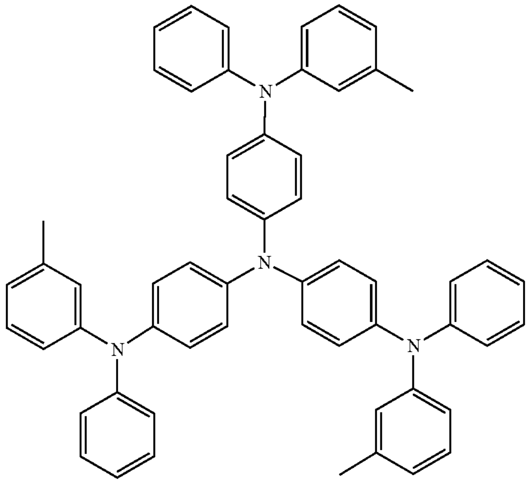

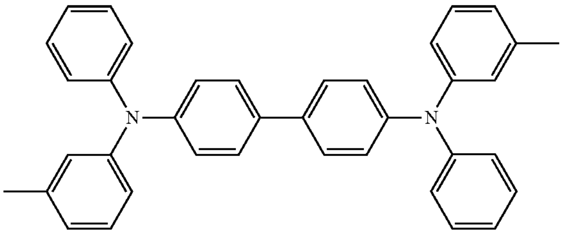

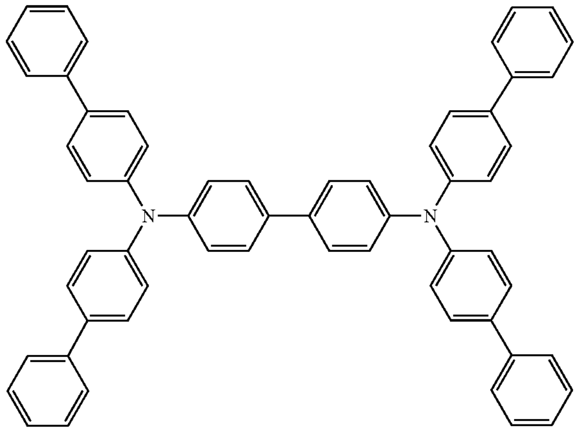

-continued
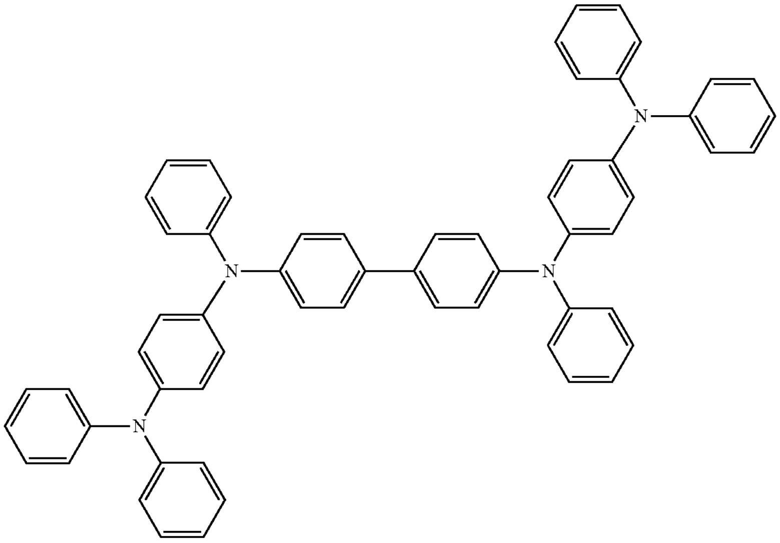
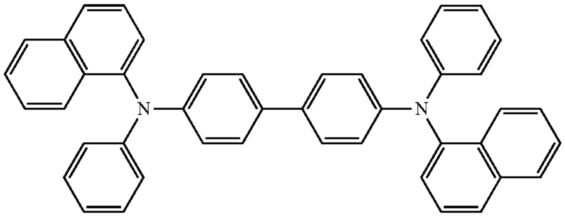
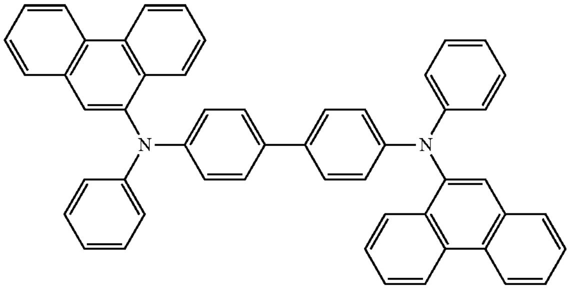
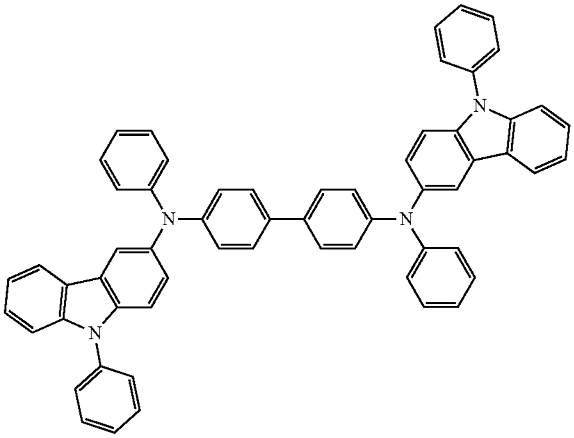
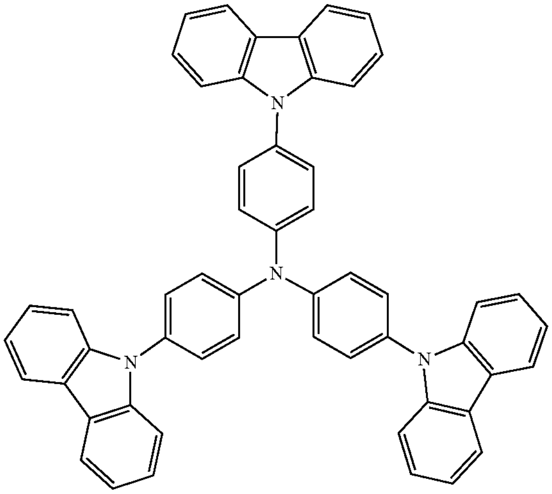

-continued

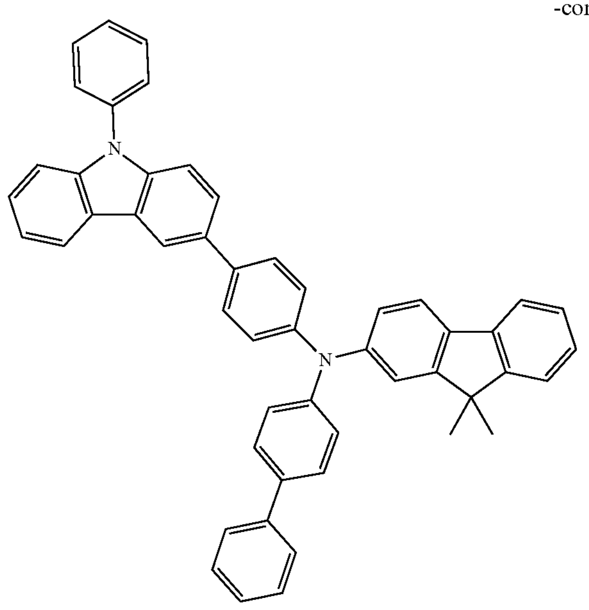

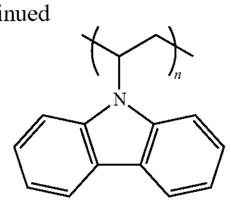

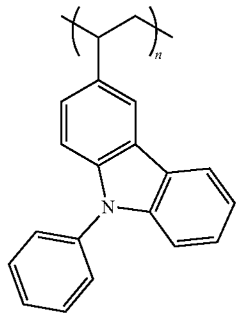

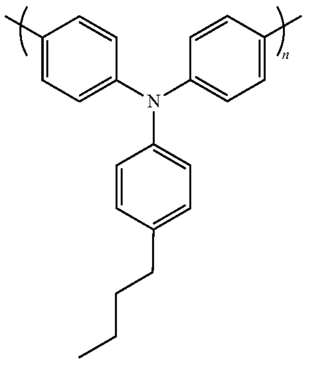

Electron Transporting Layer

The electron transporting layer comprises an electron transporting material. In some embodiments, the electron transporting layer is a single layer. In some embodiments, the electron transporting layer comprises a plurality of layer.

In some embodiments, the electron transporting material needs only to have a function of transporting electrons, which are injected from the cathode, to the light emitting layer. In some embodiments, the electron transporting material also function as a hole barrier material. Examples of the electron transporting layer that may be used herein include but are not limited to a nitro-substituted fluorene derivative, a diphenylquinone derivative, a thiopyran dioxide derivative, carbodiimide, a fluorenylidene methane derivative, anthraquinodimethane, an anthrone derivatives, an azole derivative, an azine derivative, an oxadiazole derivative, or a combination thereof, or a polymer thereof. In some embodiments, the electron transporting material is a thiadiazole derivative, or a quinoxaline derivative. In some embodiments, the electron transporting material is a polymer material. Preferred compound examples for use as the electron transporting material are shown below.

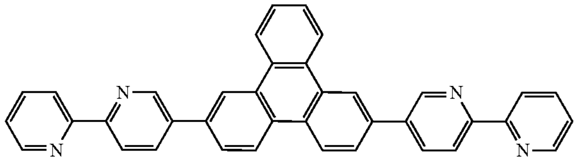

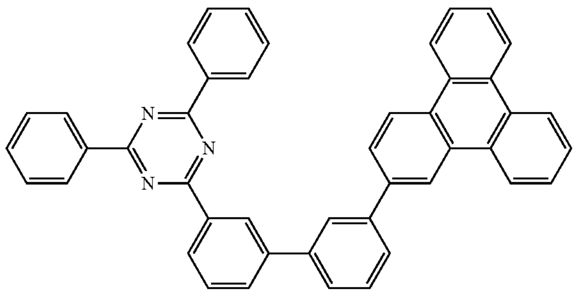

-continued
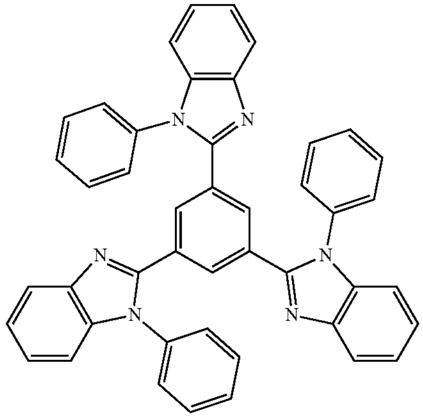
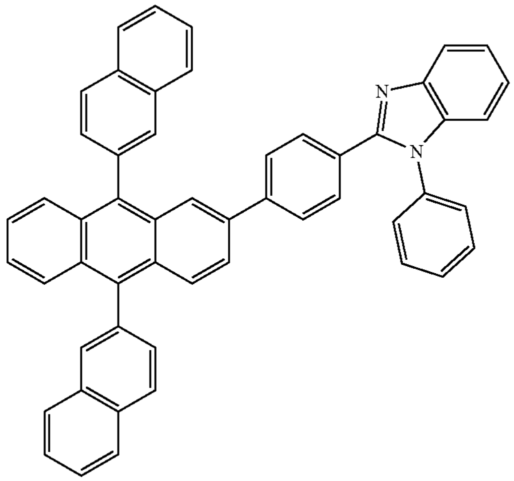
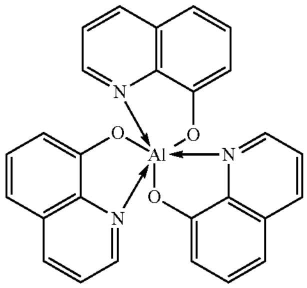
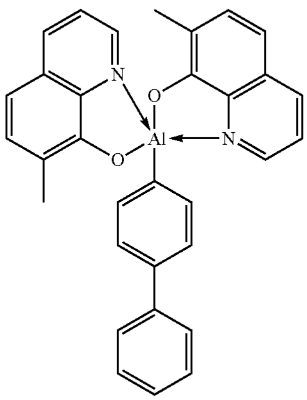
-continued
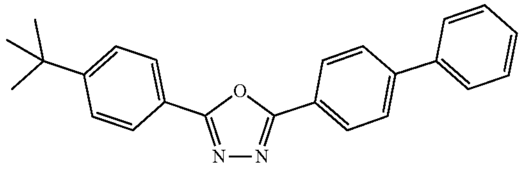
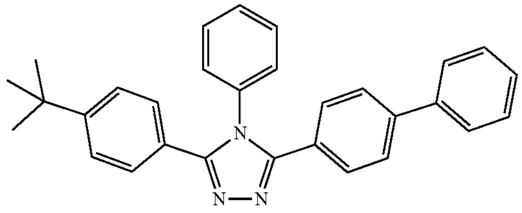
Hereinunder compound examples preferred as a material that can be added to the organic layers are shown. For example, these can be added as a stabilization material.
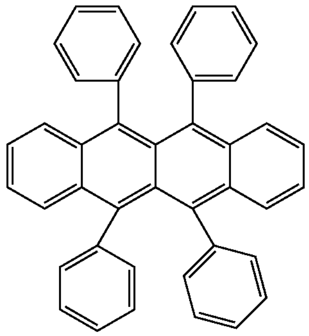
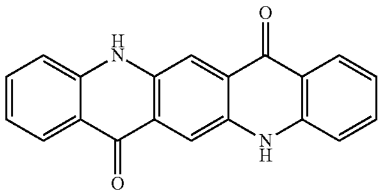
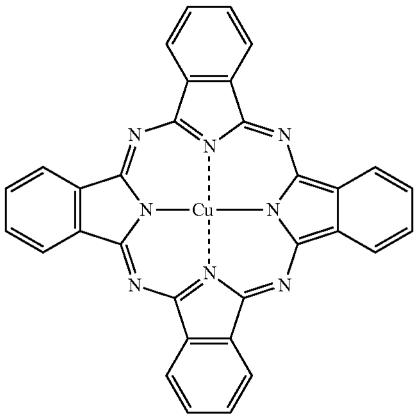

-continued

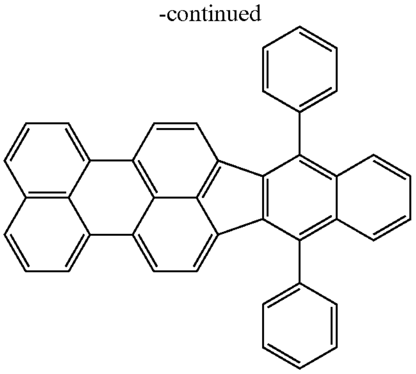

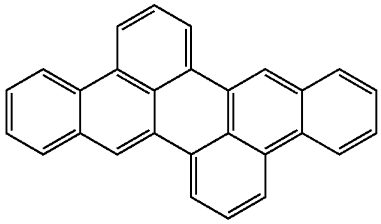

Preferred materials for use in the organic electroluminescent device are specifically shown. However, the materials usable in the invention should not be limitatively interpreted by the following exemplary compounds. Compounds that are exemplified as materials having a specific function can also be used as materials having any other function.

Devices

In some embodiments, an light emitting layer is incorporated into a device. For example, the device includes, but is not limited to an OLED bulb, an OLED lamp, a television screen, a computer monitor, a mobile phone, and a tablet.

In some embodiments, an electronic device comprises an OLED comprising an anode, a cathode, and at least one organic layer comprising a light emitting layer between the anode and the cathode.

In some embodiments, compositions described herein may be incorporated into various light-sensitive or light-activated devices, such as a OLEDs or photovoltaic devices. In some embodiments, the composition may be useful in facilitating charge transfer or energy transfer within a device and/or as a hole-transport material. The device may be, for example, an organic light emitting diode (OLED), an organic integrated circuit (O-IC), an organic field-effect transistor (O-FET), an organic thin-film transistor (O-TFT), an organic light emitting transistor (O-LET), an organic solar cell (O-SC), an organic optical detector, an organic photoreceptor, an organic field-quench device (O-FQD), a light emitting electrochemical cell (LEC) or an organic laser diode (O-laser).

Bulbs or Lamps

In some embodiments, an electronic device comprises an OLED comprising an anode, a cathode, and at least one organic layer comprising a light emitting layer between the anode and the cathode.

In some embodiments, a device comprises OLEDs that differ in color. In some embodiments, a device comprises an array comprising a combination of OLEDs. In some embodiments, the combination of OLEDs is a combination of three colors (e.g., RGB). In some embodiments, the combination of OLEDs is a combination of colors that are not red, green, or blue (for example, orange and yellow green). In some embodiments, the combination of OLEDs is a combination of two, four, or more colors.

In some embodiments, a device is an OLED light comprising:

a circuit board having a first side with a mounting surface and an opposing second side, and defining at least one aperture;

at least one OLED on the mounting surface, the at least one OLED configured to emanate light, comprising: an anode, a cathode, and at least one organic layer comprising a light emitting layer between the anode and the cathode;

a housing for the circuit board; and at least one connector arranged at an end of the housing, the housing and the connector defining a package adapted for installation in a light fixture.

In some embodiments, the OLED light comprises a plurality of OLEDs mounted on a circuit board such that light emanates in a plurality of directions. In some embodiments, a portion of the light emanated in a first direction is deflected to emanate in a second direction. In some embodiments, a reflector is used to deflect the light emanated in a first direction.

Displays or Screens

In some embodiments, the compounds of the invention can be used in a screen or a display. In some embodiments, the compounds of the invention are deposited onto a substrate using a process including, but not limited to, vacuum evaporation, deposition, vapor deposition, or chemical vapor deposition (CVD). In some embodiments, the substrate is a photoplate structure useful in a two-sided etch provides a unique aspect ratio pixel. The screen (which may also be referred to as a mask) is used in a process in the manufacturing of OLED displays. The corresponding artwork pattern design facilitates a very steep and narrow tie-bar between the pixels in the vertical direction and a large, sweeping bevel opening in the horizontal direction. This allows the close patterning of pixels needed for high definition displays while optimizing the chemical deposition onto a TFT backplane.

The internal patterning of the pixel allows the construction of a 3-dimensional pixel opening with varying aspect ratios in the horizontal and vertical directions. Additionally, the use of imaged "stripes" or halftone circles within the pixel area inhibits etching in specific areas until these specific patterns are undercut and fall off the substrate. At that point the entire pixel area is subjected to a similar etch rate but the depths are varying depending on the halftone pattern. Varying the size and spacing of the halftone pattern allows etching to be inhibited at different rates within the pixel allowing for a localized deeper etch needed to create steep vertical bevels.

A preferred material for the deposition mask is invar. Invar is a metal alloy that is cold rolled into long thin sheet in a steel mill. Invar cannot be electrodeposited onto a rotating mandrel as the nickel mask. A preferred and more cost feasible method for forming the open areas in the mask used for deposition is through a wet chemical etching.

In some embodiments, a screen or display pattern is a pixel matrix on a substrate. In some embodiments, a screen or display pattern is fabricated using lithography (e.g., photolithography and e-beam lithography). In some embodiments, a screen or display pattern is fabricated using a wet chemical etch. In further embodiments, a screen or display pattern is fabricated using plasma etching.

Methods of Manufacturing Devices

An OLED display is generally manufactured by forming a large mother panel and then cutting the mother panel in units of cell panels. In general, each of the cell panels on the mother panel is formed by forming a thin film transistor (ITT) including an active layer and a source/drain electrode on a base substrate, applying a planarization film to the TFT, and sequentially forming a pixel electrode, a light emitting layer, a counter electrode, and an encapsulation layer, and then is cut from the mother panel.

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light emitting layer, a counter electrode, and an encapsulation layer, and then is cut from the mother panel.

In another aspect, provided herein is a method of manufacturing an organic light emitting diode (OLED) display, the method comprising:

forming a barrier layer on a base substrate of a mother panel;

forming a plurality of display units in units of cell panels on the barrier layer;

forming an encapsulation layer on each of the display units of the cell panels;

applying an organic film to an interface portion between the cell panels.

In some embodiments, the barrier layer is an inorganic film formed of, for example, SiNx, and an edge portion of the barrier layer is covered with an organic film formed of polyimide or acryl. In some embodiments, the organic film helps the mother panel to be softly cut in units of the cell panel.

In some embodiments, the thin film transistor (TFT) layer includes a light emitting layer, a gate electrode, and a source/drain electrode. Each of the plurality of display units may include a thin film transistor (TT) layer, a planarization film formed on the TFT layer, and a light emitting unit formed on the planarization film, wherein the organic film applied to the interface portion is formed of a same material as a material of the planarization film and is formed at a same time as the planarization film is formed. In some embodiments, a light emitting unit is connected to the TFT layer with a passivation layer and a planarization film therebetween and an encapsulation layer that covers and protects the light emitting unit. In some embodiments of the method of manufacturing, the organic film contacts neither the display units nor the encapsulation layer.

Each of the organic film and the planarization film may include any one of polyimide and acryl. In some embodiments, the barrier layer may be an inorganic film. In some embodiments, the base substrate may be formed of polyimide. The method may further include, before the forming of the barrier layer on one surface of the base substrate formed of polyimide, attaching a carrier substrate formed of a glass material to another surface of the base substrate, and before the cutting along the interface portion, separating the carrier substrate from the base substrate. In some embodiments, the OLED display is a flexible display.

In some embodiments, the passivation layer is an organic film disposed on the TFT layer to cover the TFT layer. In some embodiments, the planarization film is an organic film formed on the passivation layer. In some embodiments, the planarization film is formed of polyimide or acryl, like the organic film formed on the edge portion of the barrier layer. In some embodiments, the planarization film and the organic film are simultaneously formed when the OLED display is manufactured. In some embodiments, the organic film may be formed on the edge portion of the barrier layer such that a portion of the organic film directly contacts the base substrate and a remaining portion of the organic film contacts the barrier layer while surrounding the edge portion of the barrier layer.

In some embodiments, the light emitting layer includes a pixel electrode, a counter electrode, and an organic light emitting layer disposed between the pixel electrode and the counter electrode. In some embodiments, the pixel electrode is connected to the source/drain electrode of the TFT layer.

In some embodiments, when a voltage is applied to the pixel electrode through the TFT layer, an appropriate voltage is formed between the pixel electrode and the counter electrode, and thus the organic light emitting layer emits light, thereby forming an image. Hereinafter, an image forming unit including the TFT layer and the light emitting unit is referred to as a display unit.

In some embodiments, the encapsulation layer that covers the display unit and prevents penetration of external moisture may be formed to have a thin film encapsulation structure in which an organic film and an inorganic film are alternately stacked. In some embodiments, the encapsulation layer has a thin film encapsulation structure in which a plurality of thin films are stacked. In some embodiments, the organic film applied to the interface portion is spaced apart from each of the plurality of display units. In some embodiments, the organic film is formed such that a portion of the organic film directly contacts the base substrate and a remaining portion of the organic film contacts the barrier layer while surrounding an edge portion of the barrier layer.

In one embodiment, the OLED display is flexible and uses the soft base substrate formed of polyimide. In some embodiments, the base substrate is formed on a carrier substrate formed of a glass material, and then the carrier substrate is separated.

In some embodiments, the barrier layer is formed on a surface of the base substrate opposite to the carrier substrate. In one embodiment, the barrier layer is patterned according to a size of each of the cell panels. For example, while the base substrate is formed over the entire surface of a mother panel, the barrier layer is formed according to a size of each of the cell panels, and thus a groove is formed at an interface portion between the barrier layers of the cell panels. Each of the cell panels can be cut along the groove.

In some embodiments, the method of manufacture further comprises cutting along the interface portion, wherein a groove is formed in the barrier layer, wherein at least a portion of the organic film is formed in the groove, and wherein the groove does not penetrate into the base substrate. In some embodiments, the TFT layer of each of the cell panels is formed, and the passivation layer which is an inorganic film and the planarization film which is an organic film are disposed on the TFT layer to cover the TFT layer. At the same time as the planarization film formed of, for example, polyimide or acryl is formed, the groove at the interface portion is covered with the organic film formed of, for example, polyimide or acryl. This is to prevent cracks from occurring by allowing the organic film to absorb an impact generated when each of the cell panels is cut along the groove at the interface portion. That is, if the entire barrier layer is entirely exposed without the organic film, an impact generated when each of the cell panels is cut along the groove at the interface portion is transferred to the barrier layer, thereby increasing the risk of cracks. However, in one embodiment, since the groove at the interface portion between the barrier layers is covered with the organic film and the organic film absorbs an impact that would otherwise be transferred to the barrier layer, each of the cell panels may be softly cut and cracks may be prevented from occurring in the barrier layer. In one embodiment, the organic film covering the groove at the interface portion and the planarization film are spaced apart from each other. For example, if the organic film and the planarization film are connected to each other as one layer, since external moisture may penetrate into the display unit through the planarization film and a portion where the organic film remains, the organic film and the planarization film are spaced apart from each other such that the organic film is spaced apart from the display unit.

In some embodiments, the display unit is formed by forming the light emitting unit, and the encapsulation layer is disposed on the display unit to cover the display unit. As such, once the mother panel is completely manufactured, the carrier substrate that supports the base substrate is separated from the base substrate. In some embodiments, when a laser beam is emitted toward the carrier substrate, the carrier substrate is separated from the base substrate due to a difference in a thermal expansion coefficient between the carrier substrate and the base substrate.

In some embodiments, the mother panel is cut in units of the cell panels. In some embodiments, the mother panel is cut along an interface portion between the cell panels by using a cutter. In some embodiments, since the groove at the interface portion along which the mother panel is cut is covered, with the organic film, the organic film absorbs an impact during the cutting. In some embodiments, cracks may be prevented from occurring in the barrier layer during the cutting.

In some embodiments, the methods reduce a defect rate of a product and stabilize its quality.

Another aspect is an OLED display including: a barrier layer that is formed on a base substrate; a display unit that is formed on the barrier layer; an encapsulation layer that is formed on the display unit; and an organic film that is applied to an edge portion of the barrier layer.

EXAMPLES

The features of the present invention will be described more specifically with reference to Synthesis Examples and Examples given below. The materials, processes, procedures and the like shown below may be appropriately modified unless they deviate from the substance of the invention. Accordingly, the scope of the invention is not construed as being limited to the specific examples shown below. Hereinunder the light emission characteristics were evaluated using a source meter (available from Keithley Corporation, Keithley 2400), a semiconductor parameter analyzer (available from Agilent Technology Corporation, E5273A), a light power meter apparatus (available from Newport Corporation, 1930C), an optical spectroscope (available from Ocean Optics Corporation, USB 2000), a spectroradiometer (available from Topcon Corporation, SR-3) and a streak camera (available from Hamamatsu Photonics K.K., C4334). The energies of HOMO and LUMO were measured by atmospheric photoelectron spectroscopy (such as AC-3 manufactured by Riken Keiki Co., Ltd.).

In the following Synthesis Examples, compounds included in the general formula (1) were synthesized.

Synthesis Example 1

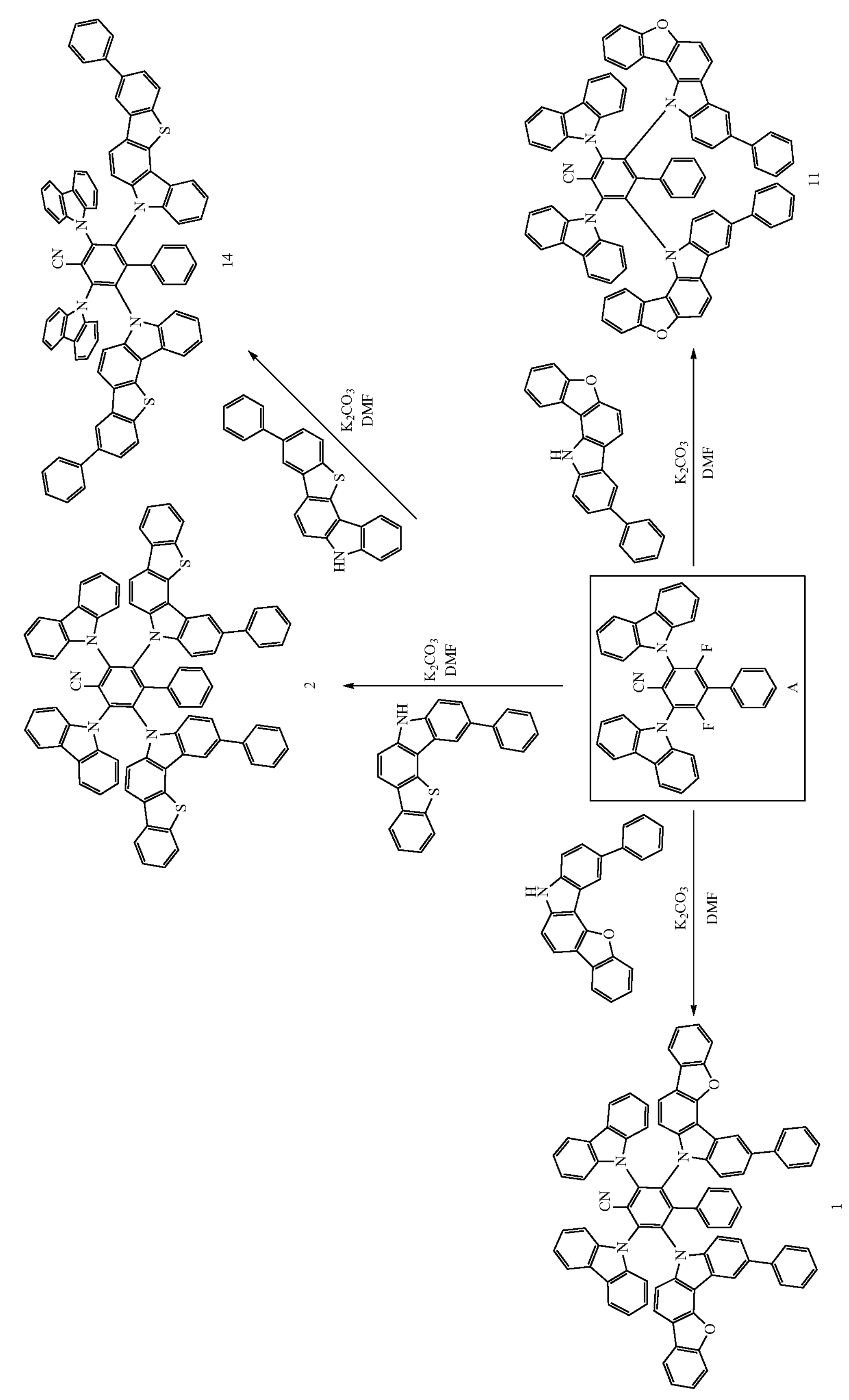
A
$K_2CO_3$
DMF
$K_2CO_3$
DMF
$K_2CO_3$
DMF
$K_2CO_3$
DMF
1
2
11
14

-continued
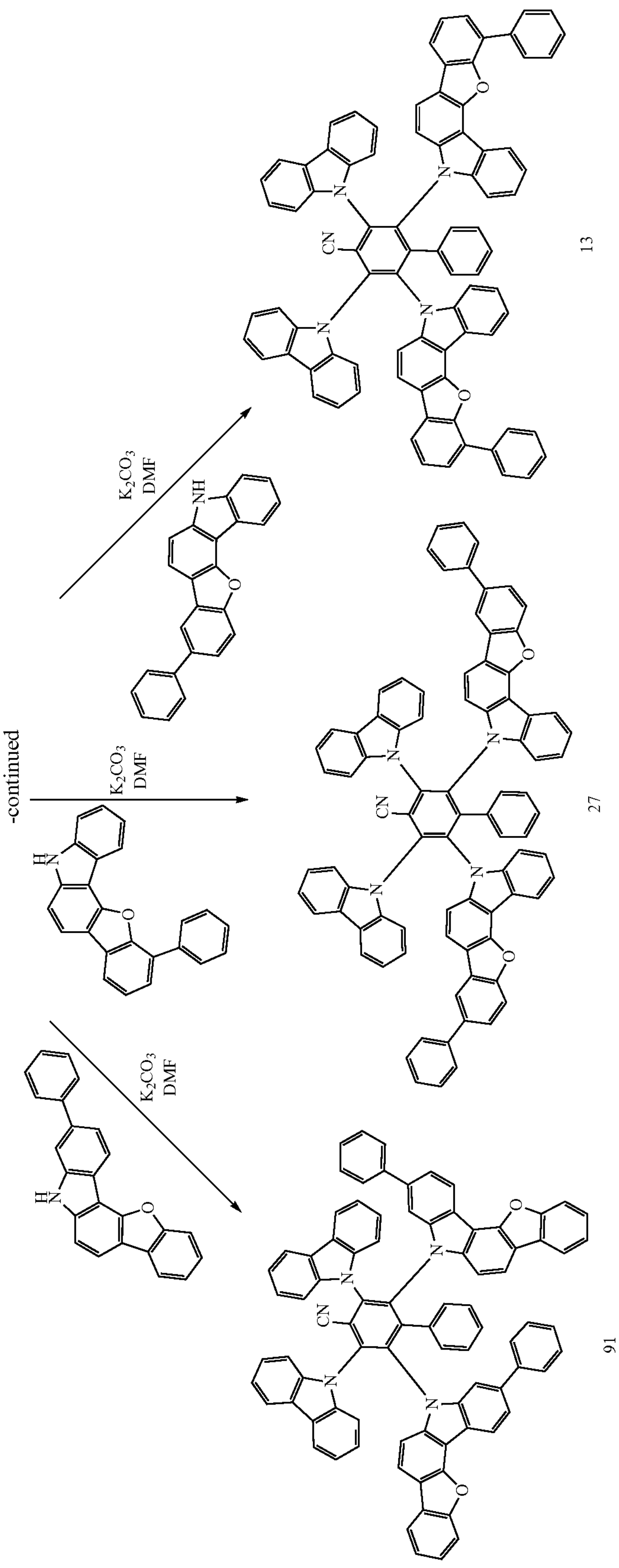
13
27
91

Compound 1

Compound A (0.75 g, 1.47 mmol) was added to a dimethylformamide solution (30 mL) of 2-phenyl-5H-benzofuro[3,2-c]carbazole (1.08 g, 2.2 mmol) and potassium carbonate (0.6 g, 3.0 mmol) under a nitrogen stream, and the mixture was stirred at 110° C. for 18 hours. The mixture was returned to room temperature, quenched by the addition of methanol, and the precipitated solid was filtered and washed with water and methanol. The obtained solid was purified by silica gel column chromatography to obtain Compound 1 (1.29 g, 1.1 mmol, yield 74.5%).

$^1$H NMR (400 MHz, $CDCl_3$) δ 8.24 (s, 2H), 7.90 (d, J=7.6 Hz, 2H), 7.77-7.55 (m, 12H), 7.52-7.48 (m, 4H), 7.47-7.26 (m, 12H), 7.21-7.03 (m, 10H), 7.00 (t, J=5.4, 5.6 Hz, 2H), 6.75 (d, J=7.6 Hz, 2H), 6.44-6.36 (m, 3H)

ASAP Mass Spectrometry: theoretical value 1171.39, observed value 1172.6

Compound 2

Compound A (0.87 g, 2.5 mmol) was added to a dimethylformamide solution (23 mL) of 2-phenyl-5H-[1]benzothieno[3,2-c]carbazole (0.65 g, 1.19 mmol) and potassium carbonate (0.41 g, 2.98 mmol) under a nitrogen stream, and the mixture was stirred at 60° C. for 17 hours. The mixture was returned to room temperature, quenched by the addition of methanol, and the precipitated solid was filtered and washed with water and methanol. The obtained solid was purified by silica gel column chromatography to obtain Compound 2 (1.08 g, 0.92 mmol, yield 77.1%).

$^1$H NMR (400 MHz, Chloroform-D) 8.64 (s, H), 8.08-8.03 (m, 2H), 7.98 (d, J=8.4 Hz, H), 7.89 (t, J=7.2, 5.6 Hz, H), 7.85 (d, J=8.8 Hz, H), 7.60 ppm (d, J=6.8 Hz, 21H), 7.55 (d, J=6.8 Hz, 2H), 7.51-7.11 (n, 15H), 6.827-6.75 (m, 2H), 6.71 (t, J=7.2, 8.0 Hz, 2H), 6.69-6.61 (m, J=7.6, 7.6 Hz, H), 6.52 (t, J=7.2, 8.4 Hz, H), 6.44 (t, J=8.4, 7.2 Hz, H)

ASAP Mass Spectrometry: theoretical value 1203.34, observed value 1172.52

Compound 11

Compound A (0.76 g, 1.40 mmol) was added to a solution of 9-phenyl-12H-benzofuro[3,2-a]carbazole (1.07 g, 3.22 mmol), and potassium carbonate (0.58 g, 4.20 mmol) in N,N-dimethylformamide (14.0 mL) under a nitrogen stream, and the mixture was stirred at 150° C. for 12 hours. The reaction mixture was returned to room temperature, water was added thereto, and the precipitate was filtered off. The filtrate was washed with methanol and dried in vacuo. The crude product was purified by silica gel column chromatography (hexane:toluene:chloroform=3.5:6.0:0.5) to obtain Compound 11 (1.00 g, 0.85 mmol, yield 76%) as a pale yellow solid.

$^1$H-NMR (400 MHz, $CDCl_3$): 7.97-7.95 (broad, 2H), 7.84-7.82 (m, 6H), 7.75-7.73 (m, 6H), 7.63 (d, J==8.2 Hz, 2H), 7.57-7.52 (m, 9H), 7.49-7.41 (n, 4H), 7.16 (d, J=8.2 Hz, 2H), 7.08 (t, J=8.2 Hz, 2H), 6.85-6.90 (m, 8H), 6.66 (d, J=8.2 Hz, 2H), 6.54 (t, J==8.2 Hz, 2H), 6.47 (t, J=8.2 Hz, 2H), 6.39 (d, J 8.2 Hz, 2H).

ASAP MS Spectrometry: $C_{85}H_{49}N_5O_2$: theoretical value 1171.39, observed value 1172.80

Compound 13

Compound A (0.8 g, 1.5 mmol) was added to a dimethylformamide solution (15 mL) of 9-phenyl-5H-benzofuro[3,2-c]carbazole (1.00 g, 3.0 mmol) and potassium carbonate (0.51 g, 3.7 mmol) under a nitrogen stream, and the mixture was stirred at 70° C. overnight. The mixture was returned to room temperature, quenched by the addition of water, and the precipitated solid was filtered and washed with methanol. The obtained solid was purified by silica gel column chromatography to obtain Compound 13 (1.6 g, 1.4 mmol, yield 93%).

$^1$H NMR (400 MHz, $CDCl_3$) δ 8.04 (s, 2H), 8.02 (d, J=7.2 Hz, 2H), 7.71 (dd, J=7.6, 3.2 Hz, 4H), 7.67 (d, J=8.0 Hz, 4H), 7.62 (d, J=5.6 Hz, 2H), 7.58 (d, J=9.6 Hz, 2H), 7.473 (t, J=8.0 Hz, 4H), 7.37 (t, J=6.8 Hz, 2H), 7.33 (d, J=6.0H, 2H), 7.31 (d, J=6.0 Hz, 2H), 7.18-7.08 (m, 18H), 6.67 (d, J=72 Hz, 24), 6.43 (t, J=7.6 Hz, 1H), 6.33 (t, J=7.6 Hz, 2H).

ASAP Mass Spectrometry: theoretical value 1172.89, observed value 1172.68.

Compound 14

Compound A (1.0 g. 1.8 mmol) was added to a dimethylformamide solution (36 mL) of 9-phenyl-5H-[1]benzofurothieno[3,2-c]carbazole (1.4 g, 4.0 mmol) and potassium carbonate (0.76 g, 5.5 mmol) under a nitrogen stream, and the mixture was stirred at 100° C. for 2 hours. The mixture was returned to room temperature, quenched by the addition of methanol, and the precipitated solid was filtered and washed with water and methanol. The obtained solid was purified by silica gel column chromatography to obtain Compound 14 (1.8 g, 1.5 mmol, yield 82%).

$^1$H NMR (400 MHz, DMSO) δ 8.68 (d, J=1.6 Hz, 2H), 8.36 (d, J=8.8 Hz, 2H), 8.21-8.01 (m, 10H), 7.87-7.85 (m, 8H), 7.75 (dd, J=1.6, 8.4 Hz, 2H), 7.67 (d, J=7.6 Hz, 2H), 7.54 (t, J=7.6 Hz, 4H), 7.42 (t, J=7.6 Hz, 2H), 730-7.20 (m, 6H), 7.18-7.04 (n, 6H), 6.91-6.71 (m, 2H), 6.37-6.24 (m, 3H)

ASAP Mass Spectrometry: theoretical value 1205.49, observed value 1205.63

Compound 27

Compound A (0.5 g, 0.92 mmol) was added to a dimethylformamide solution (18 mL) of 11-phenyl-5H-benzofuro[3,2-c]carbazole (0.80 g, 1.47 mmol) and potassium carbonate (0.51 g, 3.68 mmol) under a nitrogen stream, and the mixture was stirred at 100° C. for 4 hours. The mixture was returned to room temperature, quenched by the addition of methanol, and the precipitated solid was filtered and washed with water and methanol. The obtained solid was purified by silica gel column chromatography to obtain Compound 27 (1.21 g, 1.03 mmol, yield 70.0%), $^1$H NMR (400 MHz, Chloroform-D) 7.95 (d, J=6.8 Hz, 41H), 7.89 (d, J=6.8 Hz, 2H), 7.83 (d, J=8.0 Hz, 2H), 7.70 (d, J=76 Hz, 2H), 7.57-7.51 (m, 4H), 7.43-7.38 (m, 8H), 7.38-7.29 (m, 4H), 7.17-7.01 (m, 24H), 6.64 (d, J=7.2 Hz, 2H), 6.40 (t, J=7.6, 7.6 Hz, H), 6.31 (t, J=7.6, 7.2 Hz, 2H), ASAP Mass Spectrometry: theoretical value 1171.39, observed value 1172.7

Compound 91

Compound A (0.5 g, 0.92 mmol) was added to a dimethylformamide solution (18 ml) of 3-phenyl-5H-benzofuro[3,2-c]carbazole (0.67 g, 2.0 mmol) and potassium carbonate (0.32 g, 2.29 mmol) under a nitrogen stream, and the mixture was stirred at 80° C. for 14 hours. The mixture was returned to room temperature, quenched by the addition of methanol, and the precipitated solid was filtered and washed with water and methanol. The obtained solid was purified by silica gel column chromatography to obtain Compound 91 (0.82 g, 0.7 mmol, yield 76.9%).

$^1$H NMR (400 MH z, $CDCl_3$) 8.09 (d, J=8.0 Hz, 2H), 7.84 (t, J=7.6, 7.6 Hz, 4H), 7.7 ppm (d, J=7.6 Hz, 2H), 7.69 (d, J==8.4 Hz, 4H), 7.51-6.99 (m, 29H), 6.947 (t, J=7.2, 7.2 Hz, 21-1), 6.84 (t, J=7.2, 7.6 Hz, 2H), 6.61 (d, J=7.2 Hz, 2H), 6.36-6.28 (m, 2H)

ASAP Mass Spectrometry: theoretical value 1171.39, observed value 1173.61

Synthesis Example 2

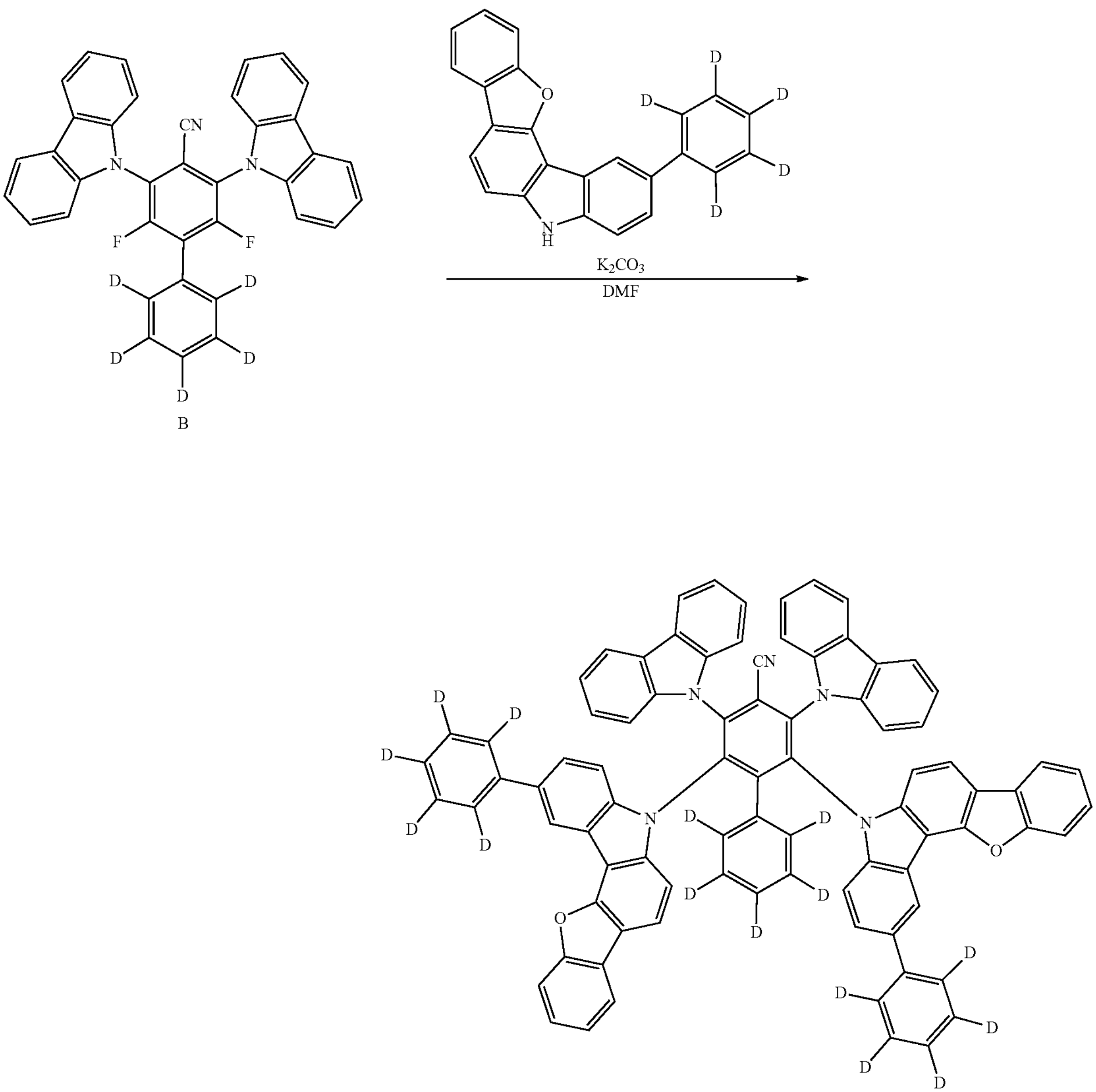

B

6035845

Compound 6035845

Under a nitrogen atmosphere, dimethylformamide (54 mL) was added to Compound B (1.5 g, 2.7 mmol), 2-phenyl-d5-5H-benzofuro[3,2-c]carbazole (1.9 g, 5.6 mmol), potassium carbonate (1.1 g, 8.1 mmol), and the mixture was stirred at 80° C. for 15 hours. The mixture was returned to room temperature, water was added thereto, and the precipitated solid was filtered. The obtained solid was subjected to silica gel column chromatography and reprecipitation to obtain Compound 6035845 (3.2 g, 2.6 mmol, yield 98%).

$^1$H NMR (400 MHz, $CDCl_3$) δ 8.21 (s, 2H), 7.88 (d, J=1.9 Hz, 2H), 7.76-7.64 (m, 4H), 7.64-7.53 (m, 48H), 7.46-7.30 (m, 7H), 7.30-7.20 (m, 4H), 7.20-6.91 (m, 11H),

ASAP Mass Spectrometry: theoretical value 1187.45, observed value 1188.06

Synthesis Example 3

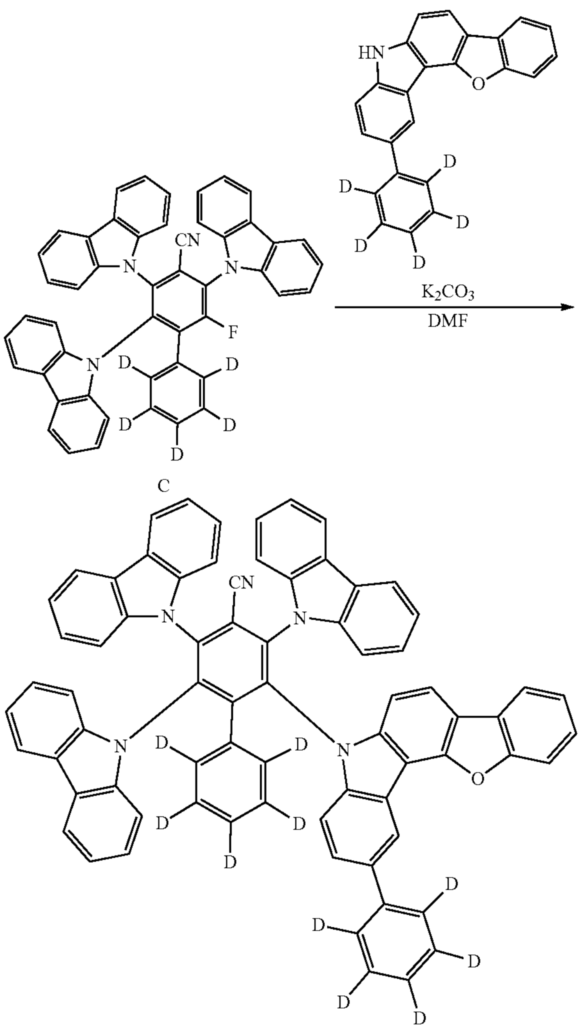

C

6298413

Compound 629841.3

Under a nitrogen stream, dimethylformamide (15 mL) was added to Compound C (1.1 g, 1.58 mmol), 2-phenyl-d5-5H-benzofuro[3,2-c]carbazole (0.59 g, 1.73 mmol), potassium carbonate (0.43 g, 3.15 mmol), and the mixture was stirred at 80° C. for 15 hours. The mixture was returned to room temperature, water was added thereto, and the precipitated solid was filtered. The obtained solid was subjected to silica gel column chromatography and reprecipitation to obtain Compound 6298413 (1.5 g, 1.5 mmol, yield 93%).

$^1$H NMR (400 MHz, $CDCl_3$) δ 8.19 (s, 18), 7.87 (d, 1=1.9 Hz, 1H), 7.75-7.51 (m, 81H), 7.40-7.29 (m, 4H). 7.25-7.02 (m, 13H), 6.99-6.93 (m, 6H)

ASAP Mass Spectrometry: theoretical value 1016.34, observed value 1016.70

(Example 1) Preparation and Evaluation of Thin Film

Compound 1 and H1 were vapor-deposited from different vapor deposition sources on a quartz substrate by a vacuum deposition method under conditions of a vacuum degree of less than $1\times10^{-3}$ Pa to form a thin film having a content of Compound 1 of 20% by weight and a thickness of 100 nm.

By using Compound 2, Compound 11, Compound 13, Compound 14, Compound 27, Compound 91, Compound 6035845, and Compound 6298413 and Comparative Compound 1 instead of Compound 1, thin films were prepared by the same procedure.

The maximum emission wavelength (λmax) and the photoluminescence quantum yield (PLQY) were measured when the formed thin films were irradiated with excitation light of 300 nm. In addition, the energy of HOMO and the energy of LUMO were also measured. The results are shown in Table 3.

TABLE 3

| Compound No. | PLQY (%) | HOMO (eV) | LUMO (eV) | λmax (nm) |
|---|---|---|---|---|
| Compound 1 | 95 | 6.0 | 3.4 | 489 |
| Compound 2 | 98 | 6.1 | 3.4 | 484 |
| Compound 11 | 90 | 6.2 | 3.5 | 487 |
| Compound 13 | 92 | 6.1 | 3.4 | 482 |
| Compound 14 | 98 | 6.1 | 3.5 | 481 |
| Compound 27 | 96 | 6.0 | 3.3 | 485 |
| Compound 91 | 87 | 6.1 | 3.4 | 487 |
| Compound 6035845 | 93 | 6.0 | 3.4 | 489 |
| Compound 6298413 | 99 | 6.0 | 3.2 | 489 |
| Comparative Compound 1 | 82 | 6.0 | 3.0 | 489 |

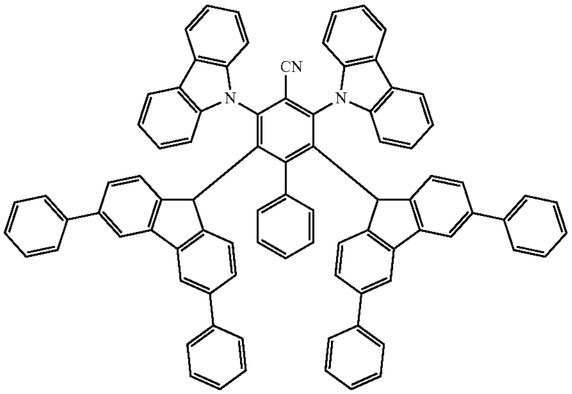

Comparative Compound 1

(Example 2) Production and Evaluation of Organic Electroluminescent Device

On a glass substrate on which an anode made of indium-tin oxide (ITO) having a film thickness of 50 nm was formed, each thin film was laminated by a vacuum deposition method at a vacuum degree of $5.0\times10^{-5}$ Pa First, HAT-CN was formed to a thickness of 10 nm on the TTO, NPD was formed to a thickness of 35 nm on the HAT-CN, and further PTCz was formed to a thickness of 10 nm on the NPD. Next, H1 and Compound 1 were vapor co-deposited from different vapor deposition sources to form a layer with a thickness of 40 nm as a light emitting layer. The content of Compound 1 in the light emitting layer was 30% by mass. Next, after ET1 was formed to a thickness of 10 nm, Liq and SF3-TRZ were vapor co-deposited from different vapor deposition sources to form a layer with a thickness of 20 nm. The contents of Liq and SF3-TRZ in this layer were 30% by mass and 70% by mass, respectively. Furthermore. Liq was formed to a thickness of 2 nm, and aluminum (Al) was vapor-deposited to a thickness of 100 nm to form a cathode, thereby obtaining an organic electroluminescent device.

Organic electroluminescent devices were produced in the same manner except that Compound 2, Compound 11, Compound 13, Compound 14, Compound 27, Compound 91, and Compound 6035845, and Comparative Compound 1 were used instead of Compound 1.

The maximum external quantum efficiency (EQE) of each organic electroluminescent device using Compound 1, Compound 2, Compound 11, Compound 13, Compound 14, Compound 27, Compound 91, or Compound 6035845 was measured and showed a high value of 21% to 26%. In addition, when the lifetime $\tau^2$ of delayed fluorescence of each organic electroluminescent device using Compound 1, Compound 2, Compound 11, Compound 13, Compound 27, or Compound 6035845 was measured, it was 2.2 to 2.9 μsec, which was shorter than the lifetime τ2 of delayed fluorescence (3.5 μsec) of the organic electroluminescent device using Comparative Compound 1.

In addition, regarding the organic electroluminescent device using Compound 1, the time (LT95) until the emission intensity at 5.5 mA/$cm^2$ became 95% of the starting intensity was measured, and it was confirmed that the time was 1.95 times longer than that of the organic electroluminescent device using Comparative Compound 1. In addition, it was also confirmed that the degree of alignment of a thin film obtained by doping 30% by mass of Compound 1 in H1 was −0.43, and the alignment property was high.

The compound represented by the general formula (1) has a high light emission efficiency, a short delayed fluorescence lifetime, and excellent alignment property. In addition, an organic electroluminescent device using the compound represented by the general formula (1) has a high light emission efficiency, a long device lifetime, and excellent durability.

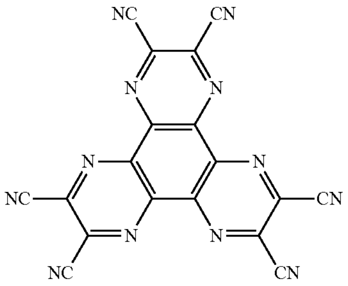

HAT-CN

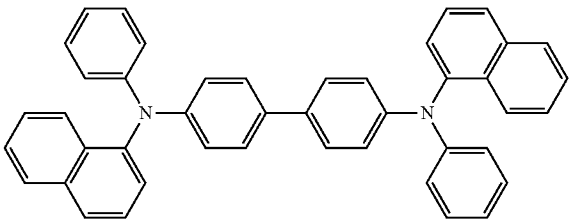

NPD

-continued

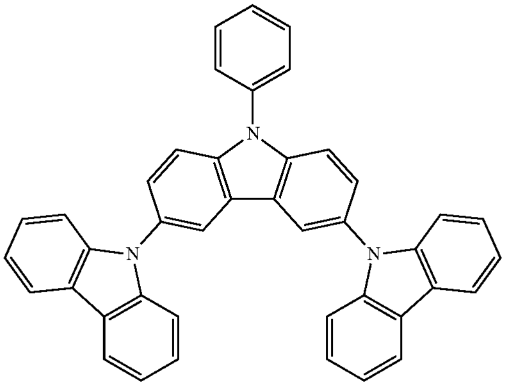

PTCz

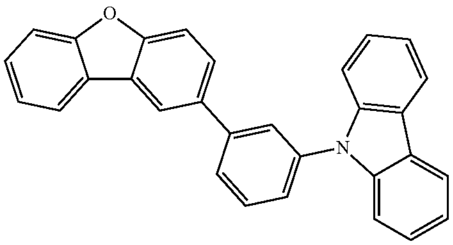

H1

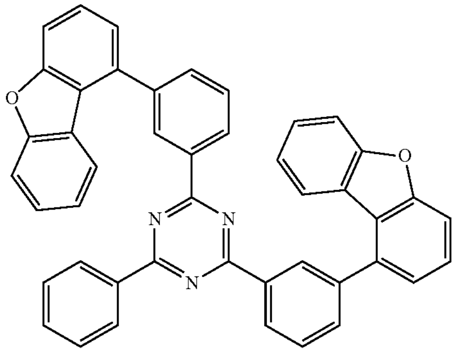

ET1

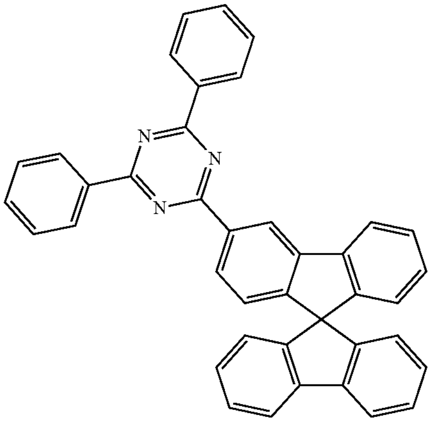

SF3-TRZ

-continued

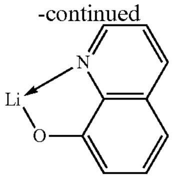

Liq

REFERENCE SIGNS LIST

1: Substrate
2: Anode
3: Hole injection layer
4: Hole transporting layer
5: Light emitting layer
6: Electron transporting layer
7: Cathode

The invention claimed is:

1. A compound represented by the following general formula (1):

General formula (1)

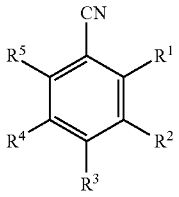

wherein $R^3$ is a substituted or unsubstituted aryl group of a monocyclic ring, $R^1$ and $R^5$ are unsubstituted carbazol-9-yl groups, and $R^2$ and $R^4$ are each independently a benzofuro- or benzothieno-fused carbazol-9-yl group substituted with an aryl group of a monocyclic ring.

2. The compound according to claim 1, wherein the compound has a line-symmetric structure.

3. A film comprising the compound according to claim 1.

4. An organic semiconductor device comprising the compound according to claim 1.

5. An organic light emitting device comprising the compound according to claim 1.

6. The organic light emitting device according to claim 5, wherein the device has a layer containing the compound, and the layer also contains a host material.

7. The organic light emitting device according to claim 6, wherein the layer containing the compound further contains a delayed fluorescent material in addition to the compound and the host material, and the delayed fluorescent material has a lowest excited singlet energy lower than that of the host material and higher than that of the compound.

8. The organic light emitting device according to claim 6, wherein the device has a layer containing the compound, and the layer also contains a light emitting material having a structure different from that of the compound.

9. The organic light emitting device according to claim 8, wherein an amount of light emitted from the light emitting material is larger than an amount of light emitted from the compound.

10. The organic light emitting device according to claim 6, wherein an amount of light emitted from the compound is the largest among materials contained in the device.

11. The organic light emitting device according to claim 5, which is an organic electroluminescent device.

12. The organic light emitting device according to claim 5, which emits delayed fluorescence.

* * * * *